United States Patent
Corkey et al.

(10) Patent No.: US 9,695,192 B2
(45) Date of Patent: *Jul. 4, 2017

(54) FUSED HETEROCYCLIC COMPOUNDS AS ION CHANNEL MODULATORS

(71) Applicant: GILEAD SCIENCES, INC., Foster City, CA (US)

(72) Inventors: Britton Kenneth Corkey, Redwood City, CA (US); Elfatih Elzein, Fremont, CA (US); Robert H. Jiang, Cupertino, CA (US); Rao V. Kalla, Cupertino, CA (US); Dmitry Koltun, Foster City, CA (US); Xiaofen Li, Mountain View, CA (US); Ruben Martinez, South San Francisco, CA (US); Eric Q. Parkhill, San Francisco, CA (US); Thao Perry, San Jose, CA (US); Jeff Zablocki, Los Altos, CA (US); Chandrasekar Venkataramani, Redwood City, CA (US); Michael Graupe, Pacifica, CA (US); Juan Guerrero, Concord, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/630,519

(22) Filed: Feb. 24, 2015

(65) Prior Publication Data

US 2015/0239904 A1    Aug. 27, 2015

Related U.S. Application Data

(63) Continuation of application No. 13/538,307, filed on Jun. 29, 2012, now Pat. No. 8,962,610.

(60) Provisional application No. 61/503,980, filed on Jul. 1, 2011.

(51) Int. Cl.
| | |
|---|---|
| *A61K 31/553* | (2006.01) |
| *C07D 267/14* | (2006.01) |
| *C07D 401/04* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 403/14* | (2006.01) |
| *C07D 413/04* | (2006.01) |
| *C07D 413/14* | (2006.01) |
| *C07D 471/12* | (2006.01) |
| *C07D 487/04* | (2006.01) |
| *C07D 498/04* | (2006.01) |
| *C07D 413/12* | (2006.01) |

(52) U.S. Cl.
CPC ......... *C07D 498/04* (2013.01); *C07D 267/14* (2013.01); *C07D 413/04* (2013.01); *C07D 413/12* (2013.01); *C07D 413/14* (2013.01)

(58) Field of Classification Search
CPC .. A61K 31/553; C07D 267/14; C07D 401/04; C07D 401/12; C07D 401/14; C07D 403/04; C07D 403/12; C07D 403/14; C07D 413/04; C07D 413/14; C07D 471/12; C07D 487/04
USPC ............... 514/211.04, 211.05, 211.09, 211.1, 514/211.13; 540/488, 490, 548, 551, 552
See application file for complete search history.

(56) References Cited

U.S. PATENT DOCUMENTS

| | | |
|---|---|---|
| 2,826,575 A | 3/1958 | Rigterink |
| 2,867,616 A | 1/1959 | George et al. |
| 2,867,618 A | 1/1959 | Rigterink |
| 3,441,649 A | 4/1969 | Bacaner |
| 3,483,193 A | 12/1969 | Gall et al. |
| 3,594,372 A | 7/1971 | Santilli et al. |
| 3,594,375 A | 7/1971 | Duennenberger et al. |
| 3,845,770 A | 11/1974 | Theeuwes |
| 4,062,881 A | 12/1977 | Kugele |
| 4,230,705 A | 10/1980 | Allen, Jr. et al. |
| 4,242,515 A | 12/1980 | Trust et al. |
| 4,244,953 A | 1/1981 | Trust et al. |
| 4,326,525 A | 4/1982 | Swanson et al. |
| 4,567,264 A | 1/1986 | Kluge et al. |

(Continued)

FOREIGN PATENT DOCUMENTS

| | | |
|---|---|---|
| CA | 2068255 | 11/1992 |
| CN | 1735605 | 2/2006 |

(Continued)

OTHER PUBLICATIONS

U.S. Appl. No. 14/217,011, filed Mar. 17, 2014, Kobayashi et al.

(Continued)

*Primary Examiner* — Brenda Coleman
(74) *Attorney, Agent, or Firm* — Francis O. Ginah

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

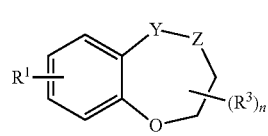

wherein Y, Z, n, $R^1$ and $R^3$ are as described herein, to methods for the preparation and use of the compounds and to pharmaceutical compositions containing the same.

7 Claims, No Drawings

(56) References Cited

U.S. PATENT DOCUMENTS

| | | |
|---|---|---|
| 4,654,343 A | 3/1987 | Albright et al. |
| 4,746,655 A | 5/1988 | Cale, Jr. |
| 4,812,565 A | 3/1989 | Cale, Jr. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,449 A | 10/1996 | Blackburn et al. |
| 5,616,345 A | 4/1997 | Geoghegan et al. |
| 5,773,186 A | 6/1998 | Takashima |
| 5,939,412 A | 8/1999 | Bondinell et al. |
| 6,011,150 A | 1/2000 | Iwasaki et al. |
| 6,303,607 B1 | 10/2001 | Wolff et al. |
| 6,369,062 B1 | 4/2002 | Wolff et al. |
| 6,479,496 B1 | 11/2002 | Wolff |
| 6,525,057 B2 | 2/2003 | Wolff et al. |
| 6,579,875 B1 | 6/2003 | Carling et al. |
| 6,908,917 B2 | 6/2005 | Ortwine |
| 6,998,408 B2 | 2/2006 | Pinto |
| 7,005,523 B2 | 2/2006 | Dombroski et al. |
| 7,122,677 B2 | 10/2006 | Reichard et al. |
| 7,157,490 B2 | 1/2007 | Colandrea et al. |
| 7,306,631 B2 | 12/2007 | Glenn, Jr. et al. |
| 7,456,187 B2 | 11/2008 | Ford et al. |
| 7,572,807 B2 | 8/2009 | Li et al. |
| 7,579,348 B2 | 8/2009 | Wang et al. |
| 7,790,741 B2 | 9/2010 | Calderwood et al. |
| 8,022,076 B2 | 9/2011 | Ford et al. |
| 8,212,041 B2 | 7/2012 | Albrecht et al. |
| 8,252,810 B2 | 8/2012 | Ozaki et al. |
| 8,258,138 B2 | 9/2012 | John et al. |
| 8,323,911 B2 | 12/2012 | Walsh |
| 8,361,998 B2 | 1/2013 | Bostrom et al. |
| 8,389,500 B2 | 3/2013 | Abelman et al. |
| 8,586,732 B2 | 11/2013 | Corkey et al. |
| 8,697,863 B2 | 4/2014 | Elzein et al. |
| 8,703,759 B2 | 4/2014 | Kobayashi et al. |
| 8,952,034 B2 | 2/2015 | Corkey et al. |
| 8,962,610 B2 | 2/2015 | Corkey et al. |
| 9,079,901 B2 | 7/2015 | Kobayashi et al. |
| 9,115,096 B2 | 8/2015 | Corkey et al. |
| 9,193,694 B2 | 11/2015 | Corkey et al. |
| 9,371,329 B2 | 6/2016 | Corkey et al. |
| 9,403,782 B2 | 8/2016 | Corkey et al. |
| 2004/0038974 A1 | 2/2004 | Ortwine |
| 2004/0063580 A1 | 4/2004 | Kuragano et al. |
| 2004/0204404 A1 | 10/2004 | Zelle et al. |
| 2004/0224959 A1 | 11/2004 | Ohkura et al. |
| 2004/0242572 A1 | 12/2004 | Stenkamp et al. |
| 2005/0239767 A1 | 10/2005 | Chan et al. |
| 2006/0094003 A1 | 5/2006 | Nattel et al. |
| 2007/0066584 A1 | 3/2007 | Yao et al. |
| 2007/0066617 A1 | 3/2007 | Mita et al. |
| 2007/0082037 A1 | 4/2007 | Toshimitsu et al. |
| 2007/0142376 A1 | 6/2007 | Fleenor et al. |
| 2008/0176830 A1 | 7/2008 | Adams et al. |
| 2008/0188509 A1 | 8/2008 | Toshimitsu et al. |
| 2008/0293939 A1 | 11/2008 | Culshaw et al. |
| 2009/0012095 A1 | 1/2009 | Zelle et al. |
| 2009/0012103 A1 | 1/2009 | Abelman et al. |
| 2009/0069300 A1 | 3/2009 | Zhou et al. |
| 2009/0124612 A1 | 5/2009 | Albrecht et al. |
| 2009/0131402 A1 | 5/2009 | Shirai et al. |
| 2009/0181986 A1 | 7/2009 | Abelman et al. |
| 2009/0203686 A1 | 8/2009 | Moloney et al. |
| 2009/0203707 A1 | 8/2009 | Rajamani et al. |
| 2009/0221555 A1 | 9/2009 | Ahmed et al. |
| 2009/0253689 A1 | 10/2009 | Baeschlin et al. |
| 2010/0056536 A1 | 3/2010 | Antzelevitch et al. |
| 2010/0099676 A1 | 4/2010 | Endoh et al. |
| 2010/0113449 A1 | 5/2010 | Abelman et al. |
| 2010/0113461 A1 | 5/2010 | Koltun et al. |
| 2010/0113514 A1 | 5/2010 | Abelman et al. |
| 2010/0125091 A1 | 5/2010 | Abelman et al. |
| 2010/0144715 A1 | 6/2010 | Hoyt et al. |
| 2010/0144745 A1 | 6/2010 | Bamberg et al. |
| 2010/0174065 A1 | 7/2010 | Heer et al. |
| 2010/0197684 A1 | 8/2010 | Abelman et al. |
| 2010/0240635 A1 | 9/2010 | Cordi et al. |
| 2011/0021521 A1 | 1/2011 | Corkey |
| 2011/0076292 A1 | 3/2011 | Blaquiere et al. |
| 2011/0183990 A1 | 7/2011 | Antzelevitch et al. |
| 2012/0010192 A1 | 1/2012 | Kobayashi et al. |
| 2012/0289493 A1 | 11/2012 | Corkey et al. |
| 2013/0005706 A1 | 1/2013 | Corkey et al. |
| 2013/0012492 A1 | 1/2013 | Corkey et al. |
| 2013/0184255 A1 | 7/2013 | Elzein et al. |
| 2014/0135317 A1 | 5/2014 | Corkey et al. |
| 2014/0221286 A1 | 8/2014 | Belardinelli et al. |
| 2014/0303158 A1 | 10/2014 | Corkey et al. |
| 2015/0045305 A1 | 2/2015 | Belardinelli et al. |
| 2015/0080370 A1 | 3/2015 | Kobayashi et al. |
| 2015/0225383 A1 | 8/2015 | Chiu et al. |
| 2015/0225384 A1 | 8/2015 | Chiu et al. |
| 2015/0239904 A1 | 8/2015 | Corkey et al. |
| 2015/0329558 A1 | 11/2015 | Corkey et al. |

FOREIGN PATENT DOCUMENTS

| | | |
|---|---|---|
| CN | 1794997 | 6/2006 |
| CN | 101258136 | 9/2008 |
| CN | 101522685 | 9/2009 |
| DE | 4010488 | 10/1991 |
| DE | 10317526 | 11/2004 |
| EP | 0017438 | 3/1983 |
| EP | 0464572 | 1/1992 |
| EP | 0477789 | 4/1992 |
| EP | 0540334 | 5/1993 |
| EP | 0597423 | 5/1994 |
| EP | 0635488 | 1/1995 |
| EP | 0999208 | 5/2000 |
| EP | 1182195 | 2/2002 |
| EP | 1333031 | 8/2003 |
| EP | 1354602 | 10/2003 |
| EP | 1803748 | 6/2010 |
| JP | 5675428 | 6/1981 |
| JP | 04209692 | 7/1992 |
| JP | 06-001779 | 1/1994 |
| JP | 06107647 | 4/1994 |
| JP | 09157262 | 6/1997 |
| JP | 11100394 | 4/1999 |
| JP | 2003277384 | 10/2003 |
| JP | 2003321461 | 11/2003 |
| JP | 2006-503875 | 2/2006 |
| JP | 2006063064 | 3/2006 |
| JP | 2006-203875 | 8/2006 |
| JP | 5271069 | 8/2013 |
| JP | 2014-509611 | 4/2014 |
| TW | 200726765 | 7/2007 |
| TW | 201020239 | 6/2010 |
| TW | 201103926 | 2/2011 |
| TW | I490217 | 7/2015 |
| WO | WO 93/00095 | 1/1993 |
| WO | WO 93/08174 | 4/1993 |
| WO | WO 94/13272 | 6/1994 |
| WO | WO 94/13292 | 6/1994 |
| WO | WO 97/03975 | 2/1997 |
| WO | WO-98-04521 | 2/1998 |
| WO | WO-98-04542 | 2/1998 |
| WO | WO 98/11890 | 3/1998 |
| WO | WO-98-18475 | 5/1998 |
| WO | WO-98-18476 | 5/1998 |
| WO | WO 98/47885 | 10/1998 |
| WO | WO-98-47886 | 10/1998 |
| WO | WO-98-54135 | 12/1998 |
| WO | WO 99/13038 | 3/1999 |
| WO | WO-99-37607 | 7/1999 |
| WO | WO 99/41246 | 8/1999 |
| WO | WO-99-41246 | 8/1999 |
| WO | WO 99/42456 | 8/1999 |
| WO | WO-99-62891 | 12/1999 |
| WO | WO-99-65904 | 12/1999 |
| WO | WO-00-12492 | 3/2000 |
| WO | WO-00-13687 | 3/2000 |

(56) References Cited

FOREIGN PATENT DOCUMENTS

| | | |
|---|---|---|
| WO | WO 00/23451 | 4/2000 |
| WO | WO-00-25774 | 5/2000 |
| WO | WO-01-00573 | 1/2001 |
| WO | WO-01-06276 | 1/2001 |
| WO | WO 01/16110 | 3/2001 |
| WO | WO 01/16263 | 3/2001 |
| WO | WO 01/16274 | 3/2001 |
| WO | WO 01/16275 | 3/2001 |
| WO | WO 01/16276 | 3/2001 |
| WO | WO 01/16277 | 3/2001 |
| WO | WO 01/16278 | 3/2001 |
| WO | WO-01-21609 | 3/2001 |
| WO | WO-01-21610 | 3/2001 |
| WO | WO-01-25189 | 4/2001 |
| WO | WO-01-25224 | 4/2001 |
| WO | WO-01-40231 | 6/2001 |
| WO | WO-01-46155 | 6/2001 |
| WO | WO 01/87883 | 11/2001 |
| WO | WO 02/18377 | 3/2002 |
| WO | WO-02-24655 | 3/2002 |
| WO | WO 02/38562 | 5/2002 |
| WO | WO-02-44137 | 6/2002 |
| WO | WO-02-46162 | 6/2002 |
| WO | WO-02-48131 | 6/2002 |
| WO | WO 02/010135 | 7/2002 |
| WO | WO-02-064581 | 8/2002 |
| WO | WO 02/072579 | 9/2002 |
| WO | WO-02-087568 | 11/2002 |
| WO | WO-02-088073 | 11/2002 |
| WO | WO 02/096873 | 12/2002 |
| WO | WO-02-100825 | 12/2002 |
| WO | WO-03-000675 | 1/2003 |
| WO | WO 03/024941 | 3/2003 |
| WO | WO-03/033480 | 4/2003 |
| WO | WO-03-063797 | 8/2003 |
| WO | WO 03/075858 | 9/2003 |
| WO | WO-2004/014866 | 2/2004 |
| WO | WO 2004/020440 | 3/2004 |
| WO | WO-2004/024702 | 3/2004 |
| WO | WO 2004/026292 | 4/2004 |
| WO | WO 2004/037192 | 5/2004 |
| WO | WO 2004/043940 | 5/2004 |
| WO | WO 2004/062616 | 7/2004 |
| WO | WO-2004/083190 | 9/2004 |
| WO | WO 2004/094371 | 11/2004 |
| WO | WO 2004/096767 | 11/2004 |
| WO | WO-2004/101509 | 11/2004 |
| WO | WO-2004-111057 | 12/2004 |
| WO | WO 2005/002520 | 1/2005 |
| WO | WO-2005/011690 | 2/2005 |
| WO | WO 2005/014558 | 2/2005 |
| WO | WO-2005-037780 | 4/2005 |
| WO | WO-2005-041967 | 5/2005 |
| WO | WO 2005/060967 | 7/2005 |
| WO | WO 2005/097052 | 10/2005 |
| WO | WO-2005-121149 | 12/2005 |
| WO | WO 2006/002470 | 1/2006 |
| WO | WO 2006/011669 | 2/2006 |
| WO | WO 2006/020959 | 2/2006 |
| WO | WO 2006/021544 | 3/2006 |
| WO | WO 2006/023750 | 3/2006 |
| WO | WO 2006/031676 | 3/2006 |
| WO | WO-2006/032518 | 3/2006 |
| WO | WO 2006/048727 | 5/2006 |
| WO | WO 2006/091897 | 8/2006 |
| WO | WO 2006/095014 | 9/2006 |
| WO | WO-2006-096014 | 9/2006 |
| WO | WO-2006-108837 | 10/2006 |
| WO | WO 2006/113864 | 10/2006 |
| WO | WO 2006/125119 | 11/2006 |
| WO | WO 2006/125972 | 11/2006 |
| WO | WO 2006/138549 | 12/2006 |
| WO | WO 2006/138657 | 12/2006 |
| WO | WO 2006/138695 | 12/2006 |
| WO | WO 2007/004028 | 1/2007 |
| WO | WO-2007-020440 | 2/2007 |
| WO | WO 2007/023750 | 3/2007 |
| WO | WO 2007/038209 | 4/2007 |
| WO | WO 2007/047604 | 4/2007 |
| WO | WO 2007/058583 | 5/2007 |
| WO | WO 2007/061677 | 5/2007 |
| WO | WO 2007/061696 | 5/2007 |
| WO | WO-2007-066127 | 6/2007 |
| WO | WO 2007/069986 | 6/2007 |
| WO | WO 2007/070866 | 6/2007 |
| WO | WO-2007-109211 | 9/2007 |
| WO | WO 2007/113226 | 10/2007 |
| WO | WO 2007/146284 | 12/2007 |
| WO | WO 2008/005338 | 1/2008 |
| WO | WO 2008/005457 | 1/2008 |
| WO | WO 2008/006540 | 1/2008 |
| WO | WO 2008/007661 | 1/2008 |
| WO | WO-2008/023336 | 2/2008 |
| WO | WO 2008/055068 | 5/2008 |
| WO | WO 2008/079570 | 7/2008 |
| WO | WO 2008/080012 | 7/2008 |
| WO | WO 2008/094909 | 8/2008 |
| WO | WO 2008/108445 | 9/2008 |
| WO | WO 2008/117061 | 10/2008 |
| WO | WO 2008/118141 | 10/2008 |
| WO | WO-2008/128086 | 10/2008 |
| WO | WO 2008/134553 | 11/2008 |
| WO | WO 2008/144483 | 11/2008 |
| WO | WO 2009/005675 | 1/2009 |
| WO | WO-2009/016462 | 2/2009 |
| WO | WO 2009/026444 | 2/2009 |
| WO | WO-2009/036144 | 3/2009 |
| WO | WO 2009/045753 | 4/2009 |
| WO | WO-2009-079624 | 6/2009 |
| WO | WO-2009-079630 | 6/2009 |
| WO | WO 2009/085980 | 7/2009 |
| WO | WO 2009/089027 | 7/2009 |
| WO | WO 2009/091374 | 7/2009 |
| WO | WO-2009/112275 | 9/2009 |
| WO | WO 2009/137462 | 11/2009 |
| WO | WO 2009/137499 | 11/2009 |
| WO | WO 2009/141026 | 11/2009 |
| WO | WO-2009/148452 | 12/2009 |
| WO | WO 2009/153589 | 12/2009 |
| WO | WO 2010/006292 | 1/2010 |
| WO | WO-2010-013995 | 2/2010 |
| WO | WO-2010-013996 | 2/2010 |
| WO | WO 2010/018686 | 2/2010 |
| WO | WO 2010/022001 | 2/2010 |
| WO | WO-2010-023445 | 3/2010 |
| WO | WO-2010-023446 | 3/2010 |
| WO | WO-2010-023448 | 3/2010 |
| WO | WO-2010/053757 | 5/2010 |
| WO | WO-2010/056865 | 5/2010 |
| WO | WO-2010/068461 | 6/2010 |
| WO | WO-2010/074807 | 7/2010 |
| WO | WO 2010/077680 | 7/2010 |
| WO | WO 2010/077686 | 7/2010 |
| WO | WO-2010/106249 | 9/2010 |
| WO | WO 2010/111534 | 9/2010 |
| WO | WO 2010/118208 | 10/2010 |
| WO | WO-2011/014462 | 2/2011 |
| WO | WO 2011/036280 | 3/2011 |
| WO | WO-2011/042920 | 4/2011 |
| WO | 2011056985 A2 | 5/2011 |
| WO | WO 2011/075607 | 6/2011 |
| WO | WO 2011/084733 | 7/2011 |
| WO | WO-2012/003392 | 1/2012 |
| WO | WO 2012/019071 | 2/2012 |
| WO | WO 2012/019076 | 2/2012 |
| WO | WO 2012/036233 | 3/2012 |
| WO | WO 2012/037105 | 3/2012 |
| WO | WO-2012/038813 | 3/2012 |
| WO | WO 2012/050918 | 4/2012 |
| WO | WO 2012/071509 | 5/2012 |
| WO | WO-2012/154760 | 11/2012 |
| WO | WO-2012/167212 | 12/2012 |
| WO | WO-2013/004551 | 1/2013 |
| WO | WO-2013/006400 | 1/2013 |

(56) References Cited

FOREIGN PATENT DOCUMENTS

| WO | WO-2013/006463 | 1/2013 |
|---|---|---|
| WO | WO 2013/006485 | 1/2013 |
| WO | WO-2013/043925 | 3/2013 |
| WO | WO-2013/097052 | 7/2013 |
| WO | WO-2013/098375 | 7/2013 |
| WO | WO 2013/112932 | 8/2013 |
| WO | WO-2013/185764 | 12/2013 |
| WO | WO-2014/134419 | 9/2014 |
| WO | WO-2015-123519 | 8/2015 |

OTHER PUBLICATIONS

Barsky et al., "Hypoglycemic Cyclic Amidines", J. Med. Chem, vol. 14, No. 1, 1971, pp. 40-44.

Belardinelli et al., "A Novel, Potent, and Selective Inhibitor of Cardiac Late Sodium Current Suppresses Experimental Arrhythmias," J. Pharm. Exp. Ther., 344(1), pp. 23-32, 2013.

Benson et al., "SUMO modification regulates inactivation of the voltage-gtes potassium channel Kv1.5" Proc. Nat. Acad. Sci., 104(6), pp. 1805-1810, 2007.

Burashnikov et al., "Role of late sodium channel current block in the management of atrial fibrillation," Cardiovascular Drugs and Therapy / Sponsored by the International Society of Cardiovascular Pharmacotherapy, 27(1), pp. 79-89, 2013.

Chiu et al., "Cycloaddition of Alpha-Chloroformylarylhydrazines with Pyridines Afford 2-Aryl-2H-[1,2,4]triazolo[4,3-a]pyridine-3-ones", Journal of the Chinese Chemical Society, Chinese Electronic Periodical Services, China, vol. 48, 2001, pp. 1135-1142.

Chouhan et al., "Domino Ring-Opening/Carboxamidation Reactions of N-Tosyl Aziridines and 2-Halophenols/Pyridinol: Efficient Synthesis of 1,4-Benzo- and Pyrido-oxazepinones", Organic Letters, vol. 12. No. 1, pp. 192-195, 2010.

Clare et al, Drug Discovery Today 2000, vol. 5, No. 11, 506-520.

Cleator et al., "Synthesis of Novel Benzoxathiazepine-1,1-dioxides by Means of a One-pot Multicomponent Reaction", Tetrahedron Letters, 51, pp. 1079-1082, 2010.

Database WPI, Week 198132, Thomson Scientific, London, abstract, 1981, XP-002690413, JP56075428.

Database WPI, Week 199346, Thomson Scientific, London, abstract, 1993, XP-002690414, JP5271069.

Dermer et al., Bio/Technology, 1994, 12:30.

Elzein et al., "Novel 1,3-dipropyl-8-(1-heteroarylmethyl-1 H-pyrazol-4-yl)-xanthine derivatives as high affinity and selective $A_{2B}$ adenosine receptor antagonists," Bioorganic & Medicinal Chemistry Letters, 16:302-306 (2006).

Foster, "Deuterium Isotope Effects in Studies of Drug Metabolism", Trends Pharmacol. Sci., 5(12):524-527, 1984.

Freshney et al., Culture of Animal Cells, A Manual of Basic Technique, Alan R. Liss, Inc., 1983, New York, pp. 1-6.

Hale et al., Journal of Molecular and Cellular Cardiology, vol. 44 (2008), pp. 954-967.

International Search Report and Written Opinion for PCT/US2011/042700, dated Aug. 17, 2011.

International Search Report and Written Opinion for PCT/US2012/036976, dated Jul. 2, 2012.

International Search Report and Written Opinion for PCT/US2012/045086, dated Sep. 19, 2012.

International Search Report and Written Opinion for PCT/US2012/045021 dated Oct. 9, 2012.

International Search Report and Written Opinion for PCT/US2012/056419, dated Jan. 30, 2013.

International Search Report with Written Opinion for PCT/US2010/043264, dated Sep. 28, 2010.

International Search Report with Written Opinion for PCT/US2013/023291, dated Mar. 13, 2013.

Krafte et al., Current Opinion in Pharmacology 2008, 8:50-56.

Kumar et al., "New and emerging antiarrhythmic drugs for atrial fibrillation: what may become available to the clinician in the near future", Curr. Treat. Options Cardiovasc. Med., 11(55), 2009 pp. 373-380.

Nagashima et al., "Dual effects of disopyramide to the glycemic control in patients with diabetes mellitus", Diabetes, American Diabetes Association, vol. 53, No. Suppl. 2, 2004.

Ning et al., "Ranolazine Increases Beta-Cell Survival and Improves Glucose Homeostasis in Low-Dose Streptozotocin-induced Diabetes in Mice", J. Pharmacol. Exp. Ther., 337(1), 50-58, 2011.

Office Action for U.S. Appl. No. 12/843,702 dated Jul. 17, 2012.
Office Action, U.S. Appl. No. 12/843,702, dated Jan. 15, 2013.
Office Action, U.S. Appl. No. 12/843,702, dated Jul. 31, 2013.
Office Action, U.S. Appl. No. 13/174,587, dated May 14, 2013.
Office Action, U.S. Appl. No. 13/466,995, dated Jun. 9, 2014.
Office Action, U.S. Appl. No. 13/538,307, dated Apr. 24, 2014.
Office Action, U.S. Appl. No. 13/538,847, dated May 3, 2013.

Rudolph et al., "Quinazolinone Derivatives as Orally Available Ghrelin Receptor Antagonists for the Treatment of Diabetes and Obesity", Journal of Medicinal Chemistry, vol. 50, No. 21, 2007, pp. 5202-5216.

Rush et al., Molecular Interventions 2007, vol. 4, issue 7, 192-195.

Shin et al., "New Synthesis of Highly Potential Efficient Bluish-Green Electroluminescent Materials Based on 1,3,4-Oxadiazole Triazolopyridinone Carbazole Derivatives for Single-Layer Devices", Heteroatom Chemistry, Wiley Periodicals, Inc., vol. 17, No. 2, 2006, pp. 160-165.

Shin et al., "Synthesis and Characterization of New Bluish-Green Electroluminescent Materials Based on 1,3,4-Oxadiazole Triazolopyridinone Hybrids", Heteroatom Chemistry, Wiley Periodicals, Inc., vol. 10, No. 3, 2007, pp. 212-219.

Sircar, "Synthesis of new 1,2,4-triazolo[4,3-b]pyridazines and related compounds" Journal of Heterocyclic Chemistry 22(1):1045-1048 (1985). ISSN: 0022-152X.

Toussaint et al., "Late sodium current as a promising antiarrhythmic drug target for treatment of atrial fibrilolation?" Naunyn-Schmiedeberg's Archives of Pharmacology, 383(1), p. 61, 20117 77th Annual Meeting on German-Society-for Experimental-and-Clinical-Pharmacology-and Toxicology; Frankfurt, Germany; Mar. 30-Apr. 2, 2011.

Toyofuku et al. JP 06001779, Jan. 11, 1995; CA 122;10048, 1995. Abstract provided.

Vippagunta et al., "Crystalline Solids", Advanced Drug Delivery Reviews, 48, pp. 3-26, 2001.

Wu, et al., "Late Sodium Current Contributes to the Reverse Rate-Dependent Effect of I-KR Inihibition on Ventricular Repolarization", Circulation, 123(16), pp. 1713-1720, 2011.

Yang, et al., "Synthesis of Dibenzo[b,f][1,4]oxazepin-11(10H)-ones via Intramolecular Cyclocarbonylation Reactions Using pfl2/Cytop 292 as the Catalytic System", Journal of Organic Chemistry, 75(18), 2010, pp. 6297-6299, S1-S12.

Zaza et al., "Pathophysiology and Pharmacology of the Cardiac "Late Sodium Current"," Pharmacology and Therapeutics, 119, pp. 326-339, 2008.

Office Action, EP Application No. 10737724.1, dated Feb. 5, 2014.
Office Action, EP Application No. 10737724.1, dated Nov. 14, 2014.
Banker, G.S. et al, 'Modern Pharmaceutices, 3ed.', Marcel Dekker, New York. 1996, pp. 451 and 596.

Kahlig et al., PNAS, (2008), vol. 105, pp. 9799-9804.

Scirica, "Ranolazine in patients with coronary artery disease", Expert Opin. Pharmacother., 2007, vol. 8, No. 13, ISSN 1465-6566, pp. 2149-2157, XP008122077.

EP Search Report, EP Application No. 15177723.2, dated Nov. 9, 2015.

Office Action, NZ Application No. 618684, dated Oct. 15, 2014, 2 pages.

Office Action, AU Application No. 2012279214, dated Jul. 9, 2014, 3 pages.

Office Action, CN Application No. 201280032982.1, dated Nov. 15, 2014, 17 pages.

Office Action, CN Application No. 201280032982.1, dated Jul. 16, 2015, 16 pages.

Office Action, CN Application No. 201280032982.1, dated Feb. 19, 2016, 10 pages.

Office Action, EA Application No. 201391628, dated Sep. 4, 2015, 6 pages.

(56) References Cited

OTHER PUBLICATIONS

Office Action, EA Application No. 201391628, dated Nov. 9, 2014, 8 pages.
Office Action, IL Application No. 229714, dated Jun. 23, 2015, 5 pages.
Office Action, JP Application No. 2014-519167, dated Jan. 27, 2016, 10 pages.
Office Action, MX Application No. MX/a/2013/014843, dated Aug. 21, 2015, 3 pages.
Office Action, MX Application No. MX/a/2013/014843, dated Nov. 18, 2015, 2 pages.
Office Action, TW Application No. 101123292, dated May 20, 2014, 7 pages.
Abate et al., "Effects of bretylium tosylate on the atrio ventricular and intra ventricular conduction in man", Bollettino Della Societa Italiana di Cardiologia, Pensiero Scientifico, vol. 21, No. 4, 1975, pp. 601-608.
Agag et al., "Primary Amine-Functional Benzoxazine Monomers and Their Use for Amide-Containing Monomeric Benzoxazines," Macromolecules, 2010, 43(6):2748-2758.
Antoons, et al., "Late Na+ Current Inhibition by Ranolazine Reduces Torsades de Pointes in the Chronic Atrioventricular Block Dog Model," Journal of the American College of Cardiology, 55(8), 2010, pp. 801-809.
Baldwin et al., Kinase array design, back to front: Biaryl amides, Bioorganic & Medicinal Chemistry Letters, 18(2008), pp. 5285-5289.
Banchs, et al., "Efficacy and safety of dofetillide in patients with atrial fibrillation and atrial flutter," J. Interv. Card. Electrophysiol, 23, 2008, pp. 111-115.
Brady et al., "Synthesis of conformationally constrained benzoylureas as BH3-mimetics", Organic and Biomolecular Chemistry, vol. 10, No. 27, May 15, 2012 (May 15, 2012), pp. 5230-5237, XP002738888, DOI: 10.1039/C20625618E.
Caira, "Crystalline Polymorphism of Organic Compounds," Topics in Current Chemistry Springer, 198, 1998, pp. 163-208.
Christensen et al., "A Bifunctional Glucose-Dependent Regulator of Glucagon and Insulin Secretion in Humans", Diabetes, vol. 60, Dec. 2011, pp. 3103-3109.
Chylinska et al., "Dihydro-1,3-oxazine Derivatives and Their Antitumor Activity," Journal of Medicinal Chemistry, 1963, vol. 6:484-487.
Coppini et al., "Late Sodium Current Inhibition Reverses Electromechanical Dysfunction in Human Hypertrophic Cardiomyopathy", Feb. 2013.
Curran, "Potassium ion channels and human disease: phenotypes to drug targets?", Current Opinion in Biotechnology, vol. 9. No. 6, 1998, pp. 565-572.
Drici et al., "The bee venom peptide tertiapin underlines the role of IKACh in acetylcholine-induced artrioventricular blocks", British Journal of Pharmacology, vol. 131, No. 3, 2000, pp. 569-577.
Ege et al., "6-Fulor-Sowie 6-Nitro-3-phenyl-3,4-dihydro-1,2,3-benzo-triazin-4-on und deren Photolyse; nucleophile Substitution zur Erprobung der Fluor-Markierungsmethode von Suschitzky," Liabigs Ann. Chem. 1976, 946-968.
Final Official Action for Japanese Patent Application No. 2014-519167 dated Oct. 25, 2016. (4 pages).
Guidelines for Drug Treatment of Arrhythmias (JCS 2009), 2009, p. 16-24.
Ilyin, et al., "One-step assembly of carbamoyl substituted annulated 1,4-oxazepines", Tetrahedron Letters, (2006), 47(15):2649-2653, Supplementary Data 3 pages.
International Preliminary Report on Patentability for International Application No. PCT/US2010/043264 (WO/2011/014462) dated Jan. 31, 2012. (8 pages).
International Preliminary Report on Patentability for International Application No. PCT/US2011/042700 dated Jan. 8, 2013. (7 pages).
International Preliminary Report on Patentability for International Application No. PCT/US2012/036976 (WO/2012/154760) dated Nov. 12, 2013. (8 pages).
International Preliminary Report on Patentability for International Application No. PCT/US2012/045021 dated Jan. 7, 2014. (4 pages).
International Preliminary Report on Patentability for International Application No. PCT/US2012/045086 dated Jan. 7, 2014. (6 pages).
International Preliminary Report on Patentability for International Application No. PCT/US2012/056419 dated Mar. 25, 2014. (7 pages).
International Preliminary Report on Patentability for International Application No. PCT/US2013/023291 dated Jul. 29, 2014. (10 pages).
International Preliminary Report on Patentability for International Application No. PCT/US2014/019351 dated Sep. 1, 2015. (9 pages).
International Preliminary Report on Patentability for International Application No. PCT/US2015/015814 dated Aug. 16, 2016. (14 pages).
International Search Report and Written Opinion for PCT/US2014/019351, dated Jun. 30, 2014. (15 pages).
International Search Report and Written Opinion for PCT/US2015/015652 dated Apr. 22, 2015. (8 pages).
International Search Report and Written Opinion for PCT/US2015/015814, dated Aug. 17, 2015. (20 pages).
Jarvis et al., "A-803467, a potent and selective Nav1.8 sodium channel blocker, attenuates neuropathic and inflammatory pain in the rat", 2007, vol. 104, pp. 8520-8525.
Kamei et al., "Synthesis, SAR studies, and evaluation of 1,4-benzoxazepine derivatives as selective 5-HT1 A receptor agonists with neuroprotective effect: Discovery of Piclozotan", Bioorganic & Medicinal Chemistry, Pergamon, GB, vol. 14, No. 6, Mar. 15, 2006 (Mar. 15, 2006), pp. 1978-1992, XP027992458, ISSN: 0968-0896, DOI: 10.1016/j.bmc.2005.10.046.
Kerr et al., "Efficacy of azimilide for the maintenance of sinus rhythm in patients with paroxysmal atrial fibrillation in the presence and absence of structural heart disease", American Journal of Cardiology, vol. 98, No. 2, 2006, pp. 215-218.
Manikannan et al., "Chemoselective Reaction of Formalin with 2-(5-Substituted-2-hydroxybenzylamino)phenols: Synthesis of 6-Substituted 3-(2-hydroxyphenyl)-3,4-dihydro-2H-benzo[e][1,3]oxazines," Journal of Heterocyclic Chemistry, 2008, vol. 45:1207-1210.
Marc et al., "High Yield Phase Transfer N-Alkylation of Some Benzodiazepines by Esters of omega-Halo Acids," Syn. Comm. 1998, 28, pp. 1143-1157.
Menge et al., "Loss of Inverse Relationship Between Pulsatile Insulin and Glucagon Secretion in Patients With Type 2 Diabetes", Diabetes, vol. 60, Aug. 2011, pp. 2160-2168.
Murdock et al, "The Use of Oral Ranolazine to Convert New or Paroxysmal Atrial Fibrillation: A Review of Experience with Implications for Possible 'Pill in the Pocket' Approach to Atrial Fibrillation," Indian Pacing and Electrophysiology Journal, 9(5), 2009, pp. 260-267.
Neumayr et al., "Ibutilide and sinus arrest", Herz Kardiovaskulare Erkrankungen, Urban & Vogel, vol. 32, No. 4, 2007, p. 342.
Notification of the Search Report for Eurasian Application No. 201690899, dated Jun. 1, 2017. (3 pages).
Office Action and Search Report for Taiwan Application No. 101123292, dated Jun. 13, 2014. (3 pages).
Office Action for Pakistan Application No. 424/2012, dated Oct. 23, 2013. (2 pages).
Official Notification for Israel Application No. 229714 dated Dec. 4, 2016. (2 pages).
Oskarsson et al., "Circulating insulin inhibits glucagon secretion induced by arginine in type 1 diabetes", European Journal of Endocrinology (2000) 142, pp. 30-34.
Remington, "Remington's Pharmaceutical Sciences", 17th ed., 1985.
Roy et al., "Rhythm Control versus Rate Control for Atrial Fibrillation and Heart Failure", The New England Journal of Medicine, Jun. 19, 2008, vol. 358, pp. 2667-2677.
Seto, et al., "Design, synthesis, and evaluation of novel 2-substituted-4-aryl-6,7,8,9-tetrahydro-5H-pyrimido[4,5-b][1,5]oxazocin-5-ones as NK1 antagonists", Bioorganic & Medicinal Chemistry, (2005), 13(20):5717-5732.

(56) References Cited

OTHER PUBLICATIONS

Skidmore et al. (Journal of Medicinal Chemistry (2014), 57(24), 10424-10442).

Takahara et al., "Analysis of Arrhythmogenic profile in a canine model of chronic atrioventricular block by comparing in vitro effects of the class III antiarrhythmic drug nifekalant on the ventricular action potential indices between normal heart and atrioventricular block heart", Journal of Pharmacological Sciences, vol. 103, No. 2, Feb. 1, 2007 (Feb. 1, 2007), pp. 181-188.

Ulrich, Joachim, Kirk-Othmer Encyclopedia of Chemical Technology, 2002, John Wiley & Sons, Inc.

Vadnais, et al., "Emerging Clinical Role of Ranolazine in the Management of Angina," Ther. Clin. Risk Management, 6, 2010, pp. 517-530.

Wang et al., "Influence of Electronic Effects from Bridging Groups on Synthetic Reaction and Thermally Activated Polymerization of Bisphenol-Based Benzoxazines," Journal of Polymer Science: Part A: Polymer Chemistry, 2011, vol. 49(6):1443-1452.

Witty et al., Discovery of potent and stable conformationally constrained analogues of the MCH R1 antagonist SB-568849, Bioorganic & Medicinal Chemistry Letters 16 (2006), pp. 4872-4878.

Wolff et al., Burger's Medicinal Chemistry And Drug Discovery, 5th Ed., vol. I, John Wiley & Sons, Inc., 1995, pp. 949-982.

Wunsche et al., Skelettumlagerungen Unter Elektronenbeschuss-III Benzotriazinone Und 1,3-Diphenyltriazene, Tetrahedron, 1969, vol. 25, pp. 5869-5877.

Yamada, "The role of muscarinic K+ channels in the negative chronotropic effect of a muscarinic agonist", Journal of Pharmacology and Experimental Therapeutics, vol. 300, No. 1, 2002, pp. 681-687.

Yamazaki et al., "Negative chronotropic and dromotropic effects of E-4031, an I-Kr blocker, on the atrioventricular node in anesthetized dog hearts", European Journal of Pharmacology, vol. 297, No. 3, 1996, pp. 233-239.

FUSED HETEROCYCLIC COMPOUNDS AS ION CHANNEL MODULATORS

CROSS-REFERENCE TO RELATED APPLICATIONS

This application is a continuation of U.S. application Ser. No. 13/538,307, filed on Jun. 29, 2012, which claims the benefit under 35 U.S.C. §119(e) to U.S. Provisional Application No. 61/503,980, filed on Jul. 1, 2011, the entirety of which is incorporated herein by reference.

FIELD

The present disclosure relates to novel compounds and to their use in the treatment of various diseases, including cardiovascular diseases and diabetes. The disclosure also relates to methods for preparation of the compounds and to pharmaceutical compositions comprising such compounds.

BACKGROUND

The late sodium current (INaL) is a sustained component of the fast Na+ current of cardiac myocytes and neurons. Many common neurological and cardiac conditions are associated with abnormal (INaL) enhancement, which contributes to the pathogenesis of both electrical and contactile dysfunction in mammals. See, for example, Pathophysiology and Pharmacology of the Cardiac "Late Sodium Current", Pharmacology and Therapeutics 119 (2008) 326-339. Accordingly, compounds that selectively inhibit (INaL) in mammals are useful in treating such disease states.

One example of a selective inhibitor of (INaL) is RANEXA®, a compound approved by the FDA for the treatment of chronic stable angina pectoris. RANEXA® has also been shown to be useful for the treatment of a variety of cardiovascular diseases, including ischemia-reperfusion injury, arrhythmia and unstable angina, and also for the treatment of diabetes. It would be desirable to provide novel compounds that selectively inhibit INaL in mammals.

SUMMARY

Accordingly, typical embodiments the present disclosure provide novel compounds that function as late sodium channel blockers. In one embodiment, the disclosure provides compounds of Formula I:

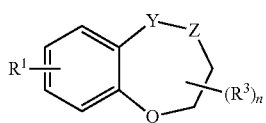

I wherein:
—Y—Z— is —C(=NR$^4$)—NR$^2$— or —C(NR$^5$R$^6$)=N—;
R$^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(=O)$_2$—R$^{26}$, —S(=O)$_2$—R$^{20}$, —O—S(=O)$_2$—R$^{20}$, —S(=O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and
  wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
R$^2$ is hydrogen, C$_{1-15}$ alkyl, —C(O)—R$^{20}$, —C(O)—OR$^{26}$, —C(O)—N(R$^{26}$)(R$^{26}$), —N(R$^{20}$)—S(=O)$_2$—R$^{20}$, cycloalkyl, aryl, heteroaryl or heterocyclyl;
  wherein said C$_{1-15}$ alkyl, cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN, oxo and —O—R$^{20}$;
  wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
  wherein said C$_{1-6}$ alkyl, cycloalkyl, aryl, heterocyclyl or heteroaryl are optionally further substituted with one, two or three substituents independently selected from the group consisting of halo, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;
n is 0, 1, 2, 3 or 4;
each R$^3$ is independently C$_{1-6}$ alkyl, cycloalkyl, aryl, heteroaryl or heterocyclyl;
  wherein said C$_{1-6}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
  wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
  wherein said C$_{1-6}$ alkyl, aralkyl, cycloalkyl, aryl, heterocyclyl or heteroaryl, are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
or two R$^3$ attached to a common carbon atom form an oxo;
or two R$^3$ attached to a common or adjacent carbon atoms form a cycloalkyl or heterocyclyl;

wherein said cycloalkyl or heterocyclyl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^4$ is C$_{1-6}$ alkyl, cycloalkyl, aryl, heteroaryl or heterocyclyl;

wherein said C$_{1-6}$ alkyl, cycloalkyl, aryl, heteroaryl or heterocyclyl are optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl or heteroaryl are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

or R$^2$ and R$^4$ can join together with the atom to which they are attached to form a heterocyclyl or heteroaryl;

wherein said heterocyclyl or heteroaryl is optionally substituted with one, two or three substituents independently selected from the group consisting of halo, C$_{1-6}$ alkyl, cycloalkyl, heteroaryl, —CN, —O—R$^{20}$, —N(R$^{20}$)(R$^{22}$), —C(O)—R$^{20}$, —N(R$^{20}$)—C(O)—OR$^{20}$ and —C(O)—OR$^{20}$; and wherein said C$_{1-6}$ alkyl or heteroaryl are optionally substituted with one, two or three substituents independently selected from the group consisting of halo, —CN, —O—R$^{20}$, C$_{1-6}$ alkyl, aryl, and heteroaryl;

R$^5$ is hydrogen, C$_{1-6}$ alkyl, cycloalkyl, aryl, heteroaryl or heterocyclyl;

wherein said C$_{1-6}$ alkyl, cycloalkyl, aryl, heteroaryl or heterocyclyl are optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl or heteroaryl are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$;

R$^6$ is C$_{1-6}$ alkyl, cycloalkyl, aryl, heteroaryl or heterocyclyl;

wherein said C$_{1-6}$ alkyl, cycloalkyl, aryl, heteroaryl or heterocyclyl are optionally substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl or heteroaryl are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$;

or R$^5$ and R$^6$ can join together with the atom to which they are attached to form a heterocyclyl or heteroaryl;

wherein said heterocyclyl or heteroaryl is optionally substituted with one, two or three substituents independently selected from the group consisting of halo, C$_{1-6}$ alkyl, cycloalkyl, heterocyclyl, aryl, heteroaryl, —CN, oxo, —CN, —O—R$^{20}$, —N(R$^{20}$)(R$^{22}$), —N(R$^{20}$)—C(O)—R$^{20}$, —N(R$^{20}$)—C(O)—OR$^{20}$ and —C(O)—OR$^{20}$; and wherein said C$_{1-6}$ alkyl or heterocyclyl is optionally substituted with one, two or three substituents independently selected from the group consisting of halo, oxo, heteroaryl and —O—R$^{20}$;

R$^{20}$ and R$^{22}$ are in each instance independently selected from the group consisting of hydrogen, C$_{1-6}$ alkyl, cycloalkyl, heterocyclyl, aryl and heteroaryl; and wherein the C$_{1-6}$ alkyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —SO$_2$R$^{26}$, —CN, C$_{1-3}$ alkoxy, aryloxy, —CF$_3$, —OCF$_3$, —OCH$_2$CF$_3$, —C(O)—NH$_2$, aryl, cycloalkyl and heteroaryl;

wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclyl or heteroaryl which is then optionally substituted with one, two or three substituents independently selected from the group consisting of hydroxyl, halo, C$_{1-4}$ alkyl, aralkyl, aryloxy, aralkyloxy, acylamino, —NO$_2$, —SO$_2$R$^{26}$, —CN, C$_{1-3}$ alkoxy, —CF$_3$, —OCF$_3$, aryl, heteroaryl and cycloalkyl;

each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, stereoisomer, mixture of stereoisomers, or tautomer thereof; provided that when R$^2$ and R$^4$ join together with the atom to which they are attached to form an optionally substituted imidazolyl, the imidazolyl it is not directly substituted with an optionally substituted triazolyl, or R¹ is not optionally substituted pyrazolyl, 2-pyridinonyl or 2-fluoropyridinyl.

Some embodiments provide a method of using the compounds of Formula I, IA, IB or VII, or additional Formula(s) described throughout, in the treatment of a disease or condition in a mammal that is amenable to treatment by a late sodium channel blocker. Such diseases include cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease and intermittent claudication. Such diseases may also include diabetes and conditions related to diabetes, e.g. diabetic peripheral neuropathy. Such diseases may also include conditions affecting the neuromuscular system resulting in pain, seizures or paralysis. Therefore, it is contemplated that the compounds of the disclosure and their pharmaceutically acceptable salt, ester, stereoisomer, mixture of stereoisomers and/or tautomer forms are potentially of use as medicaments for the treatment of the aforementioned diseases.

In certain embodiments, the disclosure provides pharmaceutical compositions comprising a therapeutically effective amount of a compound of the disclosure (e.g. a compound of Formula I, IA, IB or VII or additional Formulas described throughout), and at least one pharmaceutically acceptable excipient.

In certain embodiments, the compound is:

| | |
|---|---|
| I-5 | 3-cyclopropyl-10-(4-(trifluoromethyl)phenyl)-5,6-dihydrobenzo[f][1,2,4]triazolo[4,3-d][1,4]oxazepine |
| I-6 | 3-methyl-10-(4-(trifluoromethyl)phenyl)-5,6-dihydrobenzo[f]imidazo[1,2-d][1,4]oxazepine |
| I-7 | 3-(pyrimidin-2-yl)-10-(4-(trifluoromethyl)phenyl)-5,6-dihydrobenzo[f]imidazo[1,2-d][1,4]oxazepine |
| I-18 | 3-cyclopropyl-10-(4-(trifluoromethoxy)phenyl)-5,6-dihydrobenzo[f]imidazo[1,2-d][1,4]oxazepine |
| II-1 | 5-morpholino-7-(4-(trifluoromethyl)phenyl)-2,3-dihydrobenzo[f][1,4]oxazepine |
| II-2 | N-benzyl-7-(4-(trifluoromethyl)phenyl)-2,3-dihydrobenzo[f][1,4]oxazepin-5-amine |
| II-3 | 5-(pyrrolidin-1-yl)-7-(4-(trifluoromethyl)phenyl)-2,3-dihydrobenzo[f][1,4]oxazepine |
| II-4 | N-cyclopropyl-7-(4-(trifluoromethyl)phenyl)-2,3-dihydrobenzo[f][1,4]oxazepin-5-amine |
| II-5 | N-benzyl-N-methyl-7-(4-(trifluoromethyl)phenyl)-2,3-dihydrobenzo[f][1,4]oxazepin-5-amine |
| II-9 | N-((3-fluoropyridin-2-yl)methyl)-7-(4-(trifluoromethyl)phenyl)-2,3-dihydrobenzo[f][1,4]oxazepin-5-amine |
| II-10 | N-(pyridin-2-ylmethyl)-7-(4-(trifluoromethyl)phenyl)-2,3-dihydrobenzo[f][1,4]oxazepin-5-amine |
| II-11 | N-(cyclopropylmethyl)-7-(4-(trifluoromethyl)phenyl)-2,3-dihydrobenzo[f][1,4]oxazepin-5-amine |
| II-13 | (S)-tert-butyl 1-(7-(4-(trifluoromethyl)phenyl)-2,3-dihydrobenzo[f][1,4]oxazepin-5-yl)pyrrolidin-3-ylcarbamate |
| II-14 | N-(2-(1H-imidazol-1-yl)ethyl)-7-(4-(trifluoromethyl)phenyl)-2,3-dihydrobenzo[f][1,4]oxazepin-5-amine |
| II-15 | (S)-N,N-dimethyl-1-(7-(4-(trifluoromethyl)phenyl)-2,3-dihydrobenzo [f][1,4]oxazepin-5-yl)pyrrolidin-3-amine |
| II-19 | N-(pyridin-2-yl)-7-(4-(trifluoromethyl)phenyl)-2,3-dihydrobenzo[f][1,4]oxazepin-5-amine |
| II-20 | N-(2-(pyridin-2-yloxy)ethyl)-7-(4-(trifluoromethyl)phenyl)-2,3-dihydrobenzo[f][1,4]oxazepin-5-amine |
| II-22 | N-(2-phenoxyethyl)-7-(4-(trifluoromethyl)phenyl)-2,3-dihydrobenzo[f][1,4]oxazepin-5-amine |
| II-24 | N-(2-(2-chlorophenoxy)ethyl)-7-(4-(trifluoromethyl)phenyl)-2,3-dihydrobenzo[f][1,4]oxazepin-5-amine |
| II-25 | 7-(4-(trifluoromethyl)phenyl)-N-((6-(trifluoromethyl)pyridin-2-yl)methyl)-2,3-dihydrobenzo[f][1,4]oxazepin-5-amine |
| II-31 | 5-(4-cyclopropylpiperazin-1-yl)-7-(4-(trifluoromethyl)phenyl)-2,3-dihydrobenzo[f][1,4]oxazepine |
| II-32 | N-phenyl-7-(4-(trifluoromethyl)phenyl)-2,3-dihydrobenzo[f][1,4]oxazepin-5-amine |
| II-33 | N-((1-methyl-1H-benzo[d]imidazol-2-yl)methyl)-7-(4-(trifluoromethyl)phenyl)-2,3-dihydrobenzo[f][1,4]oxazepin-5-amine |
| II-37 | N-(pyrimidin-2-ylmethyl)-1-(7-(4-(trifluoromethyl)phenyl)-2,3-dihydrobenzo[f][1,4]oxazepin-5-yl)pyrrolidin-3-amine |
| II-38 | (R)-tert-butyl methyl(1-(7-(4-(trifluoromethyl)phenyl)-2,3-dihydrobenzo[f][1,4]oxazepin-5-yl)pyrrolidin-3-yl)carbamate |
| II-39 | (R)-N-methyl-1-(7-(4-(trifluoromethyl)phenyl)-2,3-dihydrobenzo[f][1,4]oxazepin-5-yl)pyrrolidin-3-amine |
| II-40 | (S)-tert-butyl methyl(1-(7-(4-(trifluoromethyl)phenyl)-2,3-dihydrobenzo[f][1,4]oxazepin-5-yl)pyrrolidin-3-yl)carbamate |
| II-43 | (S)-tert-butyl 3-(7-(4-(trifluoromethyl)phenyl)-2,3-dihydrobenzo[f][1,4]oxazepin-5-ylamino)pyrrolidine-1-carboxylate |
| II-47 | (R)-N-(1-(7-(4-(trifluoromethyl)phenyl)-2,3-dihydrobenzo[f][1,4]oxazepin-5-yl)pyrrolidin-3-yl)picolinamide |
| II-48 | (S)-N,N-diethyl-1-(7-(4-(trifluoromethyl)phenyl)-2,3-dihydrobenzo[f][1,4]oxazepin-5-yl)pyrrolidin-3-amine |
| II-50 | (R)-tert-butyl 1-(7-(4-(trifluoromethyl)phenyl)-2,3-dihydrobenzo[f][1,4]oxazepin-5-yl)pyrrolidin-3-ylcarbamate |
| II-51 | (R)-N,N-dimethyl-1-(7-(4-(trifluoromethyl)phenyl)-2,3-dihydrobenzo[f][1,4]oxazepin-5-yl)pyrrolidin-3-amine |

-continued

| II-54 | N-phenyl-7-(4-(trifluoromethyl)phenyl)-2,3-dihydrobenzo[f][1,4]oxazepin-5-amine |
| II-55 | 5-(3-morpholinopyrrolidin-1-yl)-7-(4-(trifluoromethyl)phenyl)-2,3-dihydrobenzo[f][1,4]oxazepine |
| II-56 | (S)-1-(7-(4-(trifluoromethyl)phenyl)-2,3-dihydrobenzo[f][1,4]oxazepin-5-yl)pyrrolidin-3-amine |
| II-57 | tert-butyl 1-(7-(4-(trifluoromethyl)phenyl)-2,3-dihydrobenzo[f][1,4]oxazepin-5-yl)pyrrolidin-3-ylcarbamate |
| II-58 | 5-(2-(pyridin-2-yl)pyrrolidin-1-yl)-7-(4-(trifluoromethyl)phenyl)-2,3-dihydrobenzo[f][1,4]oxazepine |
| II-60 | 5-(3-(pyridin-2-yl)pyrrolidin-1-yl)-7-(4-(trifluoromethyl)phenyl)-2,3-dihydrobenzo[f][1,4]oxazepine |
| II-61 | 1-(naphthalen-1-yloxy)-3-((R)-1-(7-(4-(trifluoromethyl)phenyl)-2,3-dihydrobenzo[f][1,4]oxazepin-5-yl)pyrrolidin-3-ylamino)propan-2-ol |
| II-62 | tert-butyl 3-(7-(4-(trifluoromethyl)phenyl)-2,3-dihydrobenzo[f][1,4]oxazepin-5-ylamino)pyrrolidine-1-carboxylate |
| II-63 | (R)-tert-butyl 3-(7-(4-(trifluoromethyl)phenyl)-2,3-dihydrobenzo[f][1,4]oxazepin-5-ylamino)pyrrolidine-1-carboxylate | or a pharmaceutically acceptable salt, stereoisomer, mixture of stereoisomers, or tautomer thereof.

The inventions of this disclosure are described throughout. In addition, specific embodiments of the invention are as disclosed herein.

DETAILED DESCRIPTION

1. Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "C$_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$—R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

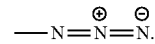

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$ R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$ R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$ R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$ R$^a$, in which R$^a$ is alkyl, aryl or heteroaryl and n is 0, 1 or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$ R$^a$, in which R$^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula (e.g. the compound of Formula I, which also includes Formula IA, IB and/or VII) is intended to encompass the compounds of the disclosure, and the pharmaceutically acceptable salts, stereoisomers, mixture of stereoisomers or tautomers of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of tautomers are shown below:

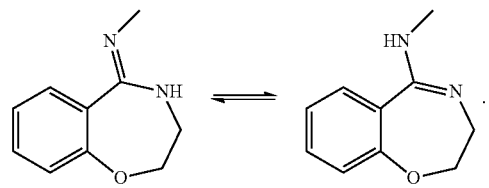

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I, IA, IB or VII and a solvent.

The term "hydrate" refers to the complex formed by the combining of a compound of Formula I, IA, IB or VII and water.

The term "prodrug" refers to compounds of Formula I, IA, IB or VII that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, IA, IB or VII compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, IA, IB or VII in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I, IA, IB or VII when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, IA, IB or VII.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" means administration of a compound of the invention, by or at the direction of a competent caregiver, to a mammal having a disease for purposes including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas trisubstituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-NH$_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs or calves when walking, climbing stairs or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia and the ventricular tachycardias (VTs), including idiopathic ventricular tachycardia, ventricular fibrillation, pre-excitation syndrome and Torsade de Pointes (TdP).

2. Nomenclature

Names of compounds of the present disclosure are provided using ACD/Name software for naming chemical compounds (Advanced Chemistry Development, Inc., Toronto). Other compounds or radicals may be named with common names or systematic or non-systematic names. The naming and numbering of the compounds of the disclosure is illustrated with a representative compound of Formula I:

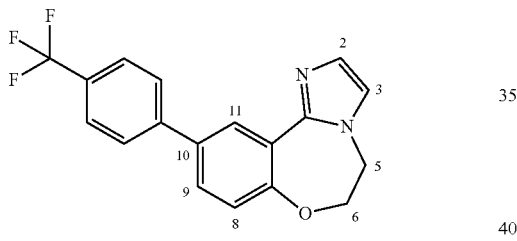

which is named 10-(4-(trifluoromethyl)phenyl)-5,6-dihydrobenzo[f]imidazo[1,2-d][1,4]oxazepine.

3. Compounds

Accordingly, typical embodiments the present disclosure provide novel compounds that function as late sodium channel blockers. In one embodiment, the disclosure provides compounds of Formula I:

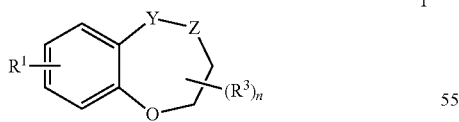

wherein:

—Y—Z— is —C(=NR$^4$)—NR$^2$— or —C(NR$^5$R$^6$)=N—;

R$^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(=O)$_2$—R$^{26}$, —S(=O)$_2$—R$^{20}$, —O—S(=O)$_2$—R$^{20}$, —S(=O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and
  wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is hydrogen, C$_{1-6}$ alkyl, —C(O)—R$^{20}$, —C(O)—OR$^{26}$, —C(O)—N(R$^{26}$)(R$^{26}$), —N(R$^{20}$)—S(=O)$_2$—R$^{20}$, cycloalkyl, aryl, heteroaryl or heterocyclyl;
  wherein said C$_{1-6}$ alkyl, cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN, oxo and —O—R$^{20}$;
  wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
  wherein said C$_{1-6}$ alkyl, cycloalkyl, aryl, heterocyclyl or heteroaryl are optionally further substituted with one, two or three substituents independently selected from the group consisting of halo, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;

n is 0, 1, 2, 3 or 4;

each R$^3$ is independently C$_{1-6}$ alkyl, cycloalkyl, aryl, heteroaryl or heterocyclyl;
  wherein said C$_{1-6}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
  wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
  wherein said C$_{1-6}$ alkyl, aralkyl, cycloalkyl, aryl, heterocyclyl or heteroaryl, are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

or two R$^3$ attached to a common carbon atom form an oxo;

or two $R^3$ attached to a common or adjacent carbon atoms form a cycloalkyl or heterocyclyl;
   wherein said cycloalkyl or heterocyclyl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^4$ is $C_{1-6}$ alkyl, cycloalkyl, aryl, heteroaryl or heterocyclyl;
   wherein said $C_{1-6}$ alkyl, cycloalkyl, aryl, heteroaryl or heterocyclyl are optionally substituted with one, two or three substituents independently selected from the group consisting of halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;
     wherein said cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and
     wherein said $C_{1-6}$ alkyl, aralkyl, cycloalkyl, aryl, heterocyclyl or heteroaryl are optionally further substituted with one, two or three substituents independently selected from the group consisting of hydroxyl, halo, $-NO_2$, $-N(R^{20})(R^{22})$, $-C(O)-R^{20}$, $-C(O)-OR^{20}$, $-C(O)-N(R^{20})(R^{22})$, $-CN$ and $-O-R^{20}$;

or $R^2$ and $R^4$ can join together with the atom to which they are attached to form a heterocyclyl or heteroaryl;
   wherein said heterocyclyl or heteroaryl is optionally substituted with one, two or three substituents independently selected from the group consisting of halo, $C_{1-6}$ alkyl, cycloalkyl, heteroaryl, $-CN$, $-O-R^{20}$, $-N(R^{20})(R^{22})$, $-C(O)-R^{20}$, $-N(R^{20})-C(O)-OR^{20}$ and $-C(O)-OR^{20}$; and
   wherein said $C_{1-6}$ alkyl or heteroaryl are optionally substituted with one, two or three substituents independently selected from the group consisting of halo, $-CN$, $-O-R^{20}$, $C_{1-6}$ alkyl, aryl, and heteroaryl;

$R^5$ is hydrogen, $C_{1-6}$ alkyl, cycloalkyl, aryl, heteroaryl or heterocyclyl;
   wherein said $C_{1-6}$ alkyl, cycloalkyl, aryl, heteroaryl or heterocyclyl are optionally substituted with one, two or three substituents independently selected from the group consisting of halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;
     wherein said cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and
     wherein said $C_{1-6}$ alkyl, aralkyl, cycloalkyl, aryl, heterocyclyl or heteroaryl are optionally further substituted with one, two or three substituents independently selected from the group consisting of hydroxyl, halo, $-NO_2$, $-N(R^{20})(R^{22})$, $-C(O)-R^{20}$, $-C(O)-OR^{20}$;

$R^6$ is $C_{1-6}$ alkyl, cycloalkyl, aryl, heteroaryl or heterocyclyl;
   wherein said $C_{1-6}$ alkyl, cycloalkyl, aryl, heteroaryl or heterocyclyl are optionally substituted with one, two or three substituents independently selected from the group consisting of halo, $-NO_2$, $C_{1-6}$ alkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;
     wherein said $C_{1-6}$ alkyl, cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and
     wherein said $C_{1-6}$ alkyl, aralkyl, cycloalkyl, aryl, heterocyclyl or heteroaryl are optionally further substituted with one, two or three substituents independently selected from the group consisting of hydroxyl, halo, $-NO_2$, $-N(R^{20})(R^{22})$, $-C(O)-R^{20}$, $-C(O)-OR^{20}$;

or $R^5$ and $R^6$ can join together with the atom to which they are attached to form a heterocyclyl or heteroaryl;
   wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, $-CN$, $-O-R^{20}$, $-N(R^{20})(R^{22})$, $-N(R^{20})-C(O)-R^{20}$, $-N(R^{20})-C(O)-OR^{20}$ and $-C(O)-OR^{20}$; and
   wherein said $C_{1-6}$ alkyl or heterocyclyl is optionally substituted with one, two or three substituents independently selected from the group consisting of halo, oxo, heteroaryl and $-O-R^{20}$;

$R^{20}$ and $R^{22}$ are in each instance independently selected from the group consisting of hydrogen, $C_{1-6}$ alkyl, cycloalkyl, heterocyclyl, aryl and heteroaryl; and
   wherein the $C_{1-6}$ alkyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, $-NO_2$, $-SO_2R^{26}$, $-CN$, $C_{1-3}$ alkoxy, aryloxy, $-CF_3$, $-OCF_3$, $-OCH_2CF_3$, $-C(O)-NH_2$, aryl, cycloalkyl and heteroaryl;
   wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclyl or heteroaryl which is then optionally substituted with one, two or three substituents independently selected from the group consisting of hydroxyl, halo, $C_{1-4}$ alkyl, aralkyl, aryloxy, aralkyloxy, acylamino, $-NO_2$, $-SO_2R^{26}$, $-CN$, $C_{1-3}$ alkoxy, $-CF_3$, $-OCF_3$, aryl, heteroaryl and cycloalkyl; and each $R^{26}$ is independently selected from the group consisting of hydrogen, $C_{1-4}$ alkyl, aryl and cycloalkyl;
   wherein the $C_{1-4}$ alkyl, aryl and cycloalkyl may be further substituted with from 1 to 3 substituents independently selected from the group consisting of hydroxyl, halo, $C_{1-4}$ alkoxy, $-CF_3$ and $-OCF_3$;

or a pharmaceutically acceptable salt, stereoisomer, mixture of stereoisomers, or tautomer thereof; provided that when $R^2$ and $R^4$ join together with the atom to which they are attached to form an optionally substituted imidazolyl, the imidazolyl it is not directly substituted with an optionally substituted triazolyl, or $R^1$ is not optionally substituted pyrazolyl, 2-pyridinonyl or 2-fluoropyridinyl.

In certain embodiments, the compound of Formula I is represented by Formula IA:

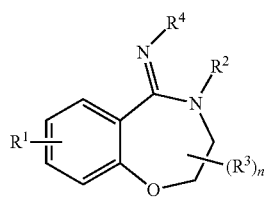

IA wherein:
$R^1$ is aryl, cycloalkyl, cycloalkenyl, heterocyclyl or heteroaryl;
 wherein said aryl, cycloalkyl, cycloalkenyl, heterocyclyl or heteroaryl are optionally substituted with one, two or three substituents independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(=O)$_2$—$R^{26}$, —S(=O)$_2$—$R^{20}$, —O—S(=O)$_2$—$R^{20}$, —S(=O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
  wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;
$R^2$ is hydrogen, $C_{1-6}$ alkyl, —C(O)—$R^{20}$, —C(O)—O$R^{26}$, —C(O)—N($R^{26}$)($R^{26}$), —N($R^{20}$)—S(=O)$_2$—$R^{20}$, cycloalkyl, aryl, heteroaryl or heterocyclyl;
 wherein said $C_{1-6}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN, oxo and —O—$R^{20}$;
  wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
  wherein said $C_{1-6}$ alkyl, cycloalkyl, aryl, heterocyclyl or heteroaryl are optionally further substituted with one, two or three substituents independently selected from the group consisting of halo, —$NO_2$, —$CF_3$, —N($R^{20}$)($R^{22}$), —C(O)—$R^{20}$, —C(O)—O$R^{20}$, —C(O)—N($R^{20}$)($R^{22}$), —CN, —S(O)$_2$—$R^{20}$ and —O—$R^{20}$;
n is 0, 1, 2, 3 or 4;
each $R^3$ is independently $C_{1-6}$ alkyl, cycloalkyl, aryl, heteroaryl or heterocyclyl;
 wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
  wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
or two $R^3$ attached to a common carbon atom form an oxo;
or two $R^3$ attached to a common or adjacent carbon atoms form a cycloalkyl or heterocyclyl;
 wherein said cycloalkyl or heterocyclyl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
$R^4$ is $C_{1-6}$ alkyl, cycloalkyl, aryl, heteroaryl or heterocyclyl;
 wherein said $C_{1-6}$ alkyl, cycloalkyl, aryl, heteroaryl or heterocyclyl are optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
  wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
or $R^2$ and $R^4$ can join together with the atom to which they are attached to form a heterocyclyl or heteroaryl;
 wherein said heterocyclyl or heteroaryl is optionally substituted with one, two or three substituents independently selected from the group consisting of halo, $C_{1-6}$ alkyl, cycloalkyl, heteroaryl, —CN, —O—$R^{20}$, —N(R²⁰)(R²²), —C(O)—R²⁰, —N(R²⁰)—C(O)—OR²⁰ and —C(O)—OR²⁰; and wherein said C₁₋₆ alkyl or heteroaryl are optionally substituted with one, two or three substituents independently selected from the group consisting of halo, —CN, —O—R²⁰, C₁₋₆ alkyl, aryl, and heteroaryl;

R²⁰ and R²² are in each instance independently selected from the group consisting of hydrogen, C₁₋₆ alkyl, cycloalkyl, heterocyclyl, aryl and heteroaryl; and wherein the C₁₋₆ alkyl, cycloalkyl, heterocyclyl, aryl and heteroaryl are optionally substituted with one, two or three substituents independently selected from the group consisting of hydroxyl, halo, C₁₋₄ alkyl, acylamino, oxo, —NO₂, —SO₂R²⁶, —CN, C₁₋₃ alkoxy, aryloxy, —CF₃, —OCF₃, —OCH₂CF₃, —C(O)—NH₂, aryl, cycloalkyl and heterocyclyl;
    wherein said heteroaryl is optionally further substituted with C₁₋₄ alkyl or cycloalkyl; or when R²⁰ and R²² are attached to a common nitrogen atom R²⁰ and R²² may join to form a heterocyclyl or heteroaryl which is then optionally substituted with one, two or three substituents independently selected from the group consisting of hydroxyl, halo, C₁₋₄ alkyl, aralkyl, aryloxy, aralkyloxy, acylamino, —NO₂, —SO₂R²⁶, —CN, C₁₋₃ alkoxy, —CF₃, —OCF₃, aryl, heteroaryl and cycloalkyl; and each R²⁶ is independently selected from the group consisting of hydrogen, C₁₋₄ alkyl, aryl and cycloalkyl;
  wherein the C₁₋₄ alkyl, aryl and cycloalkyl may be further substituted with from 1 to 3 substituents independently selected from the group consisting of hydroxyl, halo, C₁₋₄ alkoxy, —CF₃ and —OCF₃;

or a pharmaceutically acceptable salt, stereoisomer, mixture of stereoisomers, or tautomer thereof; provided that when R² and R⁴ join together with the atom to which they are attached to form an optionally substituted imidazolyl, the imidazolyl it is not directly substituted with an optionally substituted triazolyl, or R¹ is not optionally substituted pyrazolyl, 2-pyridinonyl or 2-fluoropyridinyl.

In some embodiments, R¹ is aryl;

wherein said aryl is optionally substituted with one, two or three substituents independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), N(R²⁰)—C(O)—R²², N(R²⁰)—C(O)—OR²², —N(R²⁰)—S(═O)₂—R²⁶, —S(═O)₂—R²⁰, —O—S(═O)₂—R²⁰, S(═O)₂—N(R²⁰)(R²²), C₁₋₆ alkyl, C₂₋₄ alkenyl, C₂₋₄ alkynyl, cycloalkyl, aryl, heteroaryl and heterocyclyl; and wherein said C₁₋₆ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, phenyl, heterocyclyl, heteroaryl, C₁₋₆ alkyl, cycloalkyl, —N(R²⁰)(R²²), —C(O)R²⁰, —C(O)—OR²⁰, —C(O)—N(R²⁰)(R²²), —CN and —O—R²⁰.

In some embodiments, R¹ is aryl optionally substituted with —O—R²⁰ or C₁₋₆ alkyl, wherein said C₁₋₆ alkyl is optionally substituted with one, two or three halo.

In some embodiments, R¹ is aryl optionally substituted with —O—R²⁰ or C₁₋₆ alkyl, wherein said C₁₋₆ alkyl is optionally substituted with one, two or three halo.

In some embodiments, R¹ is

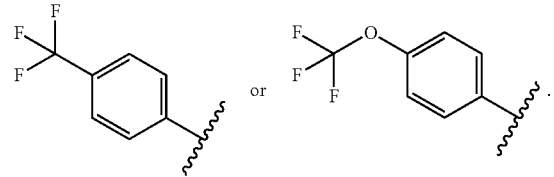 [SMILES: *c1ccc(C(F)(F)F)cc1 ; *c1ccc(OC(F)(F)F)cc1]

In some embodiments, R² and R⁴ join together with the atom to which they are attached to form a heterocyclyl or heteroaryl;

wherein said heterocyclyl or heteroaryl is optionally substituted with one, two or three substituents independently selected from the group consisting of halo, C₁₋₆ alkyl, cycloalkyl, heteroaryl, —CN, —O—R²⁰, —N(R²⁰)(R²²), —C(O)—R²⁰, —N(R²⁰)—C(O)—OR²⁰ and —C(O)—OR²⁰; and wherein said C₁₋₆ alkyl or heteroaryl are optionally substituted with one, two or three substituents independently selected from the group consisting of halo, —CN, —O—R²⁰, C₁₋₆ alkyl, aryl, and heteroaryl.

In some embodiments, R² and R⁴ join together with the atom to which they are attached to form a heterocyclyl or heteroaryl selected from the group consisting of

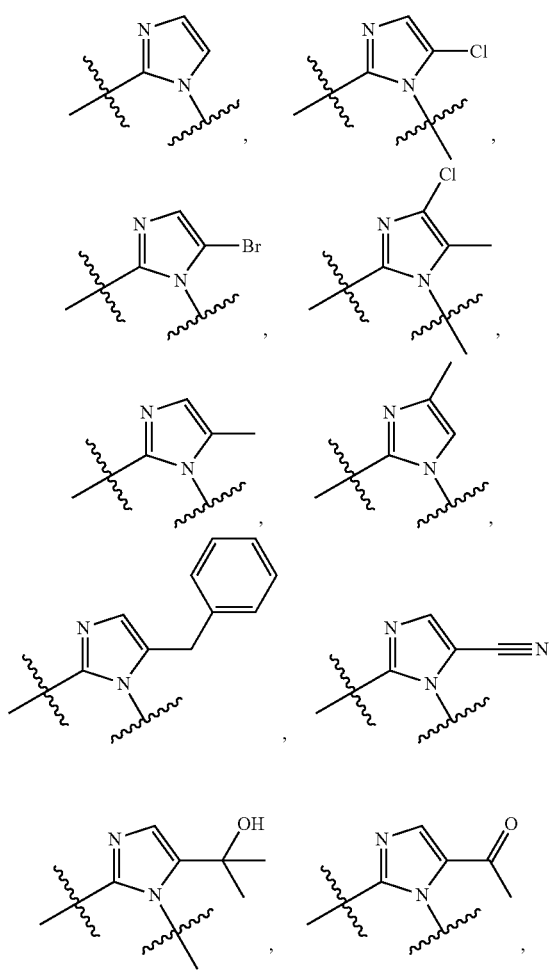

-continued

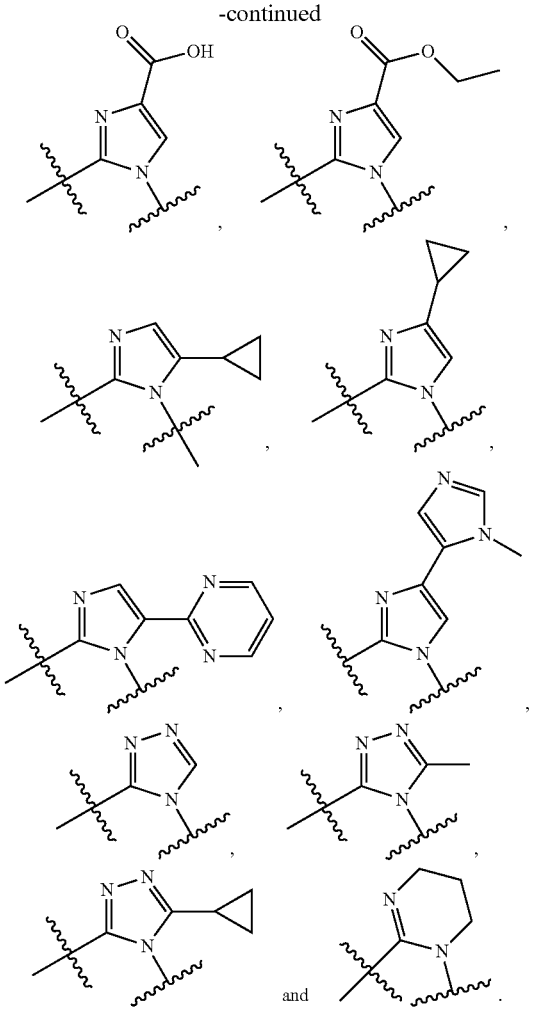

In some embodiments, n is 0.

In some embodiments, $R^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $N(R^{20})-C(O)-R^{22}$, $-N(R^{20})-C(O)-OR^{22}$, $-N(R^{20})-S(=O)_2-R^{26}$, $-S(=O)_2-R^{20}$, $-O-S(=O)_2-R^{20}$, $-S(=O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and
    wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;
  n is 0; and
  $R^2$ and $R^4$ join together with the atom to which they are attached to form a heterocyclyl or heteroaryl;
    wherein said heterocyclyl or heteroaryl is optionally substituted with one, two or three substituents independently selected from the group consisting of halo, $C_{1-6}$ alkyl, cycloalkyl, heteroaryl, $-CN$, $-O-R^{20}$, $-N(R^{20})(R^{22})$, $-C(O)-R^{20}$, $-N(R^{20})-C(O)-OR^{20}$ and $-C(O)-OR^{20}$; and
    wherein said $C_{1-6}$ alkyl or heteroaryl are optionally substituted with one, two or three substituents independently selected from the group consisting of halo, $-CN$, $-O-R^{20}$, $C_{1-6}$ alkyl, aryl, and heteroaryl.

In some embodiments, $R^1$ is aryl;
  wherein said aryl is optionally substituted with one, two or three substituents independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $N(R^{20})-C(O)-R^{22}$, $N(R^{20})-C(O)OR^{22}$, $-N(R^{20})-S(=O)_2-R^{26}$, $-S(=O)_2-R^{20}$, $-O-S(=O)_2-R^{20}$, $-S(=O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and
    wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;
  n is 0; and
  $R^2$ and $R^4$ join together with the atom to which they are attached to form a heterocyclyl or heteroaryl;
    wherein said heterocyclyl or heteroaryl is optionally substituted with one, two or three substituents independently selected from the group consisting of halo, $C_{1-6}$ alkyl, cycloalkyl, heteroaryl, $-CN$, $-O-R^{20}$, $-N(R^{20})(R^{22})$, $-C(O)-R^{20}$, $-N(R^{20})-C(O)-OR^{20}$ and $-C(O)-OR^{20}$; and
    wherein said $C_{1-6}$ alkyl or heteroaryl are optionally substituted with one, two or three substituents independently selected from the group consisting of halo, $-CN$, $-O-R^{20}$, $C_{1-6}$ alkyl, aryl, and heteroaryl.

In some embodiments, $R^1$ is aryl optionally substituted with $-O-R^{20}$ or $C_{1-6}$ alkyl;
  wherein said $C_{1-6}$ alkyl is optionally substituted with one, two or three halo;
  n is 0; and
  $R^2$ and $R^4$ join together with the atom to which they are attached to form a heterocyclyl or heteroaryl;
    wherein said heterocyclyl or heteroaryl is optionally substituted with one, two or three substituents independently selected from the group consisting of halo, $C_{1-6}$ alkyl, cycloalkyl, heteroaryl, $-CN$, $-O-R^{20}$, $-N(R^{20})(R^{22})$, $-C(O)-R^{20}$, $-N(R^{20})-C(O)-OR^{20}$ and $-C(O)-OR^{20}$; and
    wherein said $C_{1-6}$ alkyl or heteroaryl are optionally substituted with one, two or three substituents independently selected from the group consisting of halo, $-CN$, $-O-R^{20}$, $C_{1-6}$ alkyl, aryl, and heteroaryl.

In some embodiments, $R^1$ is phenyl substituted with $-O-CF_3$ or $-CF_3$;
  n is 0; and
  $R^2$ and $R^4$ join together with the atom to which they are attached to form a heterocyclyl or heteroaryl;
    wherein said heterocyclyl or heteroaryl is optionally substituted with one, two or three substituents independently selected from the group consisting of halo, $C_{1-6}$ alkyl, cycloalkyl, heteroaryl, —CN, —C(O)—$R^{20}$, —N($R^{20}$)—C(O)—O$R^{20}$ and —C(O)—O$R^{20}$; and wherein said $C_{1-6}$ alkyl or heteroaryl are optionally substituted with one, two or three substituents independently selected from the group consisting of halo, —CN, —O—$R^{20}$, $C_{1-6}$ alkyl, aryl, and heteroaryl.

In some embodiments, the compound is selected from the group consisting of

| I-5 | 3-cyclopropyl-10-(4-(trifluoromethyl)phenyl)-5,6-dihydrobenzo[f][1,2,4]triazolo[4,3-d][1,4]oxazepine |
| I-6 | 3-methyl-10-(4-(trifluoromethyl)phenyl)-5,6-dihydrobenzo[f]imidazo[1,2- d][1,4]oxazepine |
| I-7 | 3-(pyrimidin-2-yl)-10-(4-(trifluoromethyl)phenyl)-5,6-dihydrobenzo[f]imidazo[1,2- d][1,4]oxazepine |
| I-18 | 3-cyclopropyl-10-(4-(trifluoromethoxy)phenyl)-5,6-dihydrobenzo[f]imidazo[1,2- d][1,4]oxazepine | or a pharmaceutically acceptable salt, stereoisomer, mixture of stereoisomers, or tautomer thereof.

In certain embodiments, the compound of Formula I is represented by Formula IB:

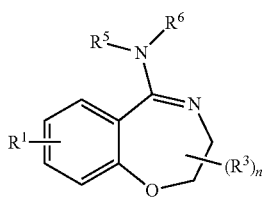

IB wherein:
$R^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, —NO$_2$, —CN, —SF$_5$, —Si(CH$_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(=O)$_2$—$R^{26}$, —S(=O)$_2$—$R^{20}$, —O—S(=O)$_2$—$R^{20}$, —S(=O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
    wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;
n is 0, 1, 2, 3 or 4;
each $R^3$ is independently $C_{1-6}$ alkyl, cycloalkyl, aryl, heteroaryl or heterocyclyl;
  wherein said $C_{1-6}$ alkyl is optionally substituted with one, two or three substituents independently selected from the group consisting of halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
    wherein said $C_{1-6}$ alkyl, aralkyl, cycloalkyl, aryl, heterocyclyl or heteroaryl, are optionally further substituted with one, two or three substituents independently selected from the group consisting of halo, —NO$_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
or two $R^3$ attached to a common carbon atom form an oxo;
or two $R^3$ attached to a common or adjacent carbon atoms form a cycloalkyl or heterocyclyl;
  wherein said cycloalkyl or heterocyclyl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
$R^5$ is hydrogen, $C_{1-6}$ alkyl, cycloalkyl, aryl, heteroaryl or heterocyclyl;
  wherein said $C_{1-6}$ alkyl, cycloalkyl, aryl, heteroaryl or heterocyclyl are optionally substituted with one, two or three substituents independently selected from the group consisting of halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
    wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
    wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —NO$_2$, —N($R^{20}$)($R^{22}$), —C(O)—$R^{20}$, —C(O)—O$R^{20}$;
$R^6$ is $C_{1-6}$ alkyl, cycloalkyl, aryl, heteroaryl or heterocyclyl;
  wherein said $C_{1-6}$ alkyl, cycloalkyl, aryl, heteroaryl or heterocyclyl are optionally substituted with one, two or three substituents independently selected from the group consisting of halo, —NO$_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
    wherein said $C_{1-6}$ alkyl, cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —$N(R^{20})(R^{22})$, —$C(O)$—$R^{20}$, —$C(O)$—$OR^{20}$;

or $R^5$ and $R^6$ can join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —$N(R^{20})(R^{22})$, —$N(R^{20})$—$C(O)$—$R^{20}$, —$N(R^{20})$—$C(O)$—$OR^{20}$ and —$C(O)$—$OR^{20}$; and wherein said $C_{1-6}$ alkyl or heterocyclyl is optionally substituted with one, two or three substituents independently selected from the group consisting of halo, oxo, heteroaryl and —O—$R^{20}$;

$R^{20}$ and $R^{22}$ are in each instance independently selected from the group consisting of hydrogen, $C_{1-6}$ alkyl, cycloalkyl, heterocyclyl, aryl and heteroaryl; and wherein the $C_{1-6}$ alkyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$SO_2R^{26}$, —CN, $C_{1-3}$ alkoxy, aryloxy, —$CF_3$, —$OCF_3$, —$OCH_2CF_3$, —$C(O)$—$NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclyl or heteroaryl which is then optionally substituted with one, two or three substituents independently selected from the group consisting of hydroxyl, halo, $C_{1-4}$ alkyl, aralkyl, aryloxy, aralkyloxy, acylamino, —$NO_2$, —$SO_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, stereoisomer, mixture of stereoisomers, or tautomer thereof.

In some embodiments, $R^1$ is aryl optionally substituted with —O—$R^{20}$ or $C_{1-6}$ alkyl, wherein said $C_{1-6}$ alkyl is optionally substituted with one, two or three halo.

In some embodiments, $R^1$ is aryl optionally substituted with —O—$R^{20}$ or $C_{1-6}$ alkyl, wherein said $C_{1-6}$ alkyl is optionally substituted with one, two or three halo.

In some embodiments, $R^1$ is

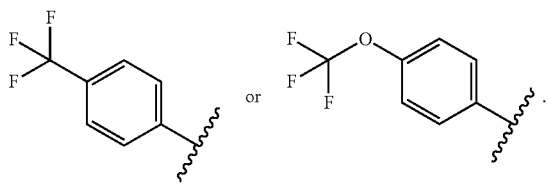 [SMILES: *c1ccc(C(F)(F)F)cc1 ; *c1ccc(OC(F)(F)F)cc1]

In some embodiments, n is 0.
In some embodiments, $R^5$ is hydrogen or $C_{1-6}$ alkyl.

In some embodiments, $R^5$ is hydrogen or methyl.

In some embodiments, $R^6$ is $C_{1-6}$ alkyl, cycloalkyl, aryl, heteroaryl or heterocyclyl;

wherein said $C_{1-6}$ alkyl, heteroaryl or heterocyclyl are optionally substituted with one, two or three substituents independently selected from the group consisting of halo, $C_{1-6}$ alkyl, cycloalkyl, aryl, heteroaryl, —$C(O)$—$R^{20}$, —$C(O)$—$OR^{20}$ and —O—$R^{20}$;

wherein said $C_{1-6}$ alkyl or heteroaryl are optionally further substituted with one, two or three substituents independently selected from the group consisting of halo, $C_{1-6}$ alkyl or heteroaryl; and wherein said $C_{1-6}$ alkyl is optionally further substituted with one, two or three halo.

In some embodiments, $R^6$ is selected from the group consisting of (1-methyl-1H-benzo[d]imidazol-2-yl)methyl, (1-methyl-1H-imidazol-2-yl)methyl, (1-oxo-1-pyrimidin-2-ylmethyl)pyrrolidin-3-yl, (1-oxo-tertbutoxymethyl)pyrrolidin-3-yl, (3-fluoropyridin-2-yl)methyl, (6-(trifluoromethyl)pyridin-2-yl)methyl, 1-(pyrimidin-2-ylmethyl)pyrrolidin-3-yl, 1H-tetrazol-5-yl, 2-(1H-imidazol-1-yl)ethyl, 2-(2-chlorophenoxy)ethyl, 2-(pyridin-2-yloxy)ethyl, 2,2,2-trifluoroethyl, 2-phenoxyethyl, 6-(trifluoromethyl)pyridin-2-yl, benzyl, cyclopropyl, cyclopropylmethyl, phenyl, pyridin-2-yl, pyridin-2-ylmethyl, pyrimidin-2-ylmethyl and pyrrolidin-3-yl.

In some embodiments, $R^5$ and $R^6$ join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —$N(R^{20})(R^{22})$, —$N(R^{20})$—$C(O)$—$R^{20}$, —$N(R^{20})$—$C(O)$—$OR^{20}$ and —$C(O)$—$OR^{20}$; and wherein said $C_{1-6}$ alkyl or heterocyclyl is optionally substituted with one, two or three substituents independently selected from the group consisting of halo, oxo, heteroaryl and —O—$R^{20}$.

In some embodiments, $R^5$ and $R^6$ join together with the atom to which they are attached to form a heterocyclyl;

wherein said heterocyclyl is optionally substituted with one, two or three substituents independently selected from the group consisting of halo, $C_{1-6}$ alkyl, cycloalkyl, heterocyclyl, heteroaryl, oxo, —CN, —O—$R^{20}$, —$N(R^{20})(R^{22})$, —$N(R^{20})$—$C(O)$—$R^{20}$ and —$N(R^{20})$—$C(O)$—$OR^{20}$; and wherein said $C_{1-6}$ alkyl or heterocyclyl is optionally substituted with one, two or three substituents independently selected from the group consisting of halo, oxo and —O—$R^{20}$.

In some embodiments, $R^5$ and $R^6$ join together with the atom to which they are attached to form a heterocyclyl selected from the group consisting of

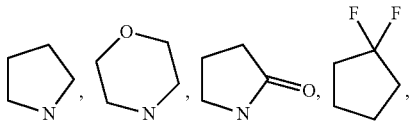

-continued

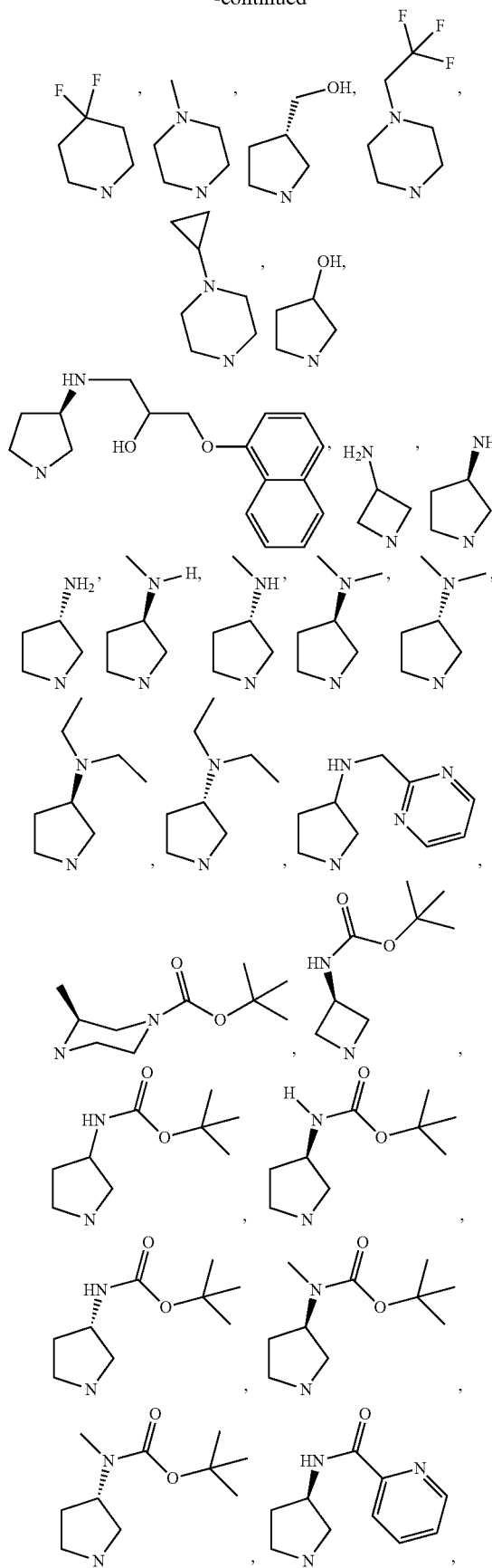

-continued

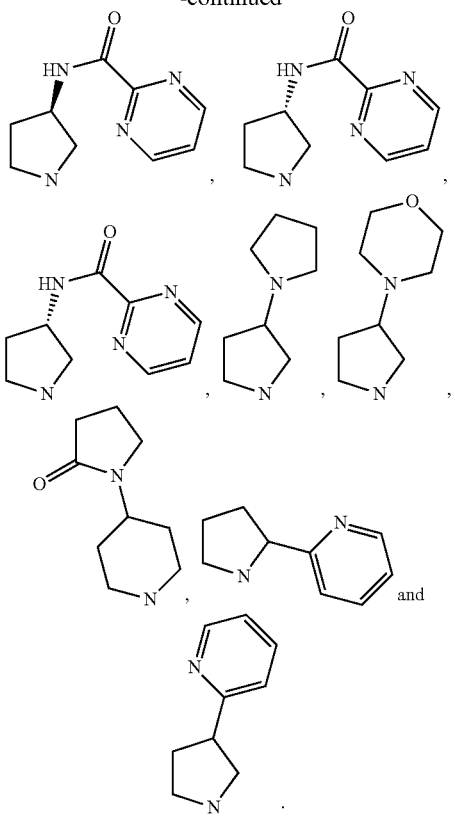

In some embodiments, $R^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, —$NO_2$, —CN, —$SF_5$, —Si$(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), N($R^{20}$)—C(O)—$R^{22}$, —N($R^{20}$)—C(O)—$OR^{22}$, —N($R^{20}$)—S(=O)$_2$—$R^{26}$, —S(=O)$_2$—$R^{20}$, —O—S(=O)$_2$—$R^{20}$, —S(=O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
  wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;
n is 0;
$R^5$ is hydrogen or $C_{1-6}$ alkyl; and
$R^6$ is $C_{1-6}$ alkyl, cycloalkyl, aryl, heteroaryl or heterocyclyl;
  wherein said $C_{1-6}$ alkyl, cycloalkyl, aryl, heteroaryl or heterocyclyl are optionally substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, C(O)—$OR^{20}$, —C(O)—N($R^{20}$)($R^{22}$), —CN and —O—$R^{20}$;
  wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —$N(R^{20})(R^{22})$, —$C(O)$—$R^{20}$, —$C(O)$—$OR^{20}$;

or $R^5$ and $R^6$ can join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —$N(R^{20})(R^{22})$, —$N(R^{20})$—$C(O)$—$R^{20}$, —$N(R^{20})$—$C(O)$—$OR^{20}$ and —$C(O)$—$OR^{20}$; and wherein said $C_{1-6}$ alkyl or heterocyclyl is optionally substituted with one, two or three substituents independently selected from the group consisting of halo, oxo, heteroaryl and —O—$R^{20}$.

In some embodiments, $R^1$ is aryl;

wherein said aryl is optionally substituted with one, two or three substituents independently selected from the group consisting of halo, —$NO_2$, —CN, —$SF_5$, —$Si(CH_3)_3$, —O—$R^{20}$, —S—$R^{20}$, —$C(O)$—$R^{20}$, —$C(O)$—$OR^{20}$, —$N(R^{20})(R^{22})$, —$C(O)$—$N(R^{20})(R^{22})$, —$N(R^{20})$—$C(O)$—$R^{22}$, —$N(R^{20})$—$C(O)$—$OR^{22}$, —$N(R^{20})$—$S(=O)_2$—$R^{26}$, —$S(=O)_2$—$R^{20}$, —O—$S(=O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —$N(R^{20})(R^{22})$, —$C(O)$—$R^{20}$, —$C(O)$—$OR^{20}$, —$C(O)$—$N(R^{20})(R^{22})$, —CN and —O—R;

n is 0;

$R^5$ is hydrogen or $C_{1-6}$ alkyl; and $R^6$ is $C_{1-6}$ alkyl, cycloalkyl, aryl, heteroaryl or heterocyclyl;

wherein said $C_{1-6}$ alkyl, cycloalkyl, aryl, heteroaryl or heterocyclyl are optionally substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —$N(R^{20})(R^{22})$, —$C(O)$—$R^{20}$, —$C(O)$—$OR^{20}$;

or $R^5$ and $R^6$ can join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —$N(R^{20})(R^{22})$, —$N(R^{20})$—$C(O)$—$R^{20}$, —$N(R^{20})$—$C(O)$—$OR^{20}$ and —$C(O)$—$OR^{20}$; and wherein said $C_{1-6}$ alkyl or heterocyclyl is optionally substituted with one, two or three substituents independently selected from the group consisting of halo, oxo, heteroaryl and —O—$R^{20}$.

In some embodiments, $R^1$ is aryl optionally substituted with —O—$R^{20}$ or $C_{1-6}$ alkyl; and wherein said $C_{1-6}$ alkyl is optionally substituted with one, two or three halo;

n is 0;

$R^5$ is hydrogen or $C_{1-15}$ alkyl; and $R^6$ is $C_{1-6}$ alkyl, cycloalkyl, aryl, heteroaryl or heterocyclyl;

wherein said $C_{1-6}$ alkyl, cycloalkyl, aryl, heteroaryl or heterocyclyl are optionally substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —$N(R^{20})(R^{22})$, —$C(O)$—$R^{20}$, —$C(O)$—$OR^{20}$;

or $R^5$ and $R^6$ can join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —$N(R^{20})(R^{22})$, —$N(R^{20})$—$C(O)$—$R^{20}$, —$N(R^{20})$—$C(O)$—$OR^{20}$ and —$C(O)$—$OR^{20}$; and wherein said $C_{1-6}$ alkyl or heterocyclyl is optionally substituted with one, two or three substituents independently selected from the group consisting of halo, oxo, heteroaryl and —O—$R^{20}$.

In some embodiments, $R^1$ is phenyl substituted with —O—$CF_3$ or —$CF_3$;

n is 0;

$R^5$ is hydrogen or $C_{1-15}$ alkyl; and $R^6$ is $C_{1-6}$ alkyl, cycloalkyl, aryl, heteroaryl or heterocyclyl;

wherein said $C_{1-6}$ alkyl, cycloalkyl, aryl, heteroaryl or heterocyclyl are optionally substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —N($R^{20}$)($R^{22}$), —C(O)—$R^{20}$, —C(O)—O$R^{20}$;

or $R^5$ and $R^6$ can join together with the atom to which they are attached to form a heterocyclyl or heteroaryl;

wherein said heterocyclyl or heteroaryl is optionally substituted with one, two or three substituents independently selected from the group consisting of halo, $C_{1-6}$ alkyl, cycloalkyl, heterocyclyl, aryl, heteroaryl, oxo, —CN, —O—$R^{20}$, —N($R^{20}$)($R^{22}$), —N($R^{20}$)—C(O)—$R^{20}$, —N($R^{20}$)—C(O)—O$R^{20}$ and —C(O)—O$R^{20}$; and wherein said $C_{1-6}$ alkyl or heterocyclyl is optionally substituted with one, two or three substituents independently selected from the group consisting of halo, oxo, heteroaryl and —O—$R^{20}$.

In some embodiments, the compound is selected from the group consisting of:

| | |
|---|---|
| II-1 | 5-morpholino-7-(4-(trifluoromethyl)phenyl)-2,3-dihydrobenzo[f][1,4]oxazepine |
| II-2 | N-benzyl-7-(4-(trifluoromethyl)phenyl)-2,3-dihydrobenzo[f][1,4]oxazepin-5-amine |
| II-3 | 5-(pyrrolidin-1-yl)-7-(4-(trifluoromethyl)phenyl)-2,3-dihydrobenzo[f][1,4]oxazepine |
| II-4 | N-cyclopropyl-7-(4-(trifluoromethyl)phenyl)-2,3-dihydrobenzo[f][1,4]oxazepin-5-amine |
| II-5 | N-benzyl-N-methyl-7-(4-(trifluoromethyl)phenyl)-2,3-dihydrobenzo[f][1,4]oxazepin-5-amine |
| II-9 | N-((3-fluoropyridin-2-yl)methyl)-7-(4-(trifluoromethyl)phenyl)-2,3-dihydrobenzo[f][1,4]oxazepin-5-amine |
| II-10 | N-(pyridin-2-ylmethyl)-7-(4-(trifluoromethyl)phenyl)-2,3-dihydrobenzo[f][1,4]oxazepin-5-amine |
| II-11 | N-(cyclopropylmethyl)-7-(4-(trifluoromethyl)phenyl)-2,3-dihydrobenzo[f][1,4]oxazepin-5-amine |
| II-13 | (S)-tert-butyl 1-(7-(4-(trifluoromethyl)phenyl)-2,3-dihydrobenzo[f][1,4]oxazepin-5-yl)pyrrolidin-3-ylcarbamate |
| II-14 | N-(2-(1H-imidazol-1-yl)ethyl)-7-(4-(trifluoromethyl)phenyl)-2,3-dihydrobenzo[f][1,4]oxazepin-5-amine |
| II-15 | (S)-N,N-dimethyl-1-(7-(4-(trifluoromethyl)phenyl)-2,3-dihydrobenzo[f][1,4]oxazepin-5-yl)pyrrolidin-3-amine |
| II-19 | N-(pyridin-2-yl)-7-(4-(trifluoromethyl)phenyl)-2,3-dihydrobenzo[f][1,4]oxazepin-5-amine |
| II-20 | N-(2-(pyridin-2-yloxy)ethyl)-7-(4-(trifluoromethyl)phenyl)-2,3-dihydrobenzo[f][1,4]oxazepin-5-amine |
| II-22 | N-(2-phenoxyethyl)-7-(4-(trifluoromethyl)phenyl)-2,3-dihydrobenzo[f][1,4]oxazepin-5-amine |
| II-24 | N-(2-(2-chlorophenoxy)ethyl)-7-(4-(trifluoromethyl)phenyl)-2,3-dihydrobenzo[f][1,4]oxazepin-5-amine |
| II-25 | 7-(4-(trifluoromethyl)phenyl)-N-((6-(trifluoromethyl)pyridin-2-yl)methyl)-2,3-dihydrobenzo[f][1,4]oxazepin-5-amine |
| II-31 | 5-(4-cyclopropylpiperazin-1-yl)-7-(4-(trifluoromethyl)phenyl)-2,3-dihydrobenzo[f][1,4]oxazepine |
| II-32 | N-phenyl-7-(4-(trifluoromethyl)phenyl)-2,3-dihydrobenzo[f][1,4]oxazepin-5-amine |
| II-33 | N-((1-methyl-1H-benzo[d]imidazol-2-yl)methyl)-7-(4-(trifluoromethyl)phenyl)-2,3-dihydrobenzo[f][1,4]oxazepin-5-amine |
| II-37 | N-(pyrimidin-2-ylmethyl)-1-(7-(4-(trifluoromethyl)phenyl)-2,3-dihydrobenzo[f][1,4]oxazepin-5-yl)pyrrolidin-3-amine |
| II-38 | (R)-tert-butyl methyl(1-(7-(4-(trifluoromethyl)phenyl)-2,3-dihydrobenzo[f][1,4]oxazepin-5-yl)pyrrolidin-3-yl)carbamate |
| II-39 | (R)-N-methyl-1-(7-(4-(trifluoromethyl)phenyl)-2,3-dihydrobenzo[f][1,4]oxazepin-5-yl)pyrrolidin-3-amine |
| II-40 | (S)-tert-butylmethyl(1-(7-(4-(trifluoromethyl)phenyl)-2,3-dihydrobenzo[f][1,4]oxazepin-5-yl)pyrrolidin-3-yl)carbamate |
| II-43 | (S)-tert-butyl 3-(7-(4-(trifluoromethyl)phenyl)-2,3-dihydrobenzo[f][1,4]oxazepin-5-ylamino)pyrrolidine-1-carboxylate |
| II-47 | (R)-N-(1-(7-(4-(trifluoromethyl)phenyl)-2,3-dihydrobenzo[f][1,4]oxazepin-5-yl)pyrrolidin-3-yl)picolinamide |
| II-48 | (S)-N,N-diethyl-1-(7-(4-(trifluoromethyl)phenyl)-2,3-dihydrobenzo[f][1,4]oxazepin-5-yl)pyrrolidin-3-amine |
| II-50 | (R)-tert-butyl 1-(7-(4-(trifluoromethyl)phenyl)-2,3-dihydrobenzo[f][1,4]oxazepin-5-yl)pyrrolidin-3-ylcarbamate |
| II-51 | (R)-N,N-dimethyl-1-(7-(4-(trifluoromethyl)phenyl)-2,3-dihydrobenzo[f][1,4]oxazepin-5-yl)pyrrolidin-3-amine |
| II-54 | N-phenyl-7-(4-(trifluoromethyl)phenyl)-2,3-dihydrobenzo[f][1,4]oxazepin-5-amine |
| II-55 | 5-(3-morpholinopyrrolidin-1-yl)-7-(4-(trifluoromethyl)phenyl)-2,3-dihydrobenzo[f][1,4]oxazepine |
| II-56 | (S)-1-(7-(4-(trifluoromethyl)phenyl)-2,3-dihydrobenzo[f][1,4]oxazepin-5-yl)pyrrolidin-3-amine |
| II-57 | tert-butyl 1-(7-(4-(trifluoromethyl)phenyl)-2,3-dihydrobenzo[f][1,4]oxazepin-5-yl)pyrrolidin-3-ylcarbamate |

-continued

| | |
|---|---|
| II-58 | 5-(2-(pyridin-2-yl)pyrrolidin-1-yl)-7-(4-(trifluoromethyl)phenyl)-2,3-dihydrobenzo[f][1,4]oxazepine |
| II-60 | 5-(3-(pyridin-2-yl)pyrrolidin-1-yl)-7-(4-(trifluoromethyl)phenyl)-2,3-dihydrobenzo[f][1,4]oxazepine |
| II-61 | 1-(naphthalen-1-yloxy)-3-((R)-1-(7-(4-(trifluoromethyl)phenyl)-2,3-dihydrobenzo[f][1,4]oxazepin-5-yl)pyrrolidin-3-ylamino)propan-2-ol |
| II-62 | tert-butyl 3-(7-(4-(trifluoromethyl)phenyl)-2,3-dihydrobenzo[f][1,4]oxazepin-5-ylamino)pyrrolidine-1-carboxylate |
| II-63 | (R)-tert-butyl 3-(7-(4-(trifluoromethyl)phenyl)-2,3-dihydrobenzo[f][1,4]oxazepin-5-ylamino)pyrrolidine-1-carboxylate | or a pharmaceutically acceptable salt, stereoisomer, mixture of stereoisomers, or tautomer thereof.

4. Alternative Embodiments

In alternative embodiments, the compound of Formula I is represented by Formula VII:

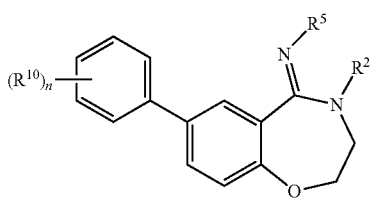

VII wherein:
  n is 0, 1, 2 or 3:
    each $R^{10}$ is independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $N(R^{20})-C(O)-R^{22}$, $-N(R^{20})-C(O)-OR^{22}$, $-N(R^{20})-S(=O)_2-R^{26}$, $-S(=O)_2-R^{20}$, $-S(=O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and
      wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;
  $R^2$ is hydrogen, $C_{1-15}$ alkyl, $-C(O)-R^{20}$, $-C(O)-OR^{26}$, $-C(O)-N(R^{26})(R^{28})$, $-N(R^{20})-S(=O)_2-R^{20}$, cycloalkyl, aryl, heteroaryl or heterocyclyl;
    wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, $-NO_2$, cycloalkyl, aryl, heterocyclyl, heteroaryl, $-N(R^{20})(R^{22})$, $-C(O)-OR^{20}$, $-C(O)-OR^{20}$, $-C(O)-N(R^{20})(R^{22})$, $-CN$, oxo and $-O-R^{20}$;
      wherein said $C_{1-6}$ alkyl, cycloalkyl, aryl, heterocyclyl or heteroaryl are optionally further substituted with one, two or three substituents independently selected from the group consisting of halo, $-NO_2$, $C_{1-6}$ alkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and
        wherein said $C_{1-6}$ alkyl, cycloalkyl, aryl, heterocyclyl or heteroaryl are optionally further substituted with one, two or three substituents independently selected from the group consisting of halo, $-NO_2$, $-CF_3$, $-N(R^{20})(R^{22})$, $-C(O)-R^{20}$, $-C(O)-OR^{20}$, $-C(O)-N(R^{20})(R^{22})$, $-CN$, $-S(O)_2-R^{20}$ and $-O-R^{20}$;
  $R^5$ is hydrogen, $C_{1-15}$ alkyl, $C_{1-4}$ alkoxy, $-C(O)-O-R^{26}$, $-C(O)-N(R^{26})(R^{28})$, $-N(R^{20})-S(=O)_2-R^{20}$, cycloalkyl, aryl, heteroaryl or heterocyclyl;
    wherein said $C_{1-15}$ alkyl is optionally substituted with one, two or three substituents independently selected from the group consisting of halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;
      wherein said cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and
        wherein said $C_{1-6}$ alkyl, aralkyl, cycloalkyl, aryl, heterocyclyl or heteroaryl are optionally further substituted with one, two or three substituents independently selected from the group consisting of hydroxyl, halo, $-NO_2$, $-N(R^{20})(R^{22})$, $-C(O)-R^{20}$, $-C(O)-OR^{20}$, $-C(O)-N(R^{20})(R^{22})$, $-CN$ and $-O-R^{20}$;
  or $R^2$ and $R^5$ can join together with the atom to which they are attached to form a heterocyclyl or heteroaryl;
    wherein said heterocyclyl or heteroaryl is optionally substituted with one, two or three substituents independently selected from the group consisting of $C_{1-15}$ alkyl, cycloalkyl, heteroaryl, $-O-R^{20}$, $-N(R^{20})(R^{22})$, $-N(R^{20})-C(O)-OR^{20}$ and $-C(O)-OR^{20}$; and
      wherein said $C_{1-15}$ alkyl is optionally substituted with one, two or three substituents independently selected from the group consisting of halo and heteroaryl;
  $R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and
    wherein the $C_{1-15}$ alkyl, $C_{2-15}$ alkenyl, $C_{2-15}$ alkynyl, cycloalkyl, heterocyclyl, aryl, and heteroaryl are optionally substituted with one, two or three substituents independently selected from the group consisting of hydroxyl, halo, $C_{1-4}$ alkyl, acylamino, $-NO_2$, $-SO_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —$SO_2R^{26}$, —CN, $C_{1-3}$ alkoxy, —$CF_3$, —$OCF_3$, aryl, heteroaryl and cycloalkyl;

$R^{25}$ is in each instance independently a covalent bond or $C_{1-3}$ alkylene optionally substituted with one or two $C_{1-3}$ alkyl groups; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof In some embodiments, when $R^2$ and $R^5$ join together with the atom to which they are attached to form an optionally substituted imidazolyl, the imidazolyl it is not directly substituted with an optionally substituted triazolyl, or $R^1$ is not optionally substituted pyrazolyl, 2-pyridinonyl or 2-fluoropyridinyl.

In some embodiments, $R^2$ and $R^5$ are joined together with the atom to which they are attached to form a heterocyclyl or heteroaryl;

wherein said heterocyclyl or heteroaryl is optionally substituted with one, two or three substituents independently selected from the group consisting of $C_{1-15}$ alkyl, cycloalkyl and heteroaryl.

In some embodiments, $R^2$ and $R^5$ are joined together with the atom to which they are attached to form

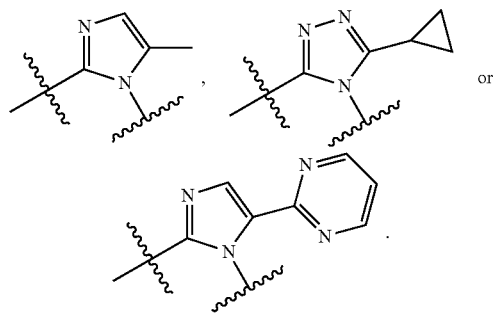

In some embodiments, $R^{10}$ is 4-trifluoromethyl.

In some embodiments, the compound is selected from the group consisting of 3-cyclopropyl-10-(4-(trifluoromethyl)phenyl)-5,6-dihydrobenzo[f][1,2,4]triazolo[4,3-d][1,4]oxazepine;

3-methyl-10-(4-(trifluoromethyl)phenyl)-5,6-dihydrobenzo[f]imidazo[1,2-d][1,4]oxazepine; and 3-(pyrimidin-2-yl)-10-(4-(trifluoromethyl)phenyl)-5,6-dihydrobenzo[f]imidazo[1,2-d][1,4]oxazepine;

or a pharmaceutically acceptable salt, ester, hydrate, solvate, stereoisomer, mixture of stereoisomers, tautomer, polymorph and/or prodrug thereof.

5. Further Embodiments

In some embodiments, the compounds provided by the present disclosure are effective in the treatment of conditions or diseases known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the disclosure may also possess a sufficient activity in modulating neuronal sodium channels, i.e., $Na_v$ 1.1, 1.2, 1.3, 1.5, 1.7, and/or 1.8, and may have appropriate pharmacokinetic properties such that they may be active with regard to the central and/or peripheral nervous system. Consequently, some compounds of the disclosure may also be of use in the treatment of epilepsy or pain or itching or heartache of a neuropathic origin.

In one embodiment, this disclosure provides a method of treating a disease state in a mammal that is alleviable by treatment with an agent capable of reducing late sodium current, comprising administering to a mammal in need thereof a therapeutically effective dose of a compound of Formula I, IA, IB or VII or other formulas or compounds disclosed herein. In another embodiment, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication.

In another embodiment, the disease state is diabetes or diabetic peripheral neuropathy. In a further embodiment, the disease state results in one or more of neuropathic pain, epilepsy, heartache, seizures, or paralysis.

In one embodiment, this disclosure provides a method of treating diabetes in a mammal, comprising administering to a mammal in need thereof a therapeutically effective dose of a compound of Formula I, IA, IB or VII or other formulas or compounds disclosed herein. Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and/or a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

It has been suggested that ranolazine (RANEXA®, a selective inhibitor of INaL) may be an antidiabetic agent that causes β-cell preservation and enhances insulin secretion in a glucose-dependent manner in diabetic mice (see, Y. Ning et al. J Pharmacol Exp Ther. 2011, 337(1), 50-8). Therefore it is contemplated that the compounds of Formula I, IA, IB or VII or other formulas or compounds disclosed herein can be used as antidiabetic agents for the treatment of diabetes.

6. Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving. In some embodiments, the late sodium channel blockers of the disclosure are co-administered with ranolazine (RANEXA®).

Anti-anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein IIb/IIIa inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound as disclosed herein (e.g., Formula I, IA, IB or VII) in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein (e.g., Formula I, IA, IB or VII).

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef®), cephalexin (Keflex®), cephradine (Velosef®), cefaclor (Ceclor®), cefuroxime axtel (Ceftin®), cefprozil (Cefzil®), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the $Na_v$ 1.7 and 1.8 sodium channels, combination with analgesics are particularly envisioned. See U.S. Patent Application Publication 20090203707.

Antidepressant and Anti-anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®); escitalopram (Lexapro®, Cipralex®); fluoxetine (Prozac®, Sarafem®, Fluctin®, Fontex®, Prodep®, Fludep®, Lovan®); venlafaxine (Effexor® XR, Efexor); citalopram (Celexa®, Cipramil®, Talohexane®); paroxetine (Paxil®, Seroxat®, Aropax®); trazodone (Desyrel®); amitriptyline (Elavil®); and bupropion (Wellbutrin®, Zyban®).

Accordingly, one aspect of the disclosure provides for a composition comprising the late sodium channel blockers of the disclosure and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic affect.

7. Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, IA, IB or VII or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I are typically prepared by first providing the molecular core 1-1 and then attaching the desired —R$^1$ substituent using suitable coupling conditions (e.g., Suzuki coupling). This process is show below in Scheme 1 for the synthesis of a compound of Formula I.

Scheme 1

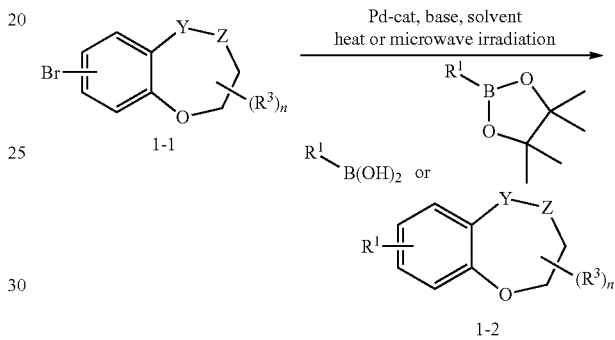

In general, a halogenated compound of formula 1-1, in this case a brominated compound, is reacted with an appropriately substituted boronic acid derivative of formula R$^1$—B(OH)$_2$ or a boronic ester thereof, in an inert solvent, for example aqueous N,N-dimethylformamide, in the presence of a mild base, for example potassium carbonate or sodium bicarbonate. The reaction is typically conducted in the presence of a metal catalyst with an appropriate ligand, for example dichlorobis(triphenylphosphine) palladium(II), at a temperature of about 120-170° C., for about 10 minutes to about 1 hour or at a lower temperature, ie., 90-110° C. for 2 to 5 days. When the reaction is substantially complete, the product of Formula I is isolated by conventional means.

Optional Core Synthesis

In certain embodiments, the core may be synthesized before or after addition of the —R$^1$ substitutent (Scheme 2). For example, such an alternative route for the synthesis of compounds of formula 2-3 and 2-4 (i.e., Formulas IA and IB, respectively) is shown in Scheme 2, below.

Scheme 2

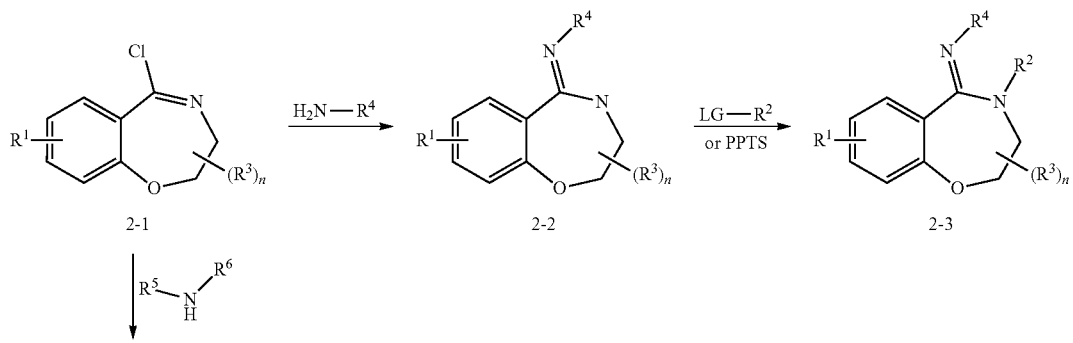

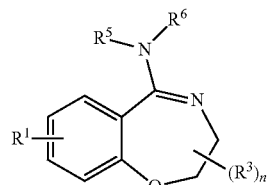

2-4

In one embodiment, compounds of Formula 2-2 can be provided from the amination of compounds of Formula 2-1 with a amine of formula $NH_2$—$R^4$.

The $R^2$ moiety may be coupled to compounds of Formula 2-2 under substitution reaction conditions with an appropriate reagent of formula LG-$R^2$ (where LG is a leaving group such as a halo, hydroxyl, alkoxy, or the like) to afford compounds of Formula 2-3. Typical substitution reaction conditions include the presence of a base, such as ssium carbonate, sodium bicarbonate, triethylamine, and the like, in a polar aprotic solvent, such as N,N-dimethylformamide, and optionally an elevated temperature of about 100-150° C. or in a microwave.

In one embodiment, compounds of Formula 2-4 can be provided from the amination of compounds of Formula 2-1 with a amine of formula $NH(R^5R^6)$.

It will also be appreciated that the addition of any substituent may result in the production of a number of isomeric products any or all of which may be isolated and purified using conventional techniques.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
|---|---|
| ° C. | Degree Celcius |
| anal | Analytical |
| ATP | Adenosine-5'-triphosphate |
| ATX II | Anemonia sulcata toxin |
| ACN | Acetonitrile |
| CHO | Chinese hamster ovary |
| d | Doublet |
| dd | Doublet of doublets |
| DIPEA | N,N-diisopropylethylamine |
| DMF | Dimethylformamide |
| DMSO | Dimethylsulfoxide |
| ECF | Extracellular fluid |
| EDTA | Ethylenediaminetetraacetic acid |
| EGTA | Ethylene glycol tetraacetic acid |
| g | Grams |
| HEPES | (4-(2-Hydroxyethyl)-1-piperazineethanesulfonic acid) |
| hERG | human Ether-à-go-go Related Gene |
| HPLC | High-performance liquid chromatography |
| h | Hours |
| Hz | Hertz |
| $IC_{50}$ | The half maximal inhibitory concentration |
| IMR-32 | Human neuroblastoma cell line |
| J | Coupling constant |
| Kg | Kilogram |
| kHz | Kilohertz |
| M | Molar |
| m | Multiplet |
| m/z | mass-to-charge ratio |
| M+ | Mass peak |
| M + H | Mass peak plus hydrogen |
| mg | Milligram |
| MHz | Megahertz |
| min/m | Minute |
| ml/mL | Milliliter |
| mM | Millimolar |
| mmol | Millimole |
| nmol | Nanomole |
| nM | Nanomolar |
| mOsmol | Milliosmole |
| MS | Mass spectroscopy |
| ms | Millisecond |
| mV | Millivolt |
| mw | Microwave |
| mol | Mole |
| NMR | Nuclear magnetic resonance |
| pA | Picoamps |
| PPTS | Pyridinium p-toluenesulfonate |
| q.s. | Quantity sufficient to achieve a stated function |
| Rf | Retention factor |
| s | Second |
| s | Singlet |
| SEM | Standard error of the mean |
| TB | Tonic Block |
| TEA | Triethylamine |
| TFA | Trifluoroacetic acid |
| THF | Tetrahydrofuran |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |

EXAMPLES

Example 1

10-(4-(trifluoromethyl)phenyl)-5,6-dihydrobenzo[f]imidazo[1,2-d][1,4]oxazepine (Compound I-1)

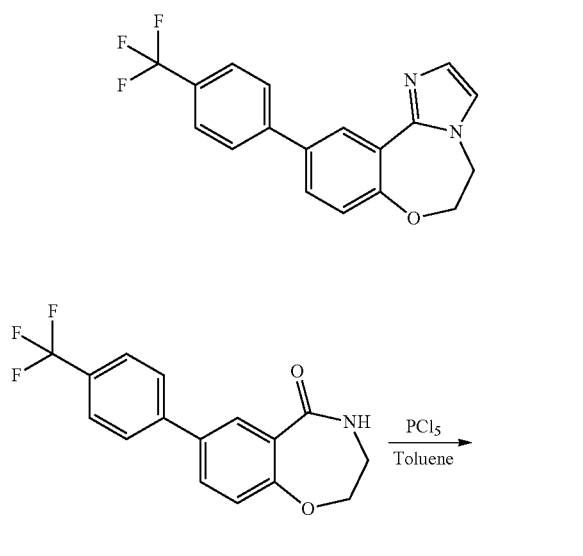

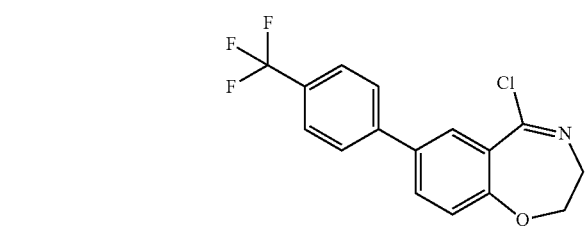

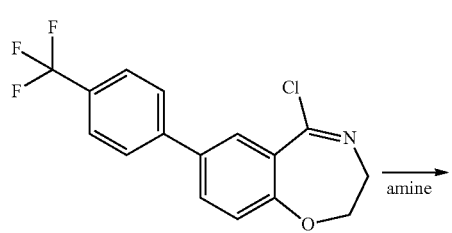

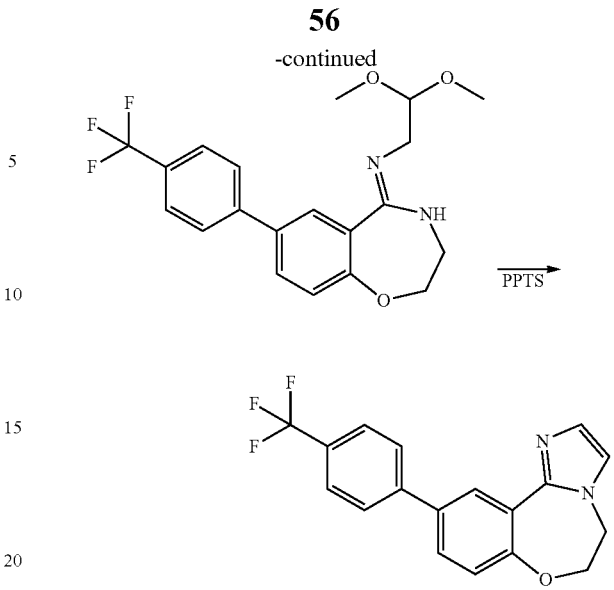

A solution of 7-(4-(trifluoromethyl)phenyl)-3,4-dihydrobenzo[f][1,4]oxazepin-5(2H)-one (3.6 g, 11.7 mmol) and phosphorous pentachloride (2.56 g, 12.3 mmol) in toluene (80 mL) was refluxed for 2 hours. The reaction mixture was concentrated to yield 5-chloro-7-(4-(trifluoromethyl)phenyl)-2,3-dihydrobenzo[f][1,4]oxazepine and used in subsequent steps without further purification.

A solution of 5-chloro-7-(4-(trifluoromethyl)phenyl)-2,3-dihydrobenzo[f][1,4]oxazepine (11.7 mmol) in 2,2-dimethoxyethanamine (20 mL) was heated at n 100° C. for 1 hour. The reaction mixture was concentrated to give (Z)-2,2-dimethoxy-N-(7-(4-(trifluoromethyl)phenyl)-3,4-dihydrobenzo[f][1,4]oxazepin-5(2H)-ylidene)ethanamine as an oil. The crude material was dissolved in toluene (80 mL) and PPTS (6.0 g) was added and the mixture was refluxed for 5 h. The reaction mixture partitioned between ethyl acetate and brine and filtered through celite. The organic layer was dried with sodium sulfate and concentrated before being purified by silica gel chromatography (Rf=0.15 in 2:1 hexanes/ethyl acetate) to give 10-(4-(trifluoromethyl)phenyl)-5,6-dihydrobenzo[f]imidazo[1,2-d][1,4]oxazepine as a white solid (2.3 g, 60% over three steps). $C_{18}H_{13}F_3N_2O \times$ TFA. 331.1 (M+1). $^1$H NMR (DMSO) δ 8.53 (d, J=2.0 Hz, 1H), 7.99 (d, J=8.0 Hz, 2H), 7.91 (dd, J=8.0, 2.0 Hz, 1H), 7.87 (d, J=8.0 Hz, 2H), 7.77 (d, J=12.0 Hz, 2H), 7.30 (d, J=8.8 Hz, 1H), 4.65 (m, 4H). $^{19}$F NMR (DMSO) δ -59.21 (s, 3F).

Example 2

10-(4-(trifluoromethoxy)phenyl)-5,6-dihydrobenzo[f]imidazo[1,2-d][1,4]oxazepine (Compound I-2)

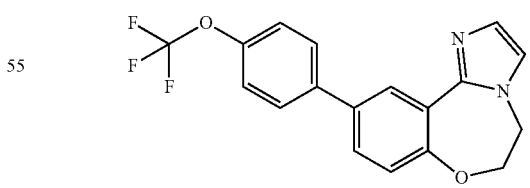

Compound I-2 was prepared according to the Examples disclosed herein using the appropriate starting materials. $C_{18}H_{13}F_3N_2O_2 \times$ TFA. 347.1 (M+1). $^1$H NMR (DMSO) δ 8.45 (d, 2.0 Hz, 1H), 7.86 (m, 3H), 7.76 (d, J=12.0 Hz, 2H), 7.51 (d, J=8.0 Hz, 2H), 7.27 (d, J=8.0 Hz, 1H), 4.65 (m, 4H). $^{19}$F NMR (DMSO) δ -57.30 (s, 3F).

Example 3

10-(4-(trifluoromethyl)phenyl)-5,6-dihydrobenzo[f][1,2,4]triazolo[4,3-d][1,4]oxazepine (Compound I-3)

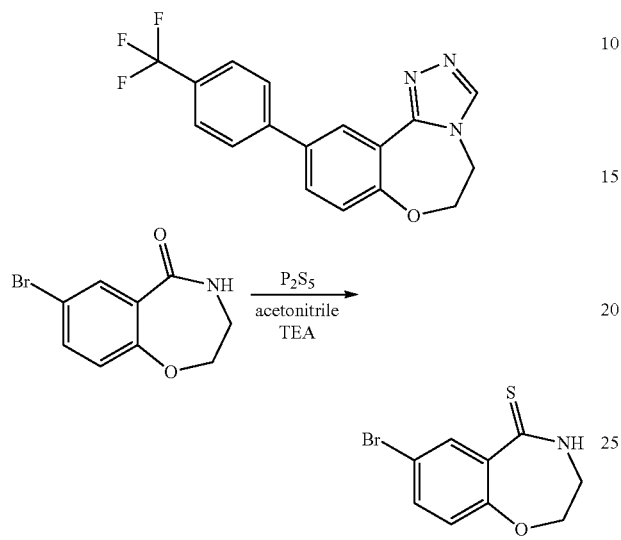

A solution of 7-bromo-3,4-dihydrobenzo[f][1,4]oxazepin-5(2H)-one (2 g, 8.3 mmol) $P_2S_5$ (4.4 g, 10.0 mmol) acetonitrile (40 mL) and triethylamine (20 mL) was refluxed for 4 h. The mixture was concentrated and dissolved in dichloromethane before being washed three times with water. The organic layer was dried with sodium sulfate and concentrated before being purified by silica gel chromatography (Rf=0.35 in 2:1 hexanes/ethyl acetate) to give 7-bromo-3,4-dihydrobenzo[f][1,4]oxazepine-5(2H)-thione as yellow powder (1.3 g, 61%).

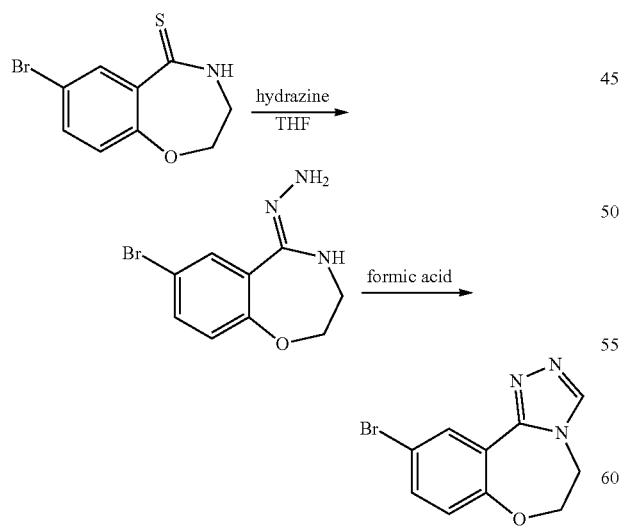

A solution of 7-bromo-3,4-dihydrobenzo[f][1,4]oxazepine-5(2H)-thione (500 mg, 1.94 mmol), anhydrous hydrazine (0.3 mL) and THF was refluxed for 1 h. The reaction was concentrated and the crude hydrazonamide was taken on without further purification. A solution of 7-bromo-5-hydrazono-2,3,4,5-tetrahydrobenzo[f][1,4]oxazepine in formic acid was refluxed for 1 h. The mixture was concentrated and subjected to typical Suzuki reaction conditions followed by preparative HPLC to give Compound I-3. $C_{17}H_{12}F_3N_3O$. 332.1 (M+1).

Example 4

3-cyclopropyl-10-(4-(trifluoromethyl)phenyl)-5,6-dihydrobenzo[f][1,2,4]triazolo[4,3-d][1,4]oxazepine (Compound I-5)

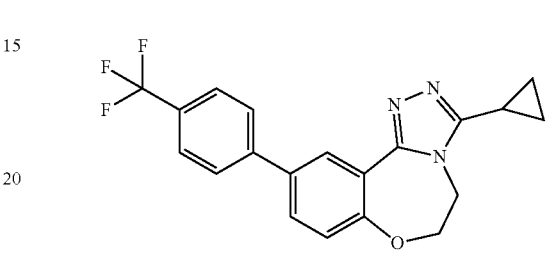

Compound I-5 was prepared according to the Examples disclosed herein using the appropriate starting materials. $C_{20}H_{16}F_3N_3O$. 372.1 (M+1).

Example 5

3-methyl-10-(4-(trifluoromethyl)phenyl)-5,6-dihydrobenzo[f]imidazo[1,2-d][1,4]oxazepine (Compound I-6)

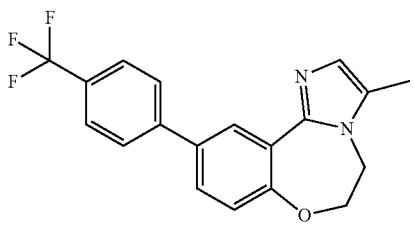 [SMILES: Cc1cnc2n1CCOc1ccc(-c3ccc(C(F)(F)F)cc3)cc1-2]

Compound I-6 was prepared according to the Examples disclosed herein using the appropriate starting materials. $C_{19}H_{15}F_3N_2O$. 345.1 (M+1).

Example 6

3-(pyrimidin-2-yl)-10-(4-(trifluoromethyl)phenyl)-5,6-dihydrobenzo[f]imidazo[1,2-d][1,4]oxazepine (Compound I-7)

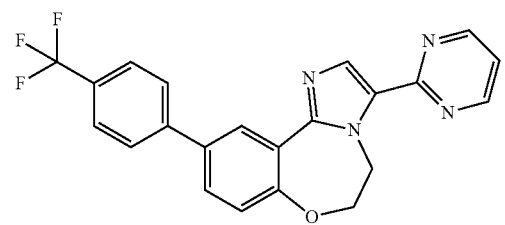 [SMILES: FC(F)(F)c1ccc(-c2ccc3c(c2)-c2ncc(-c4ncccn4)n2CCO3)cc1]

Compound I-7 was prepared according to the Examples disclosed herein using the appropriate starting materials. $C_{22}H_{15}F_3N_4O$. 409.1 (M+1).

Example 7

3-benzyl-10-(4-(trifluoromethyl)phenyl)-5,6-dihydrobenzo[f]imidazo[1,2-d][1,4]oxazepine (Compound I-11)

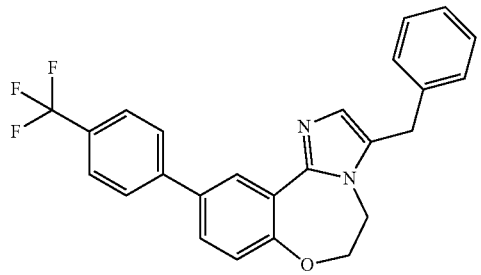 [SMILES: FC(F)(F)c1ccc(-c2ccc3c(c2)-c2ncc(Cc4ccccc4)n2CCO3)cc1]

Compound I-11 was prepared according to the Examples disclosed herein using the appropriate starting materials. $C_{25}H_{19}F_3N_2O$. 421.1 (M+1).

Example 8

2-chloro-3-methyl-10-(4-(trifluoromethyl)phenyl)-5,6-dihydrobenzo[f]imidazo[1,2-d][1,4]oxazepine (Compound I-14)

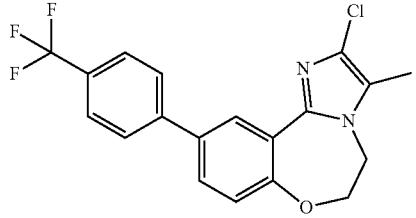 [SMILES: Cc1c(Cl)nc2n1CCOc1ccc(-c3ccc(C(F)(F)F)cc3)cc1-2]

Compound I-14 was prepared according to the Examples disclosed herein using the appropriate starting materials. $C_{19}H_{14}ClF_3N_2O$. 379.4 (M+1).

Example 9

1-(10-(4-(trifluoromethyl)phenyl)-5,6-dihydrobenzo[f]imidazo[1,2-d][1,4]oxazepin-3-yl)ethanone (Compound I-15)

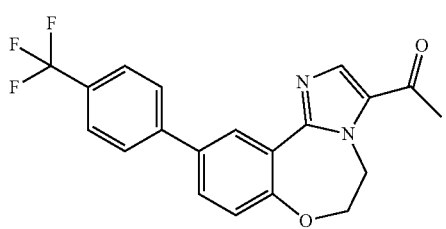 [SMILES: CC(=O)c1cnc2n1CCOc1ccc(-c3ccc(C(F)(F)F)cc3)cc1-2]

Compound I-15 was prepared according to the Examples disclosed herein using the appropriate starting materials. $C_{20}H_{15}F_3N_2O$. 373.1 (M+1).

Example 10

3-methyl-10-(4-(trifluoromethoxy)phenyl)-5,6-dihydrobenzo[f]imidazo[1,2-d][1,4]oxazepine (Compound I-17)

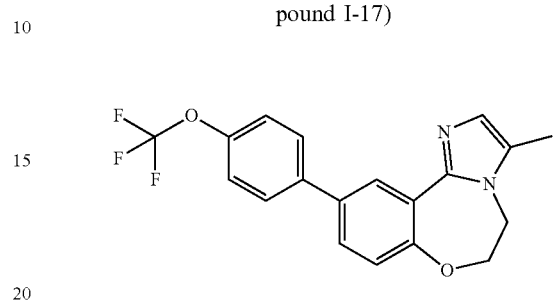

Compound I-17 was prepared according to the Examples disclosed herein using the appropriate starting materials. $C_{19}H_{15}F_3N_2O_2$. 361.1 (M+1).

Example 11

3-cyclopropyl-10-(4-(trifluoromethoxy)phenyl)-5,6-dihydrobenzo[f]imidazo[1,2-d][1,4]oxazepine (Compound I-18)

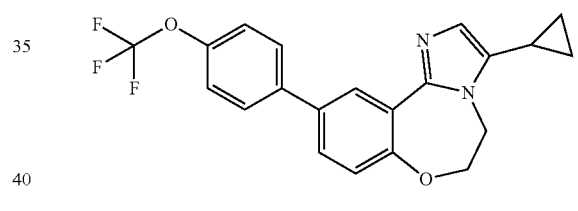

Compound II-5 was prepared according to the Examples disclosed herein using the appropriate starting materials. $C_{21}H_{17}F_3N_2O_2$. 387.1 (M+1).

Example 12

2-methyl-10-(4-(trifluoromethyl)phenyl)-5,6-dihydrobenzo[f]imidazo[1,2-d][1,4]oxazepine (Compound I-19)

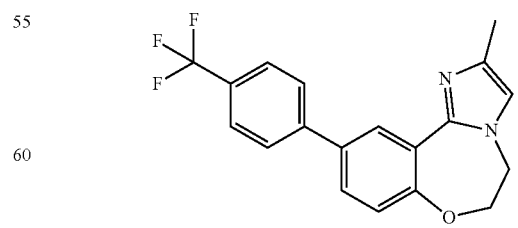

Compound I-19 was prepared according to the Examples disclosed herein using the appropriate starting materials. $C_{19}H_{15}F_3N_2O$. 345.1 (M+1).

Example 13

2-cyclopropyl-10-(4-(trifluoromethyl)phenyl)-5,6-dihydrobenzo[f]imidazo[1,2-d][1,4]oxazepine (Compound I-20)

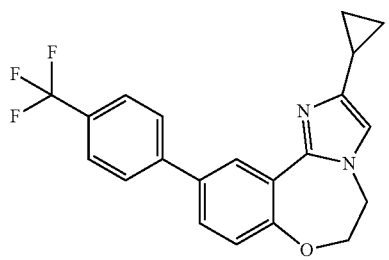 [SMILES: FC(F)(F)c1ccc(-c2ccc3c(c2)-c2nc(C4CC4)cn2CCO3)cc1]

Compound II-5 was prepared according to the Examples disclosed herein using the appropriate starting materials. $C_{21}H_{17}F_3N_2O$. 371.1 (M+1).

Example 14

5-morpholino-7-(4-(trifluoromethyl)phenyl)-2,3-dihydrobenzo[f][1,4]oxazepine (Compound II-1)

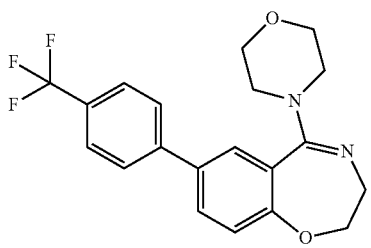 [SMILES: FC(F)(F)c1ccc(-c2ccc3c(c2)C(N2CCOCC2)=NCCO3)cc1]

Compound II-1 was prepared according to the Examples disclosed herein using the appropriate starting materials. $C_{20}H_{19}F_3N_2O_2$. 377.1 (M+1).

Example 15

N-benzyl-7-(4-(trifluoromethyl)phenyl)-2,3-dihydrobenzo[f][1,4]oxazepin-5-amine (Compound II-2)

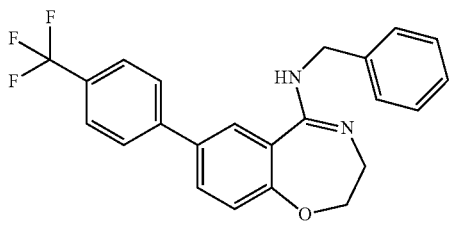 [SMILES: FC(F)(F)c1ccc(-c2ccc3c(c2)C(NCc2ccccc2)=NCCO3)cc1]

Compound II-2 was prepared according to the Examples disclosed herein using the appropriate starting materials. $C_{23}H_{19}F_3N_2O$. 397.1 (M+1).

Example 16

5-(pyrrolidin-1-yl)-7-(4-(trifluoromethyl)phenyl)-2,3-dihydrobenzo[f][1,4]oxazepine (Compound II-3)

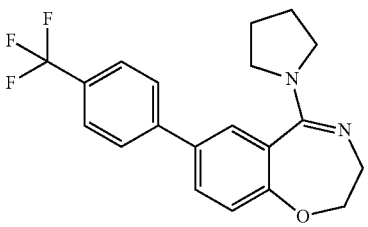 [SMILES: FC(F)(F)c1ccc(-c2ccc3c(c2)C(N2CCCC2)=NCCO3)cc1]

Compound II-3 was prepared according to the Examples disclosed herein using the appropriate starting materials. $C_{20}H_{19}F_3N_2O$. 361.1 (M+1).

Example 17

N-cyclopropyl-7-(4-(trifluoromethyl)phenyl)-2,3-dihydrobenzo[f][1,4]oxazepin-5-amine (Compound II-4)

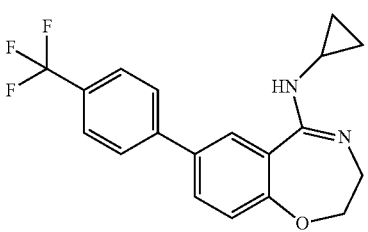 [SMILES: FC(F)(F)c1ccc(-c2ccc3c(c2)C(NC2CC2)=NCCO3)cc1]

Compound II-4 was prepared according to the Examples disclosed herein using the appropriate starting materials. $C_{19}H_{17}F_3N_2O$. 347.1 (M+1).

Example 18

N-benzyl-N-methyl-7-(4-(trifluoromethyl)phenyl)-2,3-dihydrobenzo[f][1,4]oxazepin-5-amine (Compound II-5)

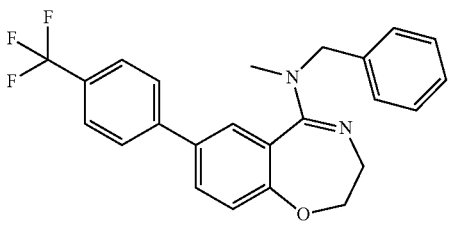 [SMILES: CN(Cc1ccccc1)C1=NCCOc2ccc(-c3ccc(C(F)(F)F)cc3)cc21]

Compound II-5 was prepared according to the Examples disclosed herein using the appropriate starting materials. $C_{24}H_{21}F_3N_2O$. 411.1 (M+1).

Example 19

(S)—N,N-dimethyl-1-(7-(4-(trifluoromethyl)phenyl)-2,3-dihydrobenzo[f][1,4]oxazepin-5-yl)pyrrolidin-3-amine (Compound II-15)

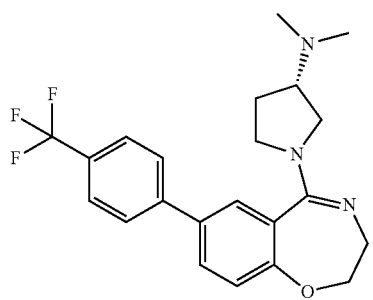

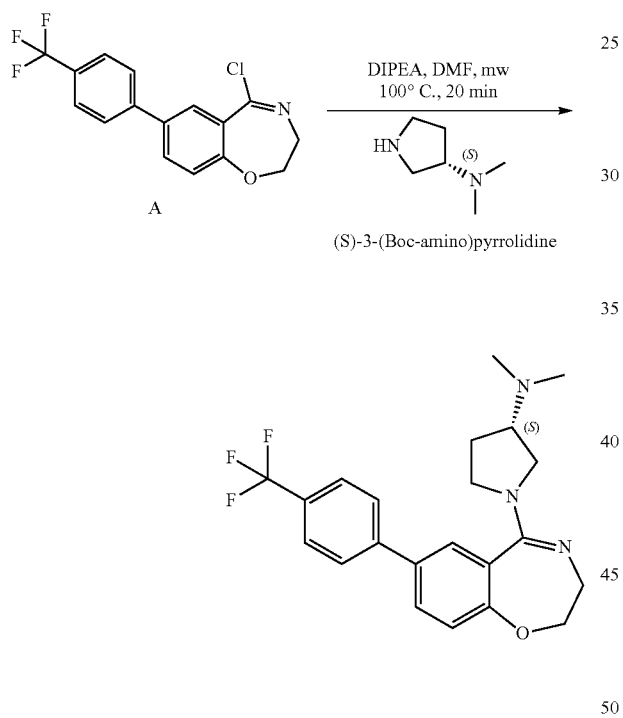

To a anhydrous DMF solution (3 mL) of the compound A (65 mg, 0.20 mmol) and (S)—N,N-dimethylpyrrolidin-3-amine (69 mg, 0.60 mmol) was added Hunig's base (0.30 mL, 1.68 mmol) with stir. The reaction mixture was subjected to Biotage microwave heating at 120° C. for 20 min. The resulting mixture was filtered, concentrated in vaccuo, and subjected to Gilson preparative HPLC, eluting with a gradient of ACN in H$_2$O (5% to 95%) to afford Compound II-15 (45 mg, 0.11 mmol, 55%). LCMS m/z 404.2 (M+H), anal HPLC 100% in purity. $^1$H NMR (400 MHz; DMSO-d6) δ 8.72 (s, 2H); 7.93 (m, 4H); 7.82 (d, J=8.1 Hz, 2H); 7.31 (d, J=8.2 Hz, 1H); 4.35 (m, 2H); 3.61-3.33 (m, 5H); 3.16 (s, 1H); 2.77 (m, 1H); 2.15 (s, 6H); 2.07 (m, 1H); 1.79 (m, 1H). $^{19}$F NMR (400 MHz; DMSO-d6) δ −61.42 (s, 3F).

Example 20

N-(pyrimidin-2-ylmethyl)-7-(4-(trifluoromethyl)phenyl)-2,3-dihydrobenzo[f][1,4]oxazepin-5-amine (Compound II-7)

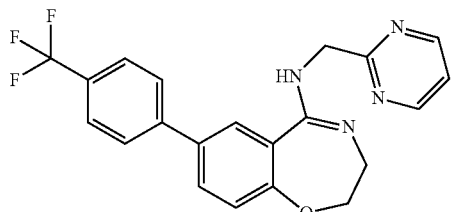

Compound II-7 was prepared according to Example 19 disclosed herein using the appropriate starting materials.

Example 21

N-cyclopropyl-N-methyl-7-(4-(trifluoromethyl)phenyl)-2,3-dihydrobenzo[f][1,4]oxazepin-5-amine (Compound II-8)

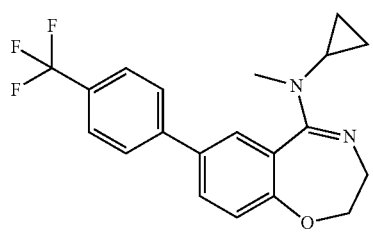 [SMILES: CN(C1=NCCOc2ccc(-c3ccc(C(F)(F)F)cc3)cc21)C1CC1]

Compound II-8 was prepared according to Example 19 disclosed herein using the appropriate starting materials.

Example 22

N-((3-fluoropyridin-2-yl)methyl)-7-(4-(trifluoromethyl)phenyl)-2,3-dihydrobenzo[f][1,4]oxazepin-5-amine (Compound II-9)

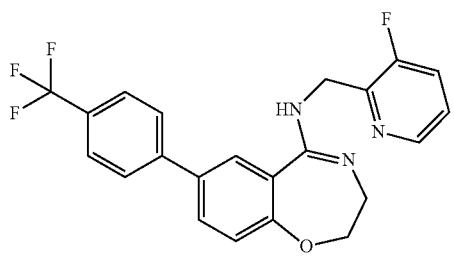 [SMILES: Fc1cccnc1CNC1=NCCOc2ccc(-c3ccc(C(F)(F)F)cc3)cc21]

Compound II-9 was prepared according to Example 19 disclosed herein using the appropriate starting materials. MS m/z 416.1, M+H.

Example 23 tert-butyl 1-(7-(4-(trifluoromethyl)phenyl)-2,3-dihydrobenzo[f][1,4]oxazepin-5-yl)azetidin-3-ylcarbamate (Compound II-12)

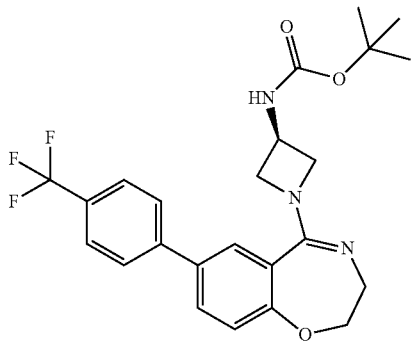

Compound II-12 was prepared according to Example 19 disclosed herein using the appropriate starting materials.

Example 24

(R)-tert-butyl 1-(7-(4-(trifluoromethyl)phenyl)-2,3-dihydrobenzo[f][1,4]oxazepin-5-yl)pyrrolidin-3-ylcarbamate (Compound II-50)

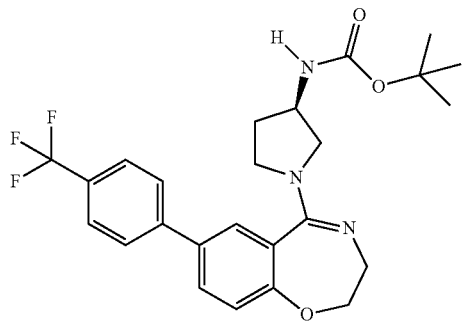

Compound II-50 was prepared according to Example 19 disclosed herein using the appropriate starting materials. MS m/z 476.1, M+H).

Example 25

(S)-tert-butyl 1-(7-(4-(trifluoromethyl)phenyl)-2,3-dihydrobenzo[f][1,4]oxazepin-5-yl)pyrrolidin-3-ylcarbamate (Compound II-13)

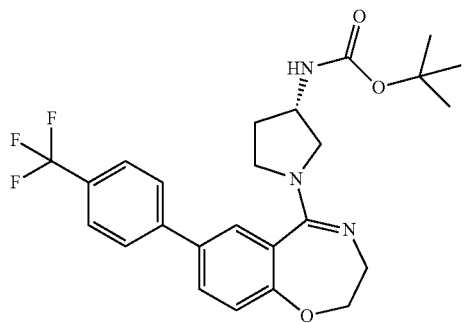 [SMILES: CC(C)(C)OC(=O)N[C@H]1CCN(C2=NCCOc3ccc(-c4ccc(C(F)(F)F)cc4)cc32)C1]

Compound II-7 was prepared according to Example 19 disclosed herein using the appropriate starting materials. MS m/z 476.1, M+H).

Example 26

N-(2-(1H-imidazol-1-yl)ethyl)-7-(4-(trifluoromethyl)phenyl)-2,3-dihydrobenzo[f][1,4]oxazepin-5-amine (Compound II-14)

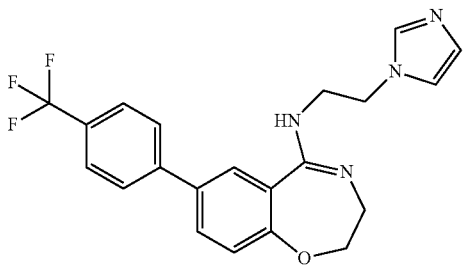 [SMILES: FC(F)(F)c1ccc(-c2ccc3c(c2)C(NCCn2ccnc2)=NCCO3)cc1]

Compound II-14 was prepared according to Example 19 disclosed herein using the appropriate starting materials. MS m/z 401.1, M+H.

Example 27

(S)-(1-(7-(4-(trifluoromethyl)phenyl)-2,3-dihydrobenzo[f][1,4]oxazepin-5-yl)pyrrolidin-3-yl)methanol (Compound II-16)

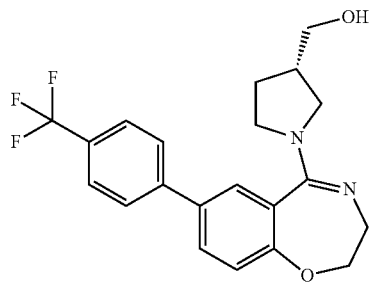 [SMILES: OC[C@H]1CCN(C2=NCCOc3ccc(-c4ccc(C(F)(F)F)cc4)cc32)C1]

Compound II-16 was prepared according to Example 19 disclosed herein using the appropriate starting materials.

Example 28

N-((1-methyl-1H-imidazol-2-yl)methyl)-7-(4-(trifluoromethyl)phenyl)-2,3-dihydrobenzo[f][1,4]oxazepin-5-amine (Compound II-17)

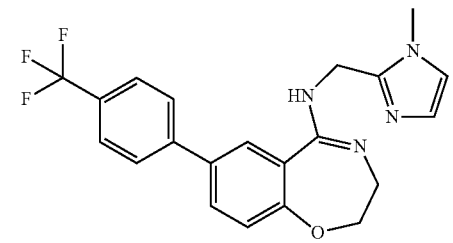 [SMILES: Cn1ccnc1CNC1=NCCOc2ccc(-c3ccc(C(F)(F)F)cc3)cc21]

Compound II-17 was prepared according to Example 19 disclosed herein using the appropriate starting materials.

Example 29

1-(7-(4-(trifluoromethyl)phenyl)-2,3-dihydrobenzo[f][1,4]oxazepin-5-yl)azetidin-3-amine (Compound II-18)

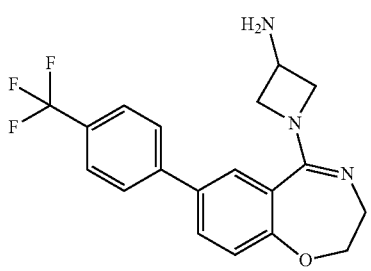 [SMILES: NC1CN(C2=NCCOc3ccc(-c4ccc(C(F)(F)F)cc4)cc32)C1]

Compound II-18 was prepared according to Example 19 disclosed herein using the appropriate starting materials.

Example 30

5-(4,4-difluoropiperidin-1-yl)-7-(4-(trifluoromethyl)phenyl)-2,3-dihydrobenzo[f][1,4]oxazepine (Compound II-21)

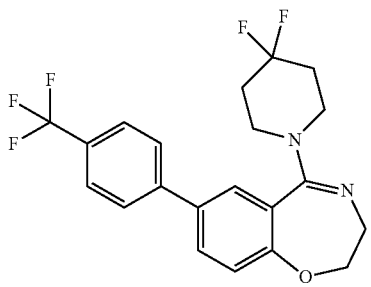 [SMILES: FC1(F)CCN(C2=NCCOc3ccc(-c4ccc(C(F)(F)F)cc4)cc32)CC1]

Compound II-21 was prepared according to Example 19 disclosed herein using the appropriate starting materials.

Example 31

1-(7-(4-(trifluoromethyl)phenyl)-2,3-dihydrobenzo[f][1,4]oxazepin-5-yl)pyrrolidin-3-ol (Compound II-23)

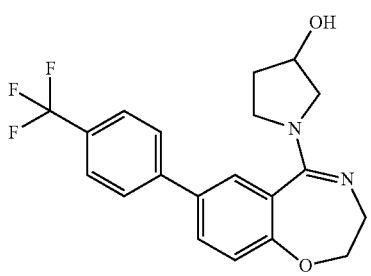 [SMILES: OC1CCN(C2=NCCOc3ccc(-c4ccc(C(F)(F)F)cc4)cc32)C1]

Compound II-23 was prepared according to Example 19 disclosed herein using the appropriate starting materials.

Example 32

N-(2-(2-chlorophenoxy)ethyl)-7-(4-(trifluoromethyl)phenyl)-2,3-dihydrobenzo[f][1,4]oxazepin-5-amine (Compound II-24)

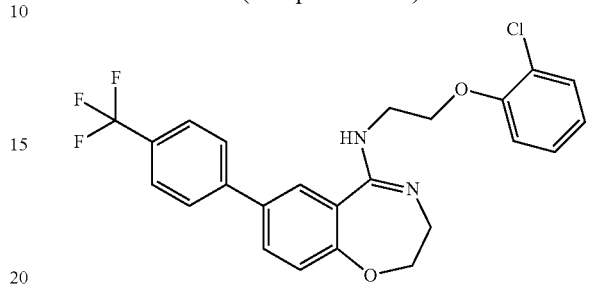

Compound II-24 was prepared according to Example 19 disclosed herein using the appropriate starting materials. MS m/z 461.1, M+H.

Example 33

7-(4-(trifluoromethyl)phenyl)-N-((6-(trifluoromethyl)pyridin-2-yl)methyl)-2,3-dihydrobenzo[f][1,4]oxazepin-5-amine (Compound II-25)

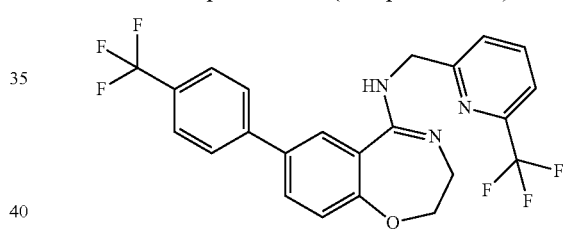

Compound II-25 was prepared according to Example 19 disclosed herein using the appropriate starting materials MS m/z 466.1, M+H.

Example 34

N-(1H-tetrazol-5-yl)-7-(4-(trifluoromethyl)phenyl)-2,3-dihydrobenzo[f][1,4]oxazepin-5-amine (Compound II-26)

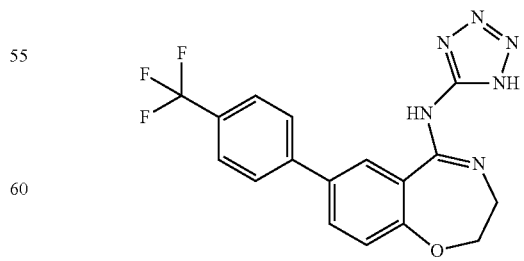

Compound II-26 was prepared according to Example 19 disclosed herein using the appropriate starting materials. MS m/z 375.1, M+H.

Example 35

7-(4-(trifluoromethyl)phenyl)-N-(6-(trifluoromethyl)pyridin-2-yl)-2,3-dihydrobenzo[f][1,4]oxazepin-5-amine (Compound II-27)

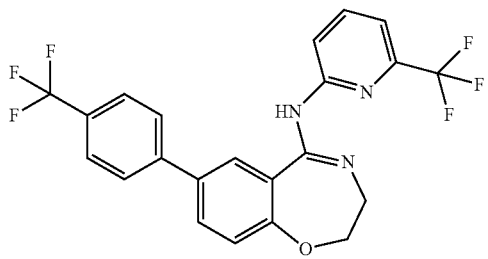 [SMILES: FC(F)(F)c1ccc(-c2ccc3c(c2)C(Nc2cccc(C(F)(F)F)n2)=NCCO3)cc1]

Compound II-27 was prepared according to Example 19 disclosed herein using the appropriate starting materials.

Example 36

5-(4-(2,2,2-trifluoroethyl)piperazin-1-yl)-7-(4-(trifluoromethyl)phenyl)-2,3-dihydrobenzo[f][1,4]oxazepine (Compound II-28)

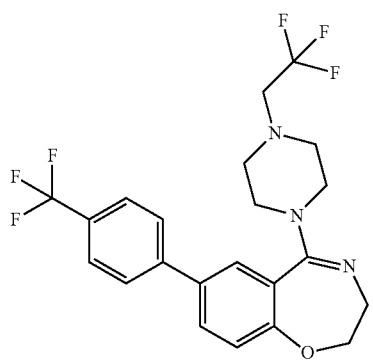 [SMILES: FC(F)(F)CN1CCN(C2=NCCOc3ccc(-c4ccc(C(F)(F)F)cc4)cc32)CC1]

Compound II-28 was prepared according to Example 19 disclosed herein using the appropriate starting materials.

Example 37

(R)—N,N-dimethyl-1-(7-(4-(trifluoromethyl)phenyl)-2,3-dihydrobenzo[f][1,4]oxazepin-5-yl)pyrrolidin-3-amine (Compound II-51)

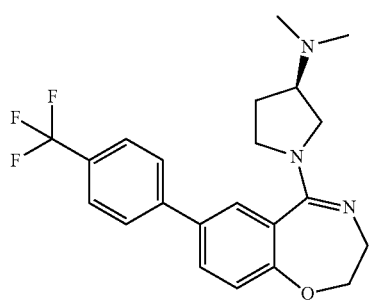 [SMILES: CN(C)[C@@H]1CCN(C2=NCCOc3ccc(-c4ccc(C(F)(F)F)cc4)cc32)C1]

Compound II-51 was prepared according to Example 19 disclosed herein using the appropriate starting materials. MS m/z 404.1, M+H.

Example 38

N-(2,2,2-trifluoroethyl)-7-(4-(trifluoromethyl)phenyl)-2,3-dihydrobenzo[f][1,4]oxazepin-5-amine (Compound II-29)

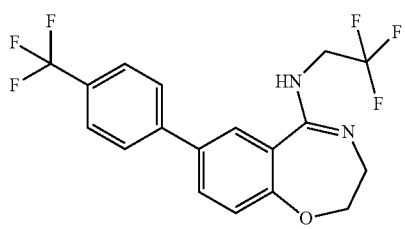 [SMILES: FC(F)(F)CNC1=NCCOc2ccc(-c3ccc(C(F)(F)F)cc3)cc21]

Compound II-29 was prepared according to Example 19 disclosed herein using the appropriate starting materials.

Example 39

1-(7-(4-(trifluoromethyl)phenyl)-2,3-dihydrobenzo[f][1,4]oxazepin-5-yl)pyrrolidin-2-one (Compound II-30)

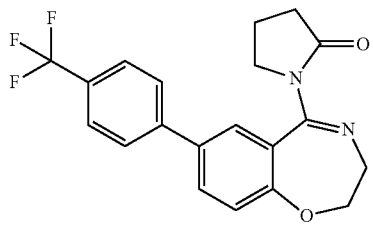 [SMILES: O=C1CCCN1C1=NCCOc2ccc(-c3ccc(C(F)(F)F)cc3)cc21]

Compound II-30 was prepared according to Example 19 disclosed herein using the appropriate starting materials.

Example 40

5-(4-methylpiperazin-1-yl)-7-(4-(trifluoromethyl)phenyl)-2,3-dihydrobenzo[f][1,4]oxazepine (Compound II-52)

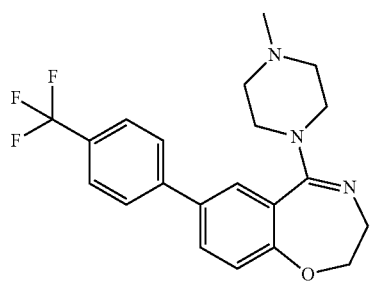 [SMILES: CN1CCN(C2=NCCOc3ccc(-c4ccc(C(F)(F)F)cc4)cc32)CC1]

Compound II-52 was prepared according to Example 19 disclosed herein using the appropriate starting materials.

Example 41

(S)-tert-butyl 3-methyl-4-(7-(4-(trifluoromethyl)phenyl)-2,3-dihydrobenzo[f][1,4]oxazepin-5-yl)piperazine-1-carboxylate (Compound II-53)

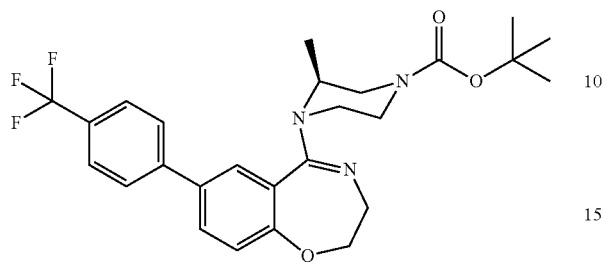

Compound II-7 was prepared according to Example 19 disclosed herein using the appropriate starting materials.

Example 42

5-(4-cyclopropylpiperazin-1-yl)-7-(4-(trifluoromethyl)phenyl)-2,3-dihydrobenzo[f][1,4]oxazepine (Compound II-31)

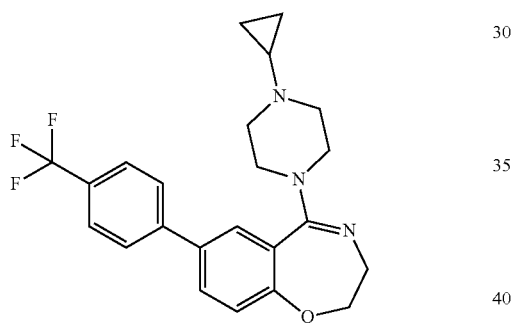

Compound II-31 was prepared according to Example 19 disclosed herein using the appropriate starting materials. MS m/z 416.1, M+H.

Example 43

N-phenyl-7-(4-(trifluoromethyl)phenyl)-2,3-dihydrobenzo[f][1,4]oxazepin-5-amine (Compound II-54)

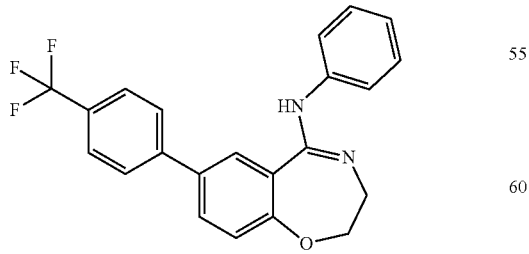

Compound II-54 was prepared according to Example 19 disclosed herein using the appropriate starting materials. MS m/z 383.1, M+H.

Example 44

5-(3-morpholinopyrrolidin-1-yl)-7-(4-(trifluoromethyl)phenyl)-2,3-dihydrobenzo[f][1,4]oxazepine (Compound II-55)

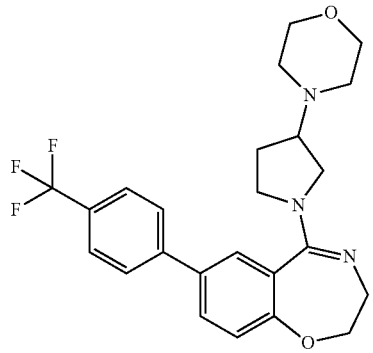 [SMILES: FC(F)(F)c1ccc(-c2ccc3c(c2)C(N2CCC(N4CCOCC4)C2)=NCCO3)cc1]

Compound II-55 was prepared according to Example 19 disclosed herein using the appropriate starting materials.

Example 45

(S)-1-(7-(4-(trifluoromethyl)phenyl)-2,3-dihydrobenzo[f][1,4]oxazepin-5-yl)pyrrolidin-3-amine (Compound II-56)

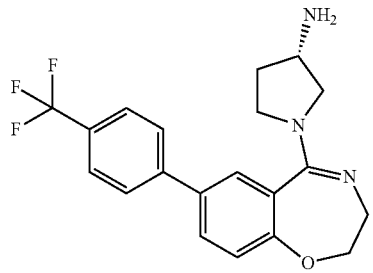 [SMILES: N[C@H]1CCN(C2=NCCOc3ccc(-c4ccc(C(F)(F)F)cc4)cc32)C1]

Compound II-56 was prepared according to Example 19 disclosed herein using the appropriate starting materials.

Example 46 tert-butyl 1-(7-(4-(trifluoromethyl)phenyl)-2,3-dihydrobenzo[f][1,4]oxazepin-5-yl)pyrrolidin-3-ylcarbamate (Compound II-57)

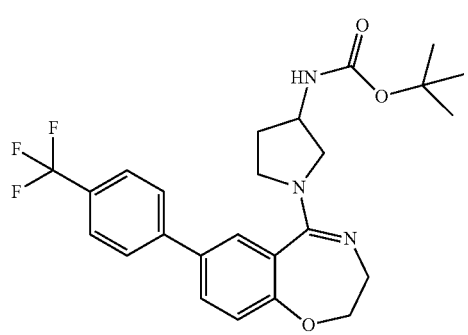 [SMILES: CC(C)(C)OC(=O)NC1CCN(C2=NCCOc3ccc(-c4ccc(C(F)(F)F)cc4)cc32)C1]

Compound II-7 was prepared according to Example 19 disclosed herein using the appropriate starting materials. MS m/z 476.1, M+H.

Example 47

5-(2-(pyridin-2-yl)pyrrolidin-1-yl)-7-(4-(trifluoromethyl)phenyl)-2,3-dihydrobenzo[f][1,4]oxazepine (Compound II-58)

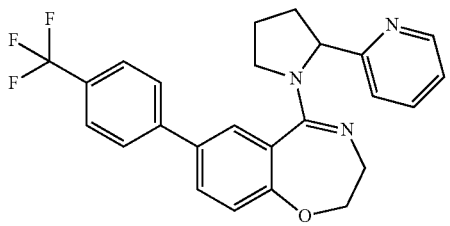 [SMILES: FC(F)(F)c1ccc(-c2ccc3c(c2)C(N2CCCC2c2ccccn2)=NCCO3)cc1]

Compound II-58 was prepared according to Example 19 disclosed herein using the appropriate starting materials.

Example 48

N-(pyrrolidin-3-yl)-7-(4-(trifluoromethyl)phenyl)-2,3-dihydrobenzo[f][1,4]oxazepin-5-amine (Compound II-59)

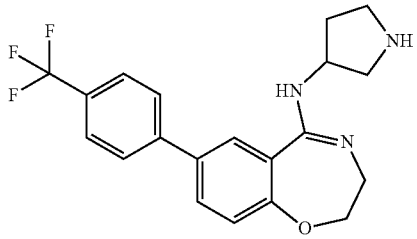 [SMILES: FC(F)(F)c1ccc(-c2ccc3c(c2)C(NC2CCNC2)=NCCO3)cc1]

Compound II-59 was prepared according to Example 19 disclosed herein using the appropriate starting materials.

Example 49

N-(1-(pyrimidin-2-ylmethyl)pyrrolidin-3-yl)-7-(4-(trifluoromethyl)phenyl)-2,3-dihydrobenzo[f][1,4]oxazepin-5-amine (Compound II-34)

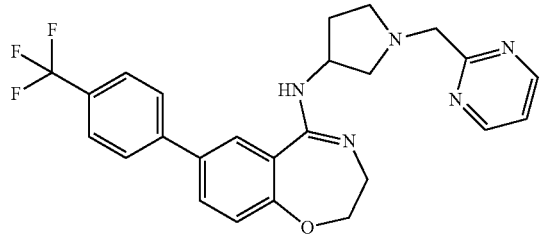 [SMILES: FC(F)(F)c1ccc(-c2ccc3c(c2)C(NC2CCN(Cc4ncccn4)C2)=NCCO3)cc1]

Compound II-34 was prepared according to Example 19 disclosed herein using the appropriate starting materials.

Example 50 pyrimidin-2-yl(3-(7-(4-(trifluoromethyl)phenyl)-2,3-dihydrobenzo[f][1,4]oxazepin-5-ylamino)pyrrolidin-1-yl)methanone (Compound II-35)

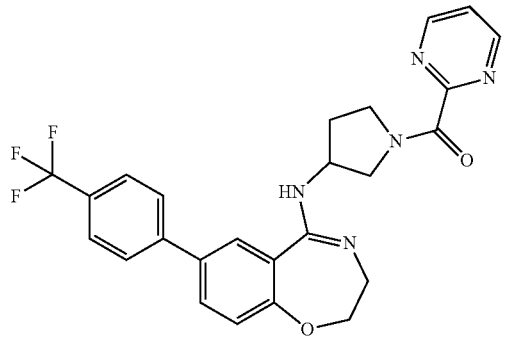 [SMILES: O=C(c1ncccn1)N1CCC(NC2=NCCOc3ccc(-c4ccc(C(F)(F)F)cc4)cc32)C1]

Compound II-35 was prepared according to Example 19 disclosed herein using the appropriate starting materials.

Example 51

5-(3-(pyridin-2-yl)pyrrolidin-1-yl)-7-(4-(trifluoromethyl)phenyl)-2,3-dihydrobenzo[f][1,4]oxazepine (Compound II-60)

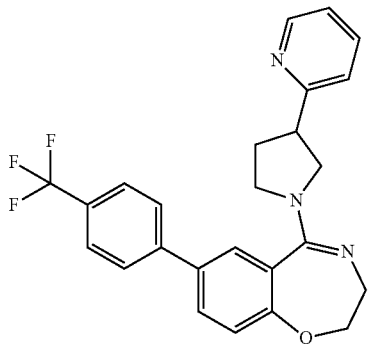 [SMILES: FC(F)(F)c1ccc(-c2ccc3c(c2)C(N2CCC(c4ccccn4)C2)=NCCO3)cc1]

Compound II-7 was prepared according to Example 19 disclosed herein using the appropriate starting materials. MS m/z 438.1, M+H.

Example 52

5-(1,3'-bipyrrolidin-1'-yl)-7-(4-(trifluoromethyl)phenyl)-2,3-dihydrobenzo[f][1,4]oxazepine (Compound II-36)

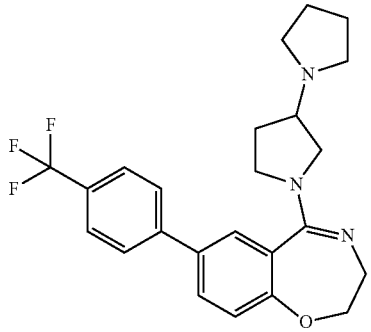 [SMILES: FC(F)(F)c1ccc(-c2ccc3c(c2)C(N2CCC(N4CCCC4)C2)=NCCO3)cc1]

Example 53

N-(pyrimidin-2-ylmethyl)-1-(7-(4-(trifluoromethyl) phenyl)-2,3-dihydrobenzo[f][1,4]oxazepin-5-yl)pyrrolidin-3-amine (Compound II-37)

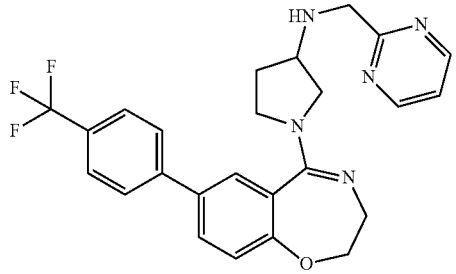 [SMILES: FC(F)(F)c1ccc(-c2ccc3c(c2)C(N2CCC(NCc4ncccn4)C2)=NCCO3)cc1]

Compound II-37 was prepared according to Example 19 disclosed herein using the appropriate starting materials. MS m/z 468.1, M+H.

Example 54

(R)-tert-butyl methyl(1-(7-(4-(trifluoromethyl)phenyl)-2,3-dihydrobenzo[f][1,4]oxazepin-5-yl)pyrrolidin-3-yl)carbamate (Compound II-38)

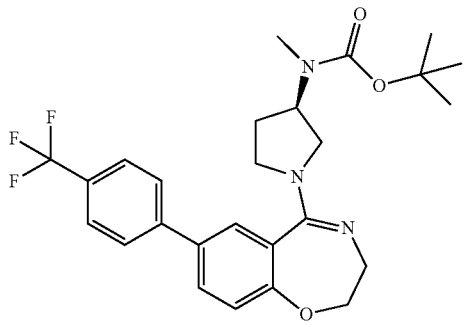 [SMILES: CN(C(=O)OC(C)(C)C)[C@@H]1CCN(C2=NCCOc3ccc(-c4ccc(C(F)(F)F)cc4)cc32)C1]

Compound II-38 was prepared according to Example 19 disclosed herein using the appropriate starting materials.

Example 55

(R)—N-methyl-1-(7-(4-(trifluoromethyl)phenyl)-2,3-dihydrobenzo[f][1,4]oxazepin-5-yl)pyrrolidin-3-amine (Compound II-39)

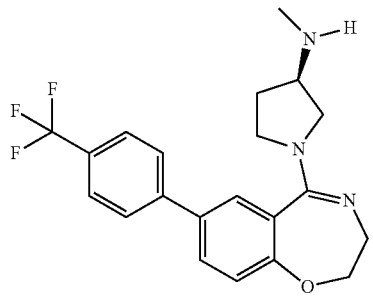 [SMILES: CN[C@@H]1CCN(C2=NCCOc3ccc(-c4ccc(C(F)(F)F)cc4)cc32)C1]

Compound II-39 was prepared according to Example 19 disclosed herein using the appropriate starting materials. MS m/z 390.1, M+H.

Example 56

(S)-tert-butyl methyl(1-(7-(4-(trifluoromethyl)phenyl)-2,3-dihydrobenzo[f][1,4]oxazepin-5-yl)pyrrolidin-3-yl)carbamate (Compound II-40)

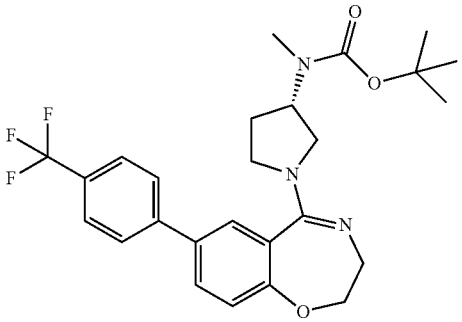 [SMILES: CN(C(=O)OC(C)(C)C)[C@H]1CCN(C2=NCCOc3ccc(-c4ccc(C(F)(F)F)cc4)cc32)C1]

Compound II-40 was prepared according to Example 19 disclosed herein using the appropriate starting materials. MS m/z 490.1, M+H.

Example 57

(R)-1-(7-(4-(trifluoromethyl)phenyl)-2,3-dihydrobenzo[f][1,4]oxazepin-5-yl)pyrrolidin-3-amine (Compound II-41)

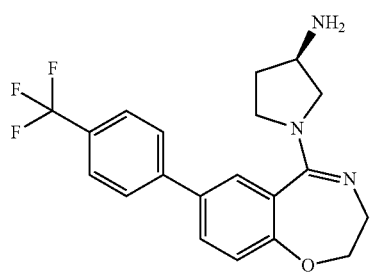 [SMILES: N[C@@H]1CCN(C2=NCCOc3ccc(-c4ccc(C(F)(F)F)cc4)cc32)C1]

Compound II-41 was prepared according to Example 19 disclosed herein using the appropriate starting materials.

Example 58

1-(1-(7-(4-(trifluoromethyl)phenyl)-2,3-dihydrobenzo[f][1,4]oxazepin-5-yl)piperidin-4-yl)pyrrolidin-2-one (Compound II-42)

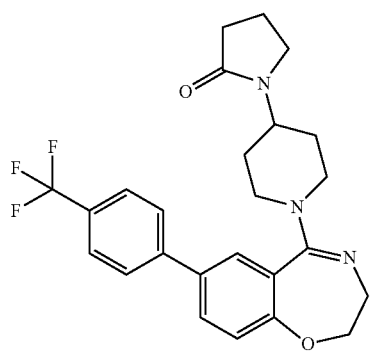 [SMILES: O=C1CCCN1C1CCN(C2=NCCOc3ccc(-c4ccc(C(F)(F)F)cc4)cc32)CC1]

Compound II-36 was prepared according to Example 19 disclosed herein using the appropriate starting materials.

Compound II-42 was prepared according to Example 19 disclosed herein using the appropriate starting materials.

Example 59

(S)—N-methyl-1-(7-(4-(trifluoromethyl)phenyl)-2,3-dihydrobenzo[f][1,4]oxazepin-5-yl)pyrrolidin-3-amine (Compound II-44)

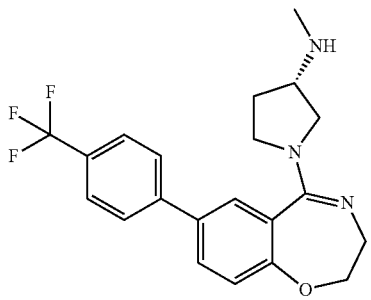 [SMILES: CN[C@H]1CCN(C2=NCCOc3ccc(-c4ccc(C(F)(F)F)cc4)cc32)C1]

Compound II-44 was prepared according to Example 19 disclosed herein using the appropriate starting materials.

Example 60

(S)—N-(1-(7-(4-(trifluoromethyl)phenyl)-2,3-dihydrobenzo[f][1,4]oxazepin-5-yl)pyrrolidin-3-yl)pyrimidine-2-carboxamide (Compound II-45)

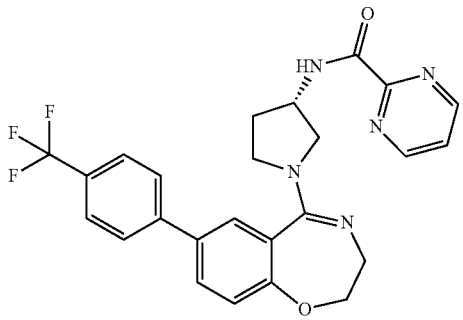 [SMILES: O=C(N[C@H]1CCN(C2=NCCOc3ccc(-c4ccc(C(F)(F)F)cc4)cc32)C1)c1ncccn1]

Compound II-45 was prepared according to Example 19 disclosed herein using the appropriate starting materials.

Example 61

(R)—N-(1-(7-(4-(trifluoromethyl)phenyl)-2,3-dihydrobenzo[f][1,4]oxazepin-5-yl)pyrrolidin-3-yl)pyrimidine-2-carboxamide (Compound II-46)

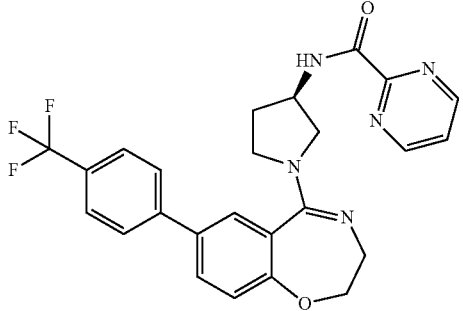 [SMILES: O=C(N[C@@H]1CCN(C2=NCCOc3ccc(-c4ccc(C(F)(F)F)cc4)cc32)C1)c1ncccn1]

Compound II-46 was prepared according to Example 19 disclosed herein using the appropriate starting materials.

Example 62

(R)—N-(1-(7-(4-(trifluoromethyl)phenyl)-2,3-dihydrobenzo[f][1,4]oxazepin-5-yl)pyrrolidin-3-yl)picolinamide (Compound II-47)

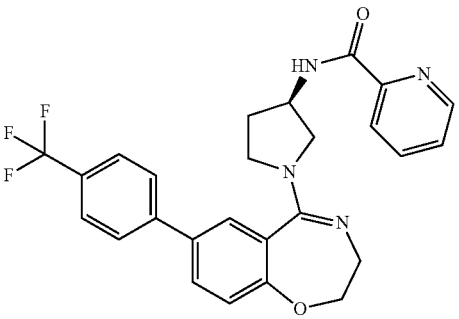 [SMILES: O=C(N[C@@H]1CCN(C2=NCCOc3ccc(-c4ccc(C(F)(F)F)cc4)cc32)C1)c1ccccn1]

Compound II-47 was prepared according to Example 19 disclosed herein using the appropriate starting materials.

Example 63

(S)—N,N-diethyl-1-(7-(4-(trifluoromethyl)phenyl)-2,3-dihydrobenzo[f][1,4]oxazepin-5-yl)pyrrolidin-3-amine (Compound II-48)

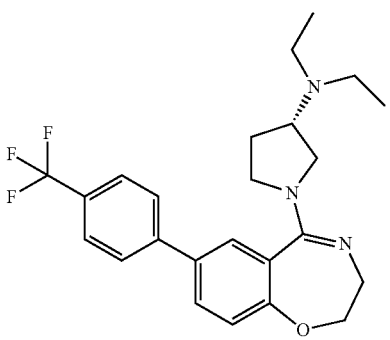 [SMILES: CCN(CC)[C@H]1CCN(C2=NCCOc3ccc(-c4ccc(C(F)(F)F)cc4)cc32)C1]

Compound II-48 was prepared according to Example 19 disclosed herein using the appropriate starting materials. MS m/z 432.1, M+H.

Example 64

1-(naphthalen-1-yloxy)-3-((R)-1-(7-(4-(trifluoromethyl)phenyl)-2,3-dihydrobenzo[f][1,4]oxazepin-5-yl)pyrrolidin-3-ylamino)propan-2-ol (Compound II-61)

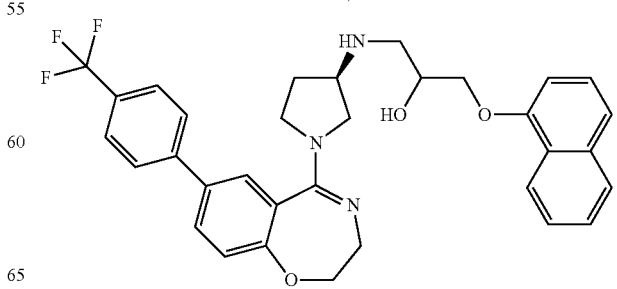

Compound II-61 was prepared according to Example 19 disclosed herein using the appropriate starting materials.

Example 65

(R)—N,N-diethyl-1-(7-(4-(trifluoromethyl)phenyl)-2,3-dihydrobenzo[f][1,4]oxazepin-5-yl)pyrrolidin-3-amine (Compound II-49)

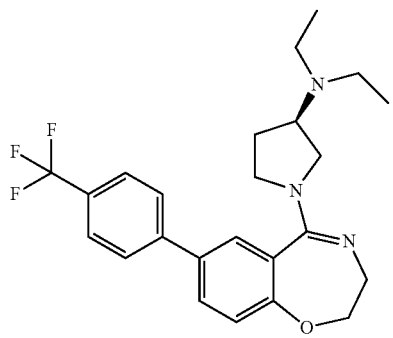 [SMILES: CCN(CC)[C@@H]1CCN(C2=NCCOc3ccc(-c4ccc(C(F)(F)F)cc4)cc32)C1]

Compound II-49 was prepared according to Example 19 disclosed herein using the appropriate starting materials.

Example 66

N-(pyridin-2-ylmethyl)-7-(4-(trifluoromethyl)phenyl)-2,3-dihydrobenzo[f][1,4]oxazepin-5-amine (Compound II-10)

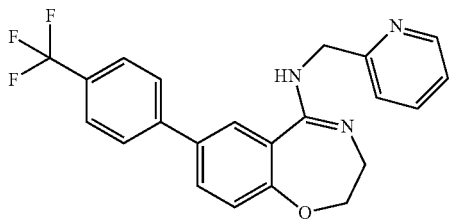

Compound II-10 was prepared according to Example 19 disclosed herein using the appropriate starting materials. MS m/z 398.1, M+H, anal HPLC>98%; $^1$H NMR (400 MHz; DMSO-d6) δ 8.51 (d, J=4.7 Hz, 1H); 8.20 (s, 1H); 7.96-7.75 (m, 7H); 7.45 (d, J=7.8 Hz, 1H); 7.26 (m, 1H); 7.20 (d, J=8.2 Hz, 1H); 4.62 (s, 2H); 4.37 (m, 2H); 3.38 (m, 2H). $^{19}$F NMR (400 MHz; DMSO-d6) δ −61.35 (s, 3F).

Example 67

N-(cyclopropylmethyl)-7-(4-(trifluoromethyl)phenyl)-2,3-dihydrobenzo[f][1,4]oxazepin-5-amine (Compound II-11)

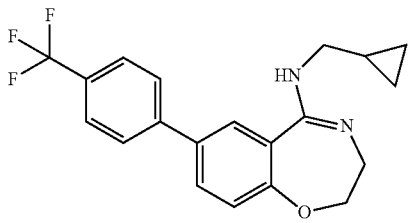 [SMILES: FC(F)(F)c1ccc(-c2ccc3c(c2)C(NCC2CC2)=NCCO3)cc1]

Compound II-11 was prepared according to Example 19 disclosed herein using the appropriate starting materials. MS m/z 361.1, M+H, anal HPLC>98%; $^1$H NMR (400 MHz; DMSO-d6) δ 8.51 (s, 1H); 8.15 (m, 3H); 8.07 (m, 3H); 7.45 (d, J=8.3 Hz, 1H); 4.61 (s, 2H); 3.43 (m, 2H); 1.36 (m, 1H); 0.71 (m, 2H); 0.49 (m, 2H). $^{19}$F NMR (400 MHz; DMSO-d6) δ −60.96 (s, 3F).

Example 68

N-(pyridin-2-yl)-7-(4-(trifluoromethyl)phenyl)-2,3-dihydrobenzo[f][1,4]oxazepin-5-amine (Compound II-19)

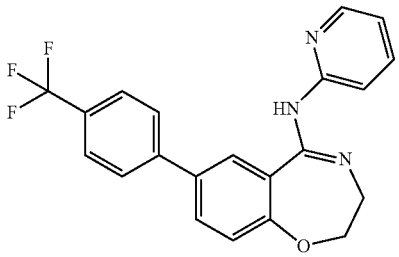 [SMILES: FC(F)(F)c1ccc(-c2ccc3c(c2)C(Nc2ccccn2)=NCCO3)cc1]

Compound II-19 was prepared according to Example 19 disclosed herein using the appropriate starting materials. MS m/z 384.1, M+H, anal HPLC>95%; $^1$H NMR (400 MHz; DMSO-d6) δ 8.33 (d, J=4.7 Hz, 1H); 8.26 (s, 1H); 8.12 (s, 1H); 7.92-7.80 (m, 6H); 7.70 (m, 1H); 7.20 (d, J=8.2 Hz, 1H); 6.99 (m, 1H); 4.38 (m, 2H); 3.56 (m, 2H). $^{19}$F NMR (400 MHz; DMSO-d6) δ −61.37 (s, 3F).

Example 69

N-(2-(pyridin-2-yloxy)ethyl)-7-(4-(trifluoromethyl)phenyl)-2,3-dihydrobenzo[f][1,4]oxazepin-5-amine (Compound II-20)

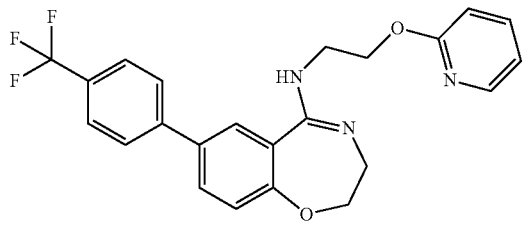 [SMILES: FC(F)(F)c1ccc(-c2ccc3c(c2)C(NCCOc2ccccn2)=NCCO3)cc1]

Compound II-20 was prepared according to Example 19 disclosed herein using the appropriate starting materials. MS m/z 428.1, M+H, anal HPLC>95%; $^1$H NMR (400 MHz; DMSO-d6) δ 8.26 (s, 1H); 8.13 (m, 1H); 7.92-7.67 (m, 7H); 7.20 (d, J=8.6 Hz, 1H); 6.96 (m, 1H); 6.82 (d, J=8.6 Hz, 1H); 4.48 (m, 2H); 4.40 (m, 2H); 3.69 (m, 2H); 3.43 (m, 2H). $^{19}$F NMR (400 MHz; DMSO-d6) δ −61.36 (s, 3F).

Example 70

N-(2-phenoxyethyl)-7-(4-(trifluoromethyl)phenyl)-2,3-dihydrobenzo[f][1,4]oxazepin-5-amine (Compound II-22)

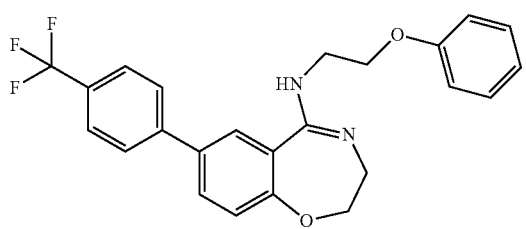 [SMILES: FC(F)(F)c1ccc(-c2ccc3c(c2)C(NCCOc2ccccc2)=NCCO3)cc1]

Compound II-22 was prepared according to Example 19 disclosed herein using the appropriate starting materials. MS m/z 427.1, M+H, anal HPLC>95%; $^1$H NMR (400 MHz; DMSO-d6) δ 8.16 (s, 1H); 7.93-7.79 (m, 6H); 7.31-7.21 (m, 3H); 6.99-6.90 (m, 3H); 4.42 (m, 2H); 4.21 (m, 2H); 3.70 (m, 2H); 3.50 (m, 2H). $^{19}$F NMR (400 MHz; DMSO-d6) δ −61.36 (s, 3F).

Example 71

N-((1-methyl-1H-benzo[d]imidazol-2-yl)methyl)-7-(4-(trifluoromethyl)phenyl)-2,3-dihydrobenzo[f][1,4]oxazepin-5-amine (Compound II-33)

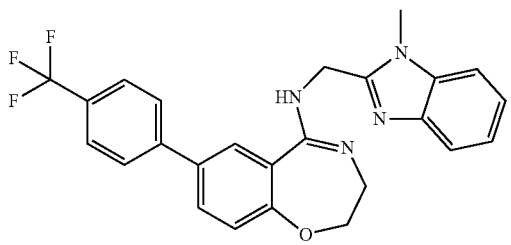 [SMILES: Cn1c(CNC2=NCCOc3ccc(-c4ccc(C(F)(F)F)cc4)cc32)nc2ccccc21]

Compound II-33 was prepared according to Example 19 disclosed herein using the appropriate starting materials. MS m/z 451.1, M+H, anal HPLC>98%; $^1$H NMR (400 MHz; DMSO-d6) δ 10.53 (s, 1H); 8.11 (d, J=7.6 Hz, 1H); 8.06 (s, 1H); 7.97 (m, 2H); 7.88 (m, 2H); 7.63 (m, 2H); 7.40 (m, 1H); 7.31 (m, 1H); 7.24 (m, 2H); 5.06 (m, 2H); 4.51 (m, 2H); 3.86 (s, 3H); 3.63 (m, 2H). $^{19}$F NMR (400 MHz; DMSO-d6) δ −61.43 (s, 3F).

Example 72 tert-butyl 3-(7-(4-(trifluoromethyl)phenyl)-2,3-dihydrobenzo[f][1,4]oxazepin-5-ylamino)pyrrolidine-1-carboxylate (Compound II-62)

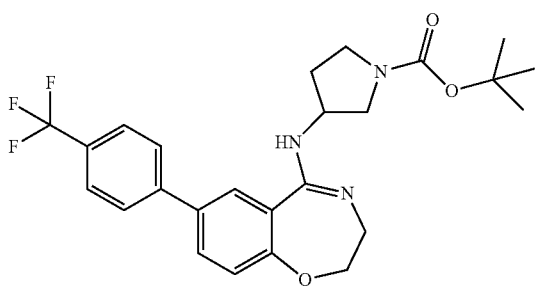 [SMILES: CC(C)(C)OC(=O)N1CCC(NC2=NCCOc3ccc(-c4ccc(C(F)(F)F)cc4)cc32)C1]

Compound II-62 was prepared according to Example 19 disclosed herein using the appropriate starting materials. MS m/z 476.2, M+H, anal HPLC>95%; $^1$H NMR (400 MHz; DMSO-d6) δ 10.18 (m, 1H); 9.97 (m, 1H); 8.10 (d, J=8.2 Hz, 1H); 7.97-7.95 (m, 5H); 7.36 (m, 1H); 4.48 (m, 2H); 4.34 (m, 1H); 3.70 (m, 1H); 3.57 (m, 2H); 2.24 (m, 1H); 2.05 (m, 2H); 1.39 (m, 9H). $^{19}$F NMR (400 MHz; DMSO-d6) δ −61.43 (s, 3F).

Example 73

(S)-tert-butyl 3-(7-(4-(trifluoromethyl)phenyl)-2,3-dihydrobenzo[f][1,4]oxazepin-5-ylamino)pyrrolidine-1-carboxylate (Compound II-43)

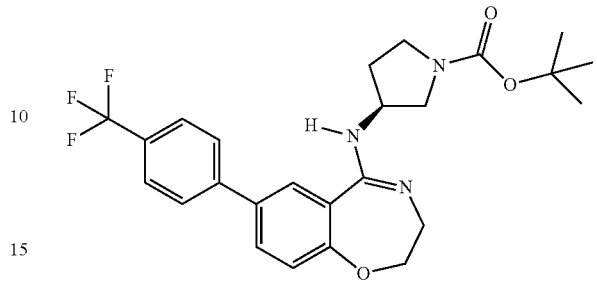

Compound II-43 was prepared according to Example 19 disclosed herein using the appropriate starting materials. MS m/z 476.2, M+H, anal HPLC>93%; $^1$H NMR (400 MHz; DMSO-d6) δ 8.22 (s, 1H); 7.91 (m, 2H); 7.81 (m, 3H); 7.73 (s, 1H); 7.16 (m, 1H); 4.36 (m, 3H); 3.58-3.20 (m, 7H); 2.12 (m, 1H); 1.88 (m, 1H); 1.38 (m, 9H). $^{19}$F NMR (400 MHz; DMSO-d6) δ −61.36 (s, 3F).

Example 74

(R)-tert-butyl 3-(7-(4-(trifluoromethyl)phenyl)-2,3-dihydrobenzo[f][1,4]oxazepin-5-ylamino)pyrrolidine-1-carboxylate (Compound II-63)

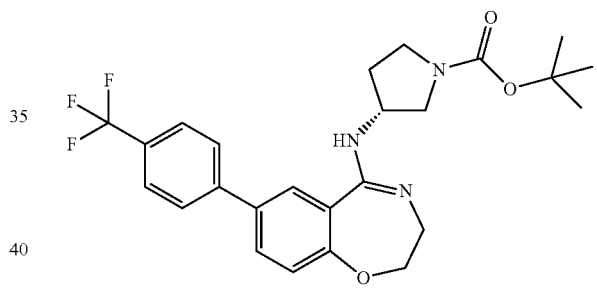

Compound II-63 was prepared according to Example 19 disclosed herein using the appropriate starting materials. MS m/z 476.2, M+H, anal HPLC>95%; $^1$H NMR (400 MHz; DMSO-d6) δ 8.23 (s, 1H); 7.91 (m, 2H); 7.81 (m, 3H); 7.73 (s, 1H); 7.14 (m, 1H); 4.36 (m, 3H); 3.58-3.20 (m, 7H); 2.12 (m, 1H); 1.88 (m, 1H); 1.38 (m, 9H). $^{19}$F NMR (400 MHz; DMSO-d6) δ −61.36 (s, 3F).

The following compounds were prepared according to the Examples disclosed herein using the appropriate starting materials:

3-methyl-10-(4-(trifluoromethyl)phenyl)-5,6-dihydrobenzo[f][1,2,4]triazolo[4,3-d][1,4]oxazepine (Compound I-4)

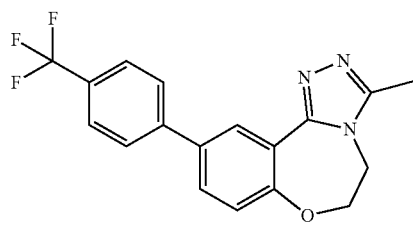 [SMILES: Cc1nnc2n1CCOc1ccc(-c3ccc(C(F)(F)F)cc3)cc1-2]

11-(4-(trifluoromethyl)phenyl)-3,4,6,7-tetrahydro-
2H-benzo[f]pyrimido[1,2-d][1,4]oxazepine (Compound I-8)

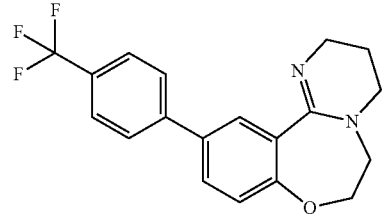 [SMILES: FC(F)(F)c1ccc(-c2ccc3c(c2)C2=NCCCN2CCO3)cc1]

3-cyclopropyl-10-(4-(trifluoromethyl)phenyl)-5,6-
dihydrobenzo[f]imidazo[1,2-d][1,4]oxazepine
(Compound I-9)

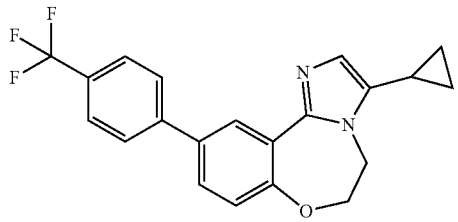 [SMILES: FC(F)(F)c1ccc(-c2ccc3c(c2)-c2ncc(C4CC4)n2CCO3)cc1]

2-(10-(4-(trifluoromethyl)phenyl)-5,6-dihydrobenzo
[f]imidazo[1,2-d][1,4]oxazepin-3-yl)propan-2-ol
(Compound I-10)

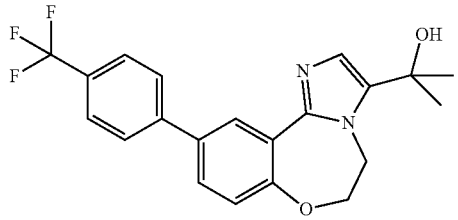 [SMILES: CC(C)(O)c1cnc2n1CCOc1ccc(-c3ccc(C(F)(F)F)cc3)cc1-2]

3-bromo-10-(4-(trifluoromethyl)phenyl)-5,6-dihydrobenzo[f]imidazo[1,2-d][1,4]oxazepine (Compound I-12)

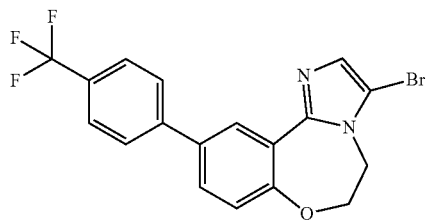 [SMILES: FC(F)(F)c1ccc(-c2ccc3c(c2)-c2ncc(Br)n2CCO3)cc1]

3-chloro-10-(4-(trifluoromethyl)phenyl)-5,6-dihydrobenzo[f]imidazo[1,2-d][1,4]oxazepine (Compound I-13)

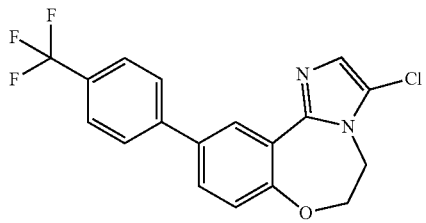 [SMILES: FC(F)(F)c1ccc(-c2ccc3c(c2)-c2ncc(Cl)n2CCO3)cc1]

10-(4-(trifluoromethyl)phenyl)-5,6-dihydrobenzo[f]
imidazo[1,2-d][1,4]oxazepine-3-carbonitrile (Compound I-16)

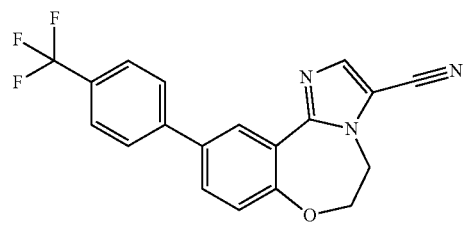 [SMILES: N#Cc1cnc2n1CCOc1ccc(-c3ccc(C(F)(F)F)cc3)cc1-2]

ethyl 10-(4-(trifluoromethyl)phenyl)-5,6-dihydrobenzo[f]imidazo[1,2-d][1,4]oxazepine-2-carboxylate (Compound I-21)

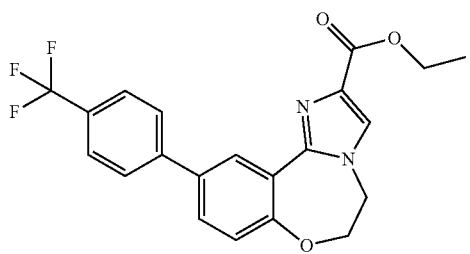 [SMILES: CCOC(=O)c1cn2c(n1)-c1cc(-c3ccc(C(F)(F)F)cc3)ccc1OCC2]

10-(4-(trifluoromethyl)phenyl)-5,6-dihydrobenzo[f]
imidazo[1,2-d][1,4]oxazepine-2-carboxylic acid
(Compound I-22)

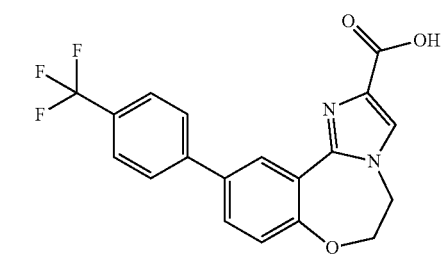 [SMILES: O=C(O)c1cn2c(n1)-c1cc(-c3ccc(C(F)(F)F)cc3)ccc1OCC2]

5-(3,3-difluoropyrrolidin-1-yl)-7-(4-(trifluoromethyl)phenyl)-2,3-dihydrobenzo[f][1,4]oxazepine (Compound II-6)

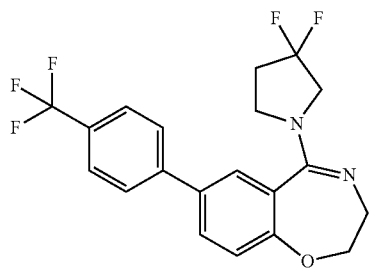 [SMILES: FC1(F)CCN(C2=NCCOc3ccc(-c4ccc(C(F)(F)F)cc4)cc32)C1]

N-phenyl-7-(4-(trifluoromethyl)phenyl)-2,3-dihydrobenzo[f][1,4]oxazepin-5-amine (Compound II-32)

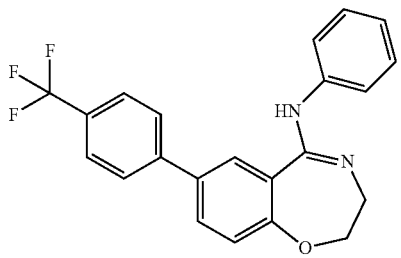 [SMILES: FC(F)(F)c1ccc(-c2ccc3c(c2)C(Nc2ccccc2)=NCCO3)cc1]

Example 75

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 76

A tablet Formula Is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 77

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 78

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Example 79

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 80

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |

-continued

| Ingredient | Amount |
| --- | --- |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Example 81

A subcutaneous formulation may be prepared as follows:

| Ingredient | Quantity |
| --- | --- |
| Active Ingredient | 5.0 mg |
| Corn Oil | 1.0 mL |

Example 82

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 83

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Example 84

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 85

Activity testing is conducted in the Examples below using methods described herein and those well known in the art. Sodium Current Screening Assays:

The late sodium current (Late INa) and peak sodium current (Peak INa) assays are performed on an automated electrophysiology platform, QPatch 16X (Sophion Bioscience, Copenhagen, Denmark), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 µg/mL Geneticin in the culture medium. Cells isolated for use on QPatch are incubated for 5 minutes in Detachin 1X (Genlantis, San Diego, USA) at 37° C. to ensure that 80-90% of the cells are single and not part of a cell cluster. Experiments are carried out at 23-25° C.

For both the Late INa and Peak INa assays, series resistance compensation is set to 100% and series resistance and whole-cell compensation are performed automatically. Currents are digitized at 25 kHz and low-pass filtered at 12 kHz and 10 kHz for the late and peak INa assays, respectively. Currents through open sodium channels are automatically recorded and stored in the Sophion Bioscience Oracle database (Sophion Bioscience, Copenhagen, Denmark). Analysis is performed using QPatch Assay and database software and data are compiled in Excel.

Compound stocks are routinely made by the Gilead Sample Bank in plastic vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM $CaCl_2$, 0.75 mM $MgCl_2$ and 5 mM HEPES with pH adjusted to 7.4 using NaOH. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 1 µM in glass vials and then transferred to glass well plates before robotic addition to the cells. A 0 mM Na extracellular solution (0 Na-ECF) is used at the end of each experiment for the Late INa and Peak INa assays to measure baseline current contains: 140 mM N-methyl-D-glucamine; 4 mM KCl; 1.8 mM $CaCl_2$; 0.75 mM $MgCl_2$; 5 mM HEPES and pH was adjusted to 7.4 with HCl.

Late INa Screening Assay:

For the $hNa_v1.5$ Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical $hNa_v1.5$ sodium currents activate rapidly to a peak negative current and then inactivate nearly completely within 3-4 ms.

Compounds were tested to determine their activity in blocking the late sodium current. Late INa was generated by adding 10 µM Tefluthrin (pyrethroid) to the extracellular solution while recording Na currents. To confirm the block of late $I_{Na}$ observed using the automated screening method, a second late $I_{Na}$ enhancer (ATX-II) and the manual patch clamp method were used. ATX-II and tefluthrin occupy distinct, non-overlapping binding sites and modify $Na^+$ channel function differently to increase late $I_{Na}$. Compounds tested have been found generally to inhibit the enhanced late $I_{Na}$ caused by either late $I_{Na}$ enhancer. For the purposes of the screening, late INa is defined as the mean current between 225 ms and 250 ms after stepping to −20 mV to activate Na channels. After establishing the whole cell recording configuration, late INa activator is added to each well 4 times over a 16-17 minute period so that the late component of the Na current reaches a stable value. Compounds were then added (typically at 1 µM), in the presence of the late INa activator, with 3 additions over the course of 7 or 8 minutes. Measurements were made at the end of exposure to the third compound addition and values were normalized to the current level when all $Na^+$ was removed from the extracellular solution after two additions of 0 Na-ECF.

Results are reported as percent block of late INa. For example, when tested in the assay disclosed above with 10 µM Tefluthrin activating late INa, Compound II-105 inhibited (or reduced) the late sodium current by 45% (see Table 1 for additional compound data). The inhibition of Late INa of the cardiac isoform $hNa_v$ 1.5 support the use of the compounds of this disclosure to treat atrial arrhythmias, ventricular arrhythmias, heart failure (including congestive heart failure, diastolic heart failure, systolic heart failure, acute heart failure), Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication.

Peak INa Screening Assay:

Compounds were also evaluated for their effect in several other assays, including their effect on $hNa_v1.5$ Peak INa. Good separation between the concentrations of test compound to reduce late and peak $I_{Na}$ is beneficial to enable separation of the desired effect to reduce late $I_{Na}$-induced electrical and mechanical dysfunction from the undesired effect to reduce peak $I_{Na}$, which can lead to slowing or block of conduction of electrical excitation in the heart. It is contemplated that the compounds of Formula I avoid significant block of peak INa. Since the peak INa in the cells used herein can be very large, introducing artifacts in the recording, the concentration of $Na^+$ in the bath can be reduced to 20 mM and a nonpermeant cation added to compensate for the $Na^+$ that was removed to maintain the osmolarity and ionic strength of the solution (see solution details below). Analysis of peak INa generally requires correction for rundown before determining the % block of peak current by the tested compound.

A separate Peak INa screening assay was developed to allow assessment of the effect of compounds on peak INa at both low and high stimulation frequencies in order to identify compounds that are highly selective for block of late INa but do not block peak INa. A low stimulation frequency of 0.1 Hz was used to determine the effect of the test compound when the channel spent most of the time in the resting (closed) state and provides information about Tonic Block (TB). A higher stimulation frequency (3 Hz) was used to measure block of the channel when it spent more time in the activated and inactivated states and provided a measure of Use-Dependent Block (UDB). Use-dependent block refers to the accumulation of block with increased frequency of channel activation. Block of cardiac peak $I_{Na}$ by compounds of this disclosure is increased with an increase in the frequency of stimulation from 0.1 to 1-5 Hz (frequencies encountered either in the normal heart or during tachycardia). It is therefore expected that reduction of peak $I_{Na}$ by compounds of this disclosure will be greater at high heart rates, such as those during tachyarrhythmias, than at normal heart rates. As a consequence, compounds of this disclosure may reduce $Na^+$ and $Ca^{2+}$ overload due to late INa and abnormal electrical activity and electrical conduction in myocardium that is arrhythmic, especially during ischemia.

The −100 mV holding potential and the 3 Hz stimulation frequency were chosen so that the benchmark compound would have a small but detectable effect under experimental conditions, allowing for direct comparison of new compounds with the benchmark. The extracellular solution for screening Peak INa is composed of: 20 mM NaCl, 120 mM N-methyl-D glucamine, 4 mM KCl, 1.8 mM CaCl$_2$, 0.75 mM MgCl$_2$ and 5 mM HEPES with pH adjusted to 7.4 using HCl. The intracellular solution used for the Peak INa assay is the same as outlined for the Late INa assay (see above).

For the peak INa assay, Na$^+$ channels were activated by depolarizing the cell membrane to 0 mV for 20 ms from a holding potential of −100 mV. After establishing the whole cell recording configuration, channels were stimulated to open with low frequency stimulation (0.1 Hz) for 7 minutes so that the recording can be monitored and the extent to which the recording has stabilized can be assessed. After this stabilization period the stimulation frequency was increased to 3 Hz for 2 minutes and then returned to 0.1 Hz. Since 3 Hz stimulation causes a small decrease in the peak current even in the absence of compound, this internal control was used for each cell, when no compound is present, to correct the results from 3 Hz stimulation when compound is present. Following 3 Hz stimulation under control conditions, the cell is allowed to recover for 200 seconds before compound is added. The test compound tested at 1 or 3 µM (depending on the % block of late INa at 1 µM) was added 3 times at 60 second intervals, while stimulating the channels to open at 0.1 Hz to monitor the progression of TB. After the third compound addition, a 320 second wait period was imposed to allow for equilibration before the second period of 3 Hz stimulation begins. TB was measured before the second period of 3 Hz stimulation. Both TB and UDB were analyzed by incorporating rundown correction for the peak INa and UDB as calculated by compensating for the small use-dependent effect of the stimulation protocol on peak INa in the absence of compound. Compound II-11 exhibited peak INa TB of 11% and peak INa UDB of 31%, both measured at 1 µM.

The above data demonstrates the selectivity of Compound II-11 to block late INa compared to peak INa (41% versus 11% for peak INa TB) which suggests compound II-11 should have minimal to no effect on electrical conduction through the heart (which is driven by peak INa) at concentrations that effectively block late INa.

Compound II-11 inhibits peak INa UDB at 31% @ 1 µM. This suggests that Compound II-11 may be useful at high heart rates, such as those during tachyarrhythmias, than at normal heart rates. As a consequence, compounds of this disclosure may reduce Na$^+$ and Ca$^{2+}$ overload due to late INa and abnormal electrical activity and electrical conduction in myocardium that is arrhythmic, especially during ischemia.

TABLE 1

| No. | Name | Late $I_{Na}$* | Peak TB* | Peak UDB* | NAV1.1 UDB-10 HZ* | NAV1.2 UDB-10 HZ* |
|---|---|---|---|---|---|---|
| I-1 | 10-(4-(trifluoromethyl)phenyl)-5,6-dihydrobenzo[f]imidazo[1,2-d][1,4]oxazepine | 32 | | | −12 | 2 |
| I-2 | 10-(4-(trifluoromethoxy)phenyl)-5,6-dihydrobenzo[f]imidazo[1,2-d][1,4]oxazepine | 31 | | | 1 | 18 |
| I-3 | 10-(4-(trifluoromethyl)phenyl)-5,6-dihydrobenzo[f][1,2,4]triazolo[4,3-d][1,4]oxazepine | 13 | | | | |
| I-4 | 3-methyl-10-(4-(trifluoromethyl)phenyl)-5,6-dihydrobenzo[f][1,2,4]triazolo[4,3-d][1,4]oxazepine | 10 | | | | |
| I-5 | 3-cyclopropyl-10-(4-(trifluoromethyl)phenyl)-5,6-dihydrobenzo[f][1,2,4]triazolo[4,3-d][1,4]oxazepine | 18 | | | | |
| I-6 | 3-methyl-10-(4-(trifluoromethyl)phenyl)-5,6-dihydrobenzo[f]imidazo[1,2-d][1,4]oxazepine | 28 | | | −10 | −3 |
| I-7 | 3-(pyrimidin-2-yl)-10-(4-(trifluoromethyl)phenyl)-5,6-dihydrobenzo[f]imidazo[1,2-d][1,4]oxazepine | 17 | | | | |
| I-8 | 11-(4-(trifluoromethyl)phenyl)-3,4,6,7-tetrahydro-2H-benzo[f]pyrimido[1,2-d][1,4]oxazepine | 9 | | | | |
| I-9 | 3-cyclopropyl-10-(4-(trifluoromethyl)phenyl)-5,6-dihydrobenzo[f]imidazo[1,2-d][1,4]oxazepine | 4 | | | 4 | 0 |
| I-10 | 2-(10-(4-(trifluoromethyl)phenyl)-5,6-dihydrobenzo[f]imidazo[1,2-d][1,4]oxazepin-3-yl)propan-2-ol | 10 | | | −5 | 0 |
| I-11 | 3-benzyl-10-(4-(trifluoromethyl)phenyl)-5,6-dihydrobenzo[f]imidazo[1,2-d][1,4]oxazepine | 13 | | | −5 | −5 |
| I-12 | 3-bromo-10-(4-(trifluoromethyl)phenyl)-5,6-dihydrobenzo[f]imidazo[1,2-d][1,4]oxazepine | 4 | | | −7 | 6 |

TABLE 1-continued

| No. | Name | Late I$_{Na}$* | Peak TB* | Peak UDB* | NAV1.1 UDB-10 HZ* | NAV1.2 UDB-10 HZ* |
|---|---|---|---|---|---|---|
| I-13 | 3-chloro-10-(4-(trifluoromethyl)phenyl)-5,6-dihydrobenzo[f]imidazo[1,2-d][1,4]oxazepine | 6 | | | −3 | 8 |
| I-14 | 2-chloro-3-methyl-10-(4-(trifluoromethyl)phenyl)-5,6-dihydrobenzo[f]imidazo[1,2-d][1,4]oxazepine | 11 | | | 0 | 4 |
| I-15 | 1-(10-(4-(trifluoromethyl)phenyl)-5,6-dihydrobenzo[f]imidazo[1,2-d][1,4]oxazepin-3-yl)ethanone | 12 | | | | |
| I-16 | 10-(4-(trifluoromethyl)phenyl)-5,6-dihydrobenzo[f]imidazo[1,2-d][1,4]oxazepine-3-carbonitrile | 1 | | | | |
| I-17 | 3-methyl-10-(4-(trifluoromethoxy)phenyl)-5,6-dihydrobenzo[f]imidazo[1,2-d][1,4]oxazepine | 14 | | | | |
| I-18 | 3-cyclopropyl-10-(4-(trifluoromethoxy)phenyl)-5,6-dihydrobenzo[f]imidazo[1,2-d][1,4]oxazepine | 20 | | | | |
| I-19 | 2-methyl-10-(4-(trifluoromethyl)phenyl)-5,6-dihydrobenzo[f]imidazo[1,2-d][1,4]oxazepine | 13 | | | | |
| I-20 | 2-cyclopropyl-10-(4-(trifluoromethyl)phenyl)-5,6-dihydrobenzo[f]imidazo[1,2-d][1,4]oxazepine | 12 | | | | |
| I-22 | 10-(4-(trifluoromethyl)phenyl)-5,6-dihydrobenzo[f]imidazo[1,2-d][1,4]oxazepine-2-carboxylic acid | 5 | | | | |
| I-23 | 2-(1-methyl-1H-imidazol-5-yl)-10-(4-(trifluoromethyl)phenyl)-5,6-dihydrobenzo[f]imidazo[1,2-d][1,4]oxazepine | 3 | | | | |
| II-1 | 5-morpholino-7-(4-(trifluoromethyl)phenyl)-2,3-dihydrobenzo[f][1,4]oxazepine | 21 | | | | |
| II-2 | N-benzyl-7-(4-(trifluoromethyl)phenyl)-2,3-dihydrobenzo[f][1,4]oxazepin-5-amine | 41 | 27 | 57 | 9 | 24 |
| II-3 | 5-(pyrrolidin-1-yl)-7-(4-(trifluoromethyl)phenyl)-2,3-dihydrobenzo[f][1,4]oxazepine | 25 | | | | |
| II-4 | N-cyclopropyl-7-(4-(trifluoromethyl)phenyl)-2,3-dihydrobenzo[f][1,4]oxazepin-5-amine | 25 | | | | |
| II-5 | N-benzyl-N-methyl-7-(4-(trifluoromethyl)phenyl)-2,3-dihydrobenzo[f][1,4]oxazepin-5-amine | 28 | | | | |
| II-6 | 5-(3,3-difluoropyrrolidin-1-yl)-7-(4-(trifluoromethyl)phenyl)-2,3-dihydrobenzo[f][1,4]oxazepine | 7 | | | | |
| II-7 | N-(pyrimidin-2-ylmethyl)-7-(4-(trifluoromethyl)phenyl)-2,3-dihydrobenzo[f][1,4]oxazepin-5-amine | 14 | | | | |
| II-8 | N-cyclopropyl-N-methyl-7-(4-(trifluoromethyl)phenyl)-2,3-dihydrobenzo[f][1,4]oxazepin-5-amine | 13 | | | | |
| II-9 | N-((3-fluoropyridin-2-yl)methyl)-7-(4-(trifluoromethyl)phenyl)-2,3-dihydrobenzo[f][1,4]oxazepin-5-amine | 23 | | | | |

TABLE 1-continued

| No. | Name | Late I$_{Na}$* | Peak TB* | Peak UDB* | NAV1.1 UDB-10 HZ* | NAV1.2 UDB-10 HZ* |
|---|---|---|---|---|---|---|
| II-10 | N-(pyridin-2-ylmethyl)-7-(4-(trifluoromethyl)phenyl)-2,3-dihydrobenzo[f][1,4]oxazepin-5-amine | 32 | | | | |
| II-11 | N-(cyclopropylmethyl)-7-(4-(trifluoromethyl)phenyl)-2,3-dihydrobenzo[f][1,4]oxazepin-5-amine | 41 | 11 | 31 | | |
| II-12 | tert-butyl 1-(7-(4-(trifluoromethyl)phenyl)-2,3-dihydrobenzo[f][1,4]oxazepin-5-yl)azetidin-3-ylcarbamate | 9 | | | | |
| II-13 | (S)-tert-butyl 1-(7-(4-(trifluoromethyl)phenyl)-2,3-dihydrobenzo[f][1,4]oxazepin-5-yl)pyrrolidin-3-ylcarbamate | 15 | | | | |
| II-14 | N-(2-(1H-imidazol-1-yl)ethyl)-7-(4-(trifluoromethyl)phenyl)-2,3-dihydrobenzo[f][1,4]oxazepin-5-amine | 17 | | | | |
| II-15 | (S)-N,N-dimethyl-1-(7-(4-(trifluoromethyl)phenyl)-2,3-dihydrobenzo[f][1,4]oxazepin-5-yl)pyrrolidin-3-amine | 49 | 16 | 27 | | |
| II-16 | (S)-(1-(7-(4-(trifluoromethyl)phenyl)-2,3-dihydrobenzo[f][1,4]oxazepin-5-yl)pyrrolidin-3-yl)methanol | 13 | | | | |
| II-17 | N-((1-methyl-1H-imidazol-2-yl)methyl)-7-(4-(trifluoromethyl)phenyl)-2,3-dihydrobenzo[f][1,4]oxazepin-5-amine | 10 | | | | |
| II-18 | 1-(7-(4-(trifluoromethyl)phenyl)-2,3-dihydrobenzo[f][1,4]oxazepin-5-yl)azetidin-3-amine | 9 | | | | |
| II-19 | N-(pyridin-2-yl)-7-(4-(trifluoromethyl)phenyl)-2,3-dihydrobenzo[f][1,4]oxazepin-5-amine | 43 | | | | |
| II-20 | N-(2-(pyridin-2-yloxy)ethyl)-7-(4-(trifluoromethyl)phenyl)-dihydrobenzo[f][1,4]oxazepin-5-amine | 59 | 30 | 89 | | |
| II-21 | 5-(4,4-difluoropiperidin-1-yl)-7-(4-(trifluoromethyl)phenyl)-2,3-dihydrobenzo[f][1,4]oxazepine | 13 | | | | |
| II-22 | N-(2-phenoxyethyl)-7-(4-(trifluoromethyl)phenyl)-2,3-dihydrobenzo[f][1,4]oxazepin-5-amine | 60 | 19 | 69 | | |
| II-23 | 1-(7-(4-(trifluoromethyl)phenyl)-2,3-dihydrobenzo[f][1,4]oxazepin-5-yl)pyrrolidin-3-ol | 9 | | | | |
| II-24 | N-(2-(2-chlorophenoxy)ethyl)-7-(4-(trifluoromethyl)phenyl)-2,3-dihydrobenzo[f][1,4]oxazepin-5-amine | 26 | | | | |
| II-25 | 7-(4-(trifluoromethyl)phenyl)-N-((6-(trifluoromethyl)pyridin-2-yl)methyl)-2,3-dihydrobenzo[f][1,4]oxazepin-5-amine | 20 | | | | |
| II-26 | N-(1H-tetrazol-5-yl)-7-(4-(trifluoromethyl)phenyl)-2,3-dihydrobenzo[f][1,4]oxazepin-5-amine | 14 | | | | |
| II-27 | 7-(4-(trifluoromethyl)phenyl)-N-(6- | 1 | | | | |

TABLE 1-continued

| No. | Name | Late $I_{Na}$* | Peak TB* | Peak UDB* | NAV1.1 UDB-10 HZ* | NAV1.2 UDB-10 HZ* |
|---|---|---|---|---|---|---|
| | (trifluoromethyl)pyridin-2-yl)-2,3-dihydrobenzo[f][1,4]oxazepin-5-amine | | | | | |
| II-29 | N-(2,2,2-trifluoro ethyl)-7-(4-(trifluoromethyl)phenyl)-2,3-dihydrobenzo[f][1,4]oxazepin-5-amine | 7 | | | | |
| II-30 | 1-(7-(4-(trifluoromethyl)phenyl)-2,3-dihydrobenzo[f][1,4]oxazepin-5-yl)pyrrolidin-2-one | 10 | | | | |
| II-31 | 5-(4-cyclopropylpiperazin-1-yl)-7-(4-(trifluoromethyl)phenyl)-2,3-dihydrobenzo[f][1,4]oxazepine | 24 | | | | |
| II-32 | N-phenyl-7-(4-(trifluoromethyl)phenyl)-2,3-dihydrobenzo[f][1,4]oxazepin-5-amine | 26 | | | | |
| II-33 | N-((1-methyl-1H-benzo[d]imidazol-2-yl)methyl)-7-(4-(trifluoromethyl)phenyl)-2,3-dihydrobenzo[f][1,4]oxazepin-5-amine | 34 | | | | |
| II-34 | N-(1-(pyrimidin-2-ylmethyl)pyrrolidin-3-yl)-7-(4-(trifluoromethyl)phenyl)-2,3-dihydrobenzo[f][1,4]oxazepin-5-amine | 3 | | | | |
| II-35 | pyrimidin-2-yl(3-(7-(4-(trifluoromethyl)phenyl)-2,3-dihydrobenzo[f][1,4]oxazepin-5-ylamino)pyrrolidin-1-yl)methanone | 4 | | | | |
| II-36 | 5-(1,3'-bipyrrolidin-1'-yl)-7-(4-(trifluoromethyl)phenyl)-2,3-dihydrobenzo[f][1,4]oxazepine | 7 | | | | |
| II-37 | N-(pyrimidin-2-ylmethyl)-1-(7-(4-(trifluoromethyl)phenyl)-2,3-dihydrobenzo[f][1,4]oxazepin-5-yl)pyrrolidin-3-amine | 20 | | | | |
| II-38 | (R)-tert-butyl methyl(1-(7-(4-(trifluoromethyl)phenyl)-2,3-dihydrobenzo[f][1,4]oxazepin-5-yl)pyrrolidin-3-yl)carbamate | 18 | | | | |
| II-39 | (R)-N-methyl-1-(7-(4-(trifluoromethyl)phenyl)-2,3-dihydrobenzo[f][1,4]oxazepin-5-yl)pyrrolidin-3-amine | 26 | | | | |
| II-40 | (S)-tert-butyl methyl(1-(7-(4-(trifluoromethyl)phenyl)-2,3-dihydrobenzo[f][1,4]oxazepin-5-yl)pyrrolidin-3-yl)carbamate | 18 | | | | |
| II-41 | (R)-1-(7-(4-(trifluoromethyl)phenyl)-2,3-dihydrobenzo[f][1,4]oxazepin-5-yl)pyrrolidin-3-amine | 6 | | | | |
| II-42 | 1-(1-(7-(4-(trifluoromethyl)phenyl)-2,3-dihydrobenzo[f][1,4]oxazepin-5-yl)piperidin-4-yl)pyrrolidin-2-one | 9 | | | | |
| II-43 | (S)-tert-butyl 3-(7-(4-(trifluoromethyl)phenyl)-dihydrobenzo[f][1,4]oxazepin-5-ylamino)pyrrolidine-1-carboxylate | 46 | 12 | 31 | | |
| II-44 | (S)-N-methyl-1-(7-(4-(trifluoromethyl)phenyl)-2,3-dihydrobenzo[f][1,4]oxazepin-5-yl)pyrrolidin-3-amine | 9 | | | | |

TABLE 1-continued

| No. | Name | Late I$_{Na}$* | Peak TB* | Peak UDB* | NAV1.1 UDB-10 HZ* | NAV1.2 UDB-10 HZ* |
|---|---|---|---|---|---|---|
| II-45 | (S)-N-(1-(7-(4-(trifluoromethyl)phenyl)-2,3-dihydrobenzo[f][1,4]oxazepin-5-yl)pyrrolidin-3-yl)pyrimidine-2-carboxamide | 6 | | | | |
| II-46 | (R)-N-(1-(7-(4-(trifluoromethyl)phenyl)-2,3-dihydrobenzo[f][1,4]oxazepin-5-yl)pyrrolidin-3-yl)pyrimidine-2-carboxamide | 4 | | | | |
| II-47 | (R)-N-(1-(7-(4-(trifluoromethyl)phenyl)-2,3-dihydrobenzo[f][1,4]oxazepin-5-yl)pyrrolidin-3-yl)picolinamide | 18 | | | | |
| II-48 | (S)-N,N-diethyl-1-(7-(4-(trifluoromethyl)phenyl)-2,3-dihydrobenzo[f][1,4]oxazepin-5-yl)pyrrolidin-3-amine | 24 | | | | |
| II-49 | (R)-N,N-diethyl-1-(7-(4-(trifluoromethyl)phenyl)-2,3-dihydrobenzo[f][1,4]oxazepin-5-yl)pyrrolidin-3-amine | 11 | | | | |
| II-50 | (R)-tert-butyl 1-(7-(4-(trifluoromethyl)phenyl)-2,3-dihydrobenzo[f][1,4]oxazepin-5-yl)pyrrolidin-3-ylcarbamate | 22 | | | | |
| II-51 | (R)-N,N-dimethyl-1-(7-(4-(trifluoromethyl)phenyl)-2,3-dihydrobenzo[f][1,4]oxazepin-5-yl)pyrrolidin-3-amine | 21 | | | | |
| II-52 | 5-(4-methylpiperazin-1-yl)-7-(4-(trifluoromethyl)phenyl)-2,3-dihydrobenzo[f][1,4]oxazepine | 10 | | | | |
| II-53 | (S)-tert-butyl 3-methyl-4-(7-(4-(trifluoromethyl)phenyl)-2,3-dihydrobenzo[f][1,4]oxazepin-5-yl)piperazine-1-carboxylate | 2 | | | | |
| II-54 | N-phenyl-7-(4-(trifluoromethyl)phenyl)-2,3-dihydrobenzo[f][1,4]oxazepin-5-amine | 26 | | | | |
| II-55 | 5-(3-morpholinopyrrolidin-1-yl)-7-(4-(trifluoromethyl)phenyl)-2,3-dihydrobenzo[f][1,4]oxazepine | 18 | | | | |
| II-56 | (S)-1-(7-(4-(trifluoromethyl)phenyl)-2,3-dihydrobenzo[f][1,4]oxazepin-5-yl)pyrrolidin-3-amine | 17 | | | | |
| II-57 | tert-butyl 1-(7-(4-(trifluoromethyl)phenyl)-2,3-dihydrobenzo[f][1,4]oxazepin-5-yl)pyrrolidin-3-ylcarbamate | 23 | | | | |
| II-58 | 5-(2-(pyridin-2-yl)pyrrolidin-1-yl)-7-(4-(trifluoromethyl)phenyl)-2,3-dihydrobenzo[f][1,4]oxazepine | 18 | | | | |
| II-59 | N-(pyrrolidin-3-yl)-7-(4-(trifluoromethyl)phenyl)-2,3-dihydrobenzo[f][1,4]oxazepin-5-amine | 8 | | | | |
| II-60 | 5-(3-(pyridin-2-yl)pyrrolidin-1-yl)-7-(4-(trifluoromethyl)phenyl)-2,3-dihydrobenzo[f][1,4]oxazepine | 42 | 10 | 25 | | |
| II-61 | 1-(naphthalen-1-yloxy)-3-((R)-1-(7-(4-(trifluoromethyl) | 12 | | | | |

TABLE 1-continued

| No. | Name | Late $I_{Na}$* | Peak TB* | Peak UDB* | NAV1.1 UDB-10 HZ* | NAV1.2 UDB-10 HZ* |
|---|---|---|---|---|---|---|
| | phenyl)-2,3-dihydrobenzo[f][1,4]oxazepin-5-yl)pyrrolidin-3-ylamino)propan-2-ol | | | | | |
| II-62 | tert-butyl 3-(7-(4-(trifluoromethyl)phenyl)-2,3-dihydrobenzo[f][1,4]oxazepin-5-ylamino)pyrrolidine-1-carboxylate | 43 | 8 | 32 | | |
| II-63 | (R)-tert-butyl 3-(7-(4-(trifluoromethyl)phenyl)-2,3-dihydrobenzo[f][1,4]oxazepin-5-ylamino)pyrrolidine-1-carboxylate | 51 | 12 | 31 | | |

*% Inhibition at 1 μM.

The assay results shown in the above Table establish that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current.

Example 87

Expression of Human Na$_v$1.1 cDNA

All experiments with human Na$_v$1.1 are conducted as described (Kahlig, et al., PNAS. 2008, 105: 9799-9804). Briefly, expression of hNav1.1 is achieved by transient transfection using Qiagen Superfect reagent (5.5 μg of DNA is transfected at a plasmid mass ratio of 10:1:1 for $\alpha_1:\beta_1:\beta_2$). The human $\beta_1$ and $\beta_2$ cDNAs are cloned into plasmids containing the marker genes DsRed (DsRed-IRES2-h$\beta_1$) or eGFP (eGFP-IRES2-h$\beta_2$) flanking an internal ribosome entry site (IRES).

Electrophysiology

Whole-cell voltage-clamp recordings are used to measure the biophysical properties of WT and mutant Na$_v$1.1 channels, as described previously (Kahlig, 2008). For recording hNav1.1 $I_{Na}$, HEK293 cells are superfused with solution containing (in mM): 145 NaCl, 4 KCl, 1.8 CaCl$_2$, 1 MgCl$_2$, 10 dextrose, 10 HEPES, with a pH of 7.35 and osmolarity of 310 mOsmol/kg. The pipette solution contains (in mM): 110 CsF, 10 NaF, 20 CsCl, 2 EGTA, 10 HEPES, with a pH of 7.35 with an osmolarity of 300 mOsmol/kg. Cells are allowed to stabilize for 10 min after establishment of the whole-cell configuration before current is measured. Series resistance is compensated 90% to assure that the command potential is reached within microseconds with a voltage error<2 mV. Leak currents are subtracted by using an online P/4 procedure and all currents are low-pass Bessel filtered at 5 kHz and digitized at 50 kHz.

For use-dependent studies, cells are stimulated with depolarizing pulse trains (−10 mV, 5 ms, 300 pulses, 10 and 25 Hz) from a holding potential of −120 mV. Currents are then normalized to the peak current recorded in response to the first pulse in each frequency train. For tonic block studies, peak and persistent (late) currents are evaluated in response to a 200 ms depolarization to −10 mV (0.2 Hz) following digital subtraction of currents recorded in the presence and absence of 0.5 μM tetrodotoxin (TTX). The sodium current termed Late INa in the periphery is commonly called persistent INa in the CNS. Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 μL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion. Where appropriate, concentration inhibition curves are fit with the Hill equation: $I/I_{max}=1/[1+10^{\wedge}(\log IC_{50}-I)*k]$, where $IC_{50}$ is the concentration that produces half inhibition and k is the Hill slope factor.

Solutions containing the compounds of the disclosure are perfused for three minutes prior to current recordings to allow equilibrium (tonic) drug block. Tonic block of peak current is measured from this steady-state condition. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition.

In vivo Pharmacology

Jugular vein cannulated male Sprague Dawley rats (250-350 g, Charles River Laboratories, Hollister, Calif.) are used to study brain penetration of the compounds of the disclosure in vivo. Animal use is approved by the Institutional Animal Care and Use Committee, Gilead Sciences. Three rats per group are infused intravenously with the compound of the disclosure in saline at 85.5 μg/kg/min. After 1, 2.5 or 5 h the animals are sacrificed for plasma and brain collection, and concentrations of the compound of the disclosure are measured by liquid chromatography coupled with tandem mass spectrometry (LC-MS/MS). Brain tissue is homogenated in 1% 2N HCl acidified 5% sodium fluoride (final homogenate is diluted 3-fold). Plasma and brain homogenate samples (50 µl) are precipitated along with deuterated D3-Formula I as an internal standard, vortexed and centrifuged. The supernatant (50 µL) is transferred and diluted with water (450 µl) prior to injection (10 µl). High performance liquid chromatography was performed using a Shimadzu LC-10AD liquid chromatograph and a Luna C18(2), 3 µm, 20×2.0 mm column with a mobile phase consisting of water containing 0.1% formic acid (solution A) and acetonitrile (solution B) carried out under isocratic conditions (75% solution A, 25% solution B; flow rate 0.300 ml/min). Mass spectrometric analyses are performed using an API3000 mass spectrometer (Applied Biosystems, Foster City, Calif.) operating in positive ion mode with MRM transition 428.1>98. Brain-to-plasma ratios are calculated for each sample as ng compound/g brain divided by ng compound/ml plasma.

The compound of Example I-2 blocked the Nav1.1 channel current by 1% under Chantest conditions at 10 Hz at 1 µM.

Example 88

Expression of Human $Na_v1.2$ cDNA

Wild-type (WT) cDNA stably transfected in Chinese hamster ovary (CHO) cells is used to record $I_{Na}$. Unless otherwise noted, all reagents are purchased from Sigma-Aldrich (St Louis, Mo., U.S.A.).

Electrophysiology

Whole-cell voltage-clamp recordings are used to measure the biophysical properties of WT. Briefly, the pipette solution consists of (in mM) 110 CsF, 10 NaF, 20 CsCl, 2 EGTA, 10 HEPES, with a pH of 7.35 and osmolarity of 300 mOsmol/kg. The bath (control) solution contains in (mM): 145 NaCl, 4 KCl, 1.8 $CaCl_2$, 1 $MgCl_2$, 10 dextrose, 10 HEPES, with a pH of 7.35 and osmolarity of 310 mOsmol/kg. Cells are allowed to stabilize for 10 min after establishment of the whole-cell configuration before current is measured. Series resistance is compensated 90% to assure that the command potential is reached within microseconds with a voltage error<2 mV. Leak currents are subtracted by using an online P/4 procedure and all currents are low-pass Bessel filtered at 5 kHz and digitized at 50 kHz.

For clarity, representative ramp currents are low pass filtered off-line at 50 Hz. Specific voltage-clamp protocols assessing channel activation, fast inactivation and availability during repetitive stimulation are used. Results are presented as mean±SEM.

Tonic block of peak current is measured using a step to −10 mV (20 ms) from a holding potential of −120 mV (0.2 Hz). Use-dependent block of peak current is measured during pulse number 300 of a pulse train (−10 mV, 5 ms, 300 pulses, 10 Hz or 25 Hz) from a holding potential of −120 mV. Currents are then normalized to the peak current recorded in response to the first pulse in each frequency train. For tonic block studies, peak current is evaluated in response to a 20 ms depolarization to −10 mV (0.2 Hz). Two sequential pulse train stimulations are averaged to obtain mean current traces for each recording condition, which are then used for offline subtraction and analysis.

Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Solutions are perfused for three minutes prior to current recordings to allow equilibrium (tonic) drug block. Tonic block of peak currents is measured from this steady-state condition. Three sequential current traces are averaged to obtain a mean current for each recording. The mean current traces are utilized for offline analysis. Where appropriate, concentration inhibition curves are fit with the Hill equation: $I/I_{max}=1/[1+10^{\wedge}(\log IC_{50}-I)*k]$, where $IC_{50}$ is the concentration that produces half inhibition and k is the Hill slope factor.

Using the above methods it may be demonstrated that the compounds of the disclosure are selective for inhibiting cardiac Late INa current without inhibiting peak and low frequency currents of brain isoforms $Na_v1.1$ and $Na_v1.2$. The compounds of the disclosure may inhibit the very high frequency firing of $Na_v1.1$ and $Na_v1.2$ or demonstrate voltage dependent block of mutant $Na_v1.1$ and $Na_v1.2$ observed with epilepsy patients. In addition compounds of this disclosure may show activity for inhibition of a panel of $Na_v1.1$ mutant channels associated with the epilepsy and headache (migraine) syndromes GEFS+, SMEI and FHM3 suggesting the ability of the compounds of the disclosure to preferentially block the abnormal increased persistent current carried by these mutant channels.

When tested in the assay disclosed above for $hNa_v1.2$ sodium channel isoforms, the compound of Example I-2 blocked the Nav1.2 channel current by 18% under Chantest conditions at 10 Hz at 1 µM. The inhibition of either $hNa_v1.1$ and $hNa_v1.2$ isoforms or the inhibition of both channels when stimulated at these frequencies support the use of compounds of this disclosure to treat patients with epilepsy.

What is claimed is:
1. A compound selected from the group consisting of:

| | |
|---|---|
| I-1 | 10-(4-(trifluoromethyl)phenyl)-5,6-dihydrobenzo[f]imidazo[1,2-d][1,4]oxazepine |
| I-2 | 10-(4-(trifluoromethoxy)phenyl)-5,6-dihydrobenzo[f]imidazo[1,2-d][1,4]oxazepine |
| I-3 | 10-(4-(trifluoromethyl)phenyl)-5,6-dihydrobenzo[f][1,2,4]triazolo[4,3-d][1,4]oxazepine |
| I-4 | 3-methyl-10-(4-(trifluoromethyl)phenyl)-5,6-dihydrobenzo[f][1,2,4]triazolo[4,3-d][1,4]oxazepine |
| I-5 | 3-cyclopropyl-10-(4-(trifluoromethyl)phenyl)-5,6-dihydrobenzo[f][1,2,4]triazolo[4,3-d][1,4]oxazepine |
| I-6 | 3-methyl-10-(4-(trifluoromethyl)phenyl)-5,6-dihydrobenzo[f]imidazo[1,2-d][1,4]oxazepine |
| I-7 | 3-(pyrimidin-2-yl)-10-(4-(trifluoromethyl)phenyl)-5,6-dihydrobenzo[f]imidazo[1,2-d][1,4]oxazepine |
| I-8 | 11-(4-(trifluoromethyl)phenyl)-3,4,6,7-tetrahydro-2H-benzo[f]pyrimido[1,2-d][1,4]oxazepine |
| I-9 | 3-cyclopropyl-10-(4-(trifluoromethyl)phenyl)-5,6-dihydrobenzo[f]imidazo[1,2-d][1,4]oxazepine |

| | |
|---|---|
| I-10 | 2-(10-(4-(trifluoromethyl)phenyl)-5,6-dihydrobenzo[f]imidazo[1,2-d][1,4]oxazepin-3-yl)propan-2-ol |
| I-11 | 3-benzyl-10-(4-(trifluoromethyl)phenyl)-5,6-dihydrobenzo[f]imidazo[1,2-d][1,4]oxazepine |
| I-12 | 3-bromo-10-(4-(trifluoromethyl)phenyl)-5,6-dihydrobenzo[f]imidazo[1,2-d][1,4]oxazepine |
| I-13 | 3-chloro-10-(4-(trifluoromethyl)phenyl)-5,6-dihydrobenzo[f]imidazo[1,2-d][1,4]oxazepine |
| I-14 | 2-chloro-3-methyl-10-(4-(trifluoromethyl)phenyl)-5,6-dihydrobenzo[f]imidazo[1,2-d][1,4]oxazepine |
| I-15 | 1-(10-(4-(trifluoromethyl)phenyl)-5,6-dihydrobenzo[f]imidazo[1,2-d][1,4]oxazepin-3-yl)ethanone |
| I-16 | 10-(4-(trifluoromethyl)phenyl)-5,6-dihydrobenzo[f]imidazo[1,2-d][1,4]oxazepine-3-carbonitrile |
| I-17 | 3-methyl-10-(4-(trifluoromethoxy)phenyl)-5,6-dihydrobenzo[f]imidazo[1,2-d][1,4]oxazepine |
| I-18 | 3-cyclopropyl-10-(4-(trifluoromethoxy)phenyl)-5,6-dihydrobenzo[f]imidazo[1,2-d][1,4]oxazepine |
| I-19 | 2-methyl-10-(4-(trifluoromethyl)phenyl)-5,6-dihydrobenzo[f]imidazo[1,2-d][1,4]oxazepine |
| I-20 | 2-cyclopropyl-10-(4-(trifluoromethyl)phenyl)-5,6-dihydrobenzo[f]imidazo[1,2-d][1,4]oxazepine |
| I-21 | ethyl 10-(4-(trifluoromethyl)phenyl)-5,6-dihydrobenzo[f]imidazo[1,2-d][1,4]oxazepine-2-carboxylate |
| I-22 | 10-(4-(trifluoromethyl)phenyl)-5,6-dihydrobenzo[f]imidazo[1,2-d][1,4]oxazepine-2-carboxylic acid |
| I-23 | 2-(1-methyl-1H-imidazol-5-yl)-10-(4-(trifluoromethyl)phenyl)-5,6-dihydrobenzo[f]imidazo[1,2-d][1,4]oxazepine |
| II-1 | 5-morpholino-7-(4-(trifluoromethyl)phenyl)-2,3-dihydrobenzo[f][1,4]oxazepine |
| II-2 | N-benzyl-7-(4-(trifluoromethyl)phenyl)-2,3-dihydrobenzo[f][1,4]oxazepin-5-amine |
| II-3 | 5-(pyrrolidin-1-yl)-7-(4-(trifluoromethyl)phenyl)-2,3-dihydrobenzo[f][1,4]oxazepine |
| II-4 | N-cyclopropyl-7-(4-(trifluoromethyl)phenyl)-2,3-dihydrobenzo[f][1,4]oxazepin-5-amine |
| II-5 | N-benzyl-N-methyl-7-(4-(trifluoromethyl)phenyl)-2,3-dihydrobenzo[f][1,4]oxazepin-5-amine |
| II-6 | 5-(3,3-difluoropyrrolidin-1-yl)-7-(4-(trifluoromethyl)phenyl)-2,3-dihydrobenzo[f][1,4]oxazepine |
| II-7 | N-(pyrimidin-2-ylmethyl)-7-(4-(trifluoromethyl)phenyl)-2,3-dihydrobenzo[f][1,4]oxazepin-5-amine |
| II-8 | N-cyclopropyl-N-methyl-7-(4-(trifluoromethyl)phenyl)-2,3-dihydrobenzo[f][1,4]oxazepin-5-amine |
| II-9 | N-((3-fluoropyridin-2-yl)methyl)-7-(4-(trifluoromethyl)phenyl)-2,3-dihydrobenzo[f][1,4]oxazepin-5-amine |
| II-10 | N-(pyridin-2-ylmethyl)-7-(4-(trifluoromethyl)phenyl)-2,3-dihydrobenzo[f][1,4]oxazepin-5-amine |
| II-11 | N-(cyclopropylmethyl)-7-(4-(trifluoromethyl)phenyl)-2,3-dihydrobenzo[f][1,4]oxazepin-5-amine |
| II-12 | tert-butyl 1-(7-(4-(trifluoromethyl)phenyl)-2,3-dihydrobenzo[f][1,4]oxazepin-5-yl)azetidin-3-ylcarbamate |
| II-13 | (S)-tert-butyl 1-(7-(4-(trifluoromethyl)phenyl)-2,3-dihydrobenzo[f][1,4]oxazepin-5-yl)pyrrolidin-3-ylcarbamate |
| II-14 | N-(2-(1H-imidazol-1-yl)ethyl)-7-(4-(trifluoromethyl)phenyl)-2,3-dihydrobenzo[f][1,4]oxazepin-5-amine |
| II-15 | (S)-N,N-dimethyl-1-(7-(4-(trifluoromethyl)phenyl)-2,3-dihydrobenzo[f][1,4]oxazepin-5-yl)pyrrolidin-3-amine |
| II-16 | (S)-(1-(7-(4-(trifluoromethyl)phenyl)-2,3-dihydrobenzo[f][1,4]oxazepin-5-yl)pyrrolidin-3-yl)methanol |
| II-17 | N-((1-methyl-1H-imidazol-2-yl)methyl)-7-(4-(trifluoromethyl)phenyl)-2,3-dihydrobenzo[f][1,4]oxazepin-5-amine |
| II-18 | 1-(7-(4-(trifluoromethyl)phenyl)-2,3-dihydrobenzo[f][1,4]oxazepin-5-yl)azetidin-3-amine |
| II-19 | N-(pyridin-2-yl)-7-(4-(trifluoromethyl)phenyl)-2,3-dihydrobenzo[f][1,4]oxazepin-5-amine |
| II-20 | N-(2-(pyridin-2-yloxy)ethyl)-7-(4-(trifluoromethyl)phenyl)-2,3-dihydrobenzo[f][1,4]oxazepin-5-amine |
| II-21 | 5-(4,4-difluoropiperidin-1-yl)-7-(4-(trifluoromethyl)phenyl)-2,3-dihydrobenzo[f][1,4]oxazepine |
| II-22 | N-(2-phenoxyethyl)-7-(4-(trifluoromethyl)phenyl)-2,3-dihydrobenzo[f][1,4]oxazepin-5-amine |
| II-23 | 1-(7-(4-(trifluoromethyl)phenyl)-2,3-dihydrobenzo[f][1,4]oxazepin-5-yl)pyrrolidin-3-ol |
| II-24 | N-(2-(2-chlorophenoxy)ethyl)-7-(4-(trifluoromethyl)phenyl)-2,3-dihydrobenzo[f][1,4]oxazepin-5-amine |
| II-25 | 7-(4-(trifluoromethyl)phenyl)-N-((6-(trifluoromethyl)pyridin-2-yl)methyl)-2,3-dihydrobenzo[f][1,4]oxazepin-5-amine |
| II-26 | N-(1H-tetrazol-5-yl)-7-(4-(trifluoromethyl)phenyl)-2,3-dihydrobenzo[f][1,4]oxazepin-5-amine |
| II-27 | 7-(4-(trifluoromethyl)phenyl)-N-(6-(trifluoromethyl)pyridin-2-yl)-2,3-dihydrobenzo[f][1,4]oxazepin-5-amine |
| II-28 | 5-(4-(2,2,2-trifluoroethyl)piperazin-1-yl)-7-(4-(trifluoromethyl)phenyl)-2,3-dihydrobenzo[f][1,4]oxazepine |
| II-29 | N-(2,2,2-trifluoroethyl)-7-(4-(trifluoromethyl)phenyl)-2,3-dihydrobenzo[f][1,4]oxazepin-5-amine |
| II-30 | 1-(7-(4-(trifluoromethyl)phenyl)-2,3-dihydrobenzo[f][1,4]oxazepin-5-yl)pyrrolidin-2-one |
| II-31 | 5-(4-cyclopropylpiperazin-1-yl)-7-(4-(trifluoromethyl)phenyl)-2,3-dihydrobenzo[f][1,4]oxazepine |
| II-32 | N-phenyl-7-(4-(trifluoromethyl)phenyl)-2,3-dihydrobenzo[f][1,4]oxazepin-5-amine |
| II-33 | N-((1-methyl-1H-benzo[d]imidazol-2-yl)methyl)-7-(4-(trifluoromethyl)phenyl)-2,3-dihydrobenzo[f][1,4]oxazepin-5-amine |
| II-34 | N-(1-(pyrimidin-2-ylmethyl)pyrrolidin-3-yl)-7-(4-(trifluoromethyl)phenyl)-2,3-dihydrobenzo[f][1,4]oxazepin-5-amine |
| II-35 | pyrimidin-2-yl(3-(7-(4-(trifluoromethyl)phenyl)-2,3-dihydrobenzo[f][1,4]oxazepin-5-ylamino)pyrrolidin-1-yl)methanone |
| II-36 | 5-(1,3'-bipyrrolidin-r-yl)-7-(4-(trifluoromethyl)phenyl)-2,3-dihydrobenzo[f][1,4]oxazepine |
| II-37 | N-(pyrimidin-2-ylmethyl)-1-(7-(4-(trifluoromethyl)phenyl)-2,3-dihydrobenzo[f][1,4]oxazepin-5-yl)pyrrolidin-3-amine |
| II-38 | (R)-tert-butyl methyl(1-(7-(4-(trifluoromethyl)phenyl)-2,3-dihydrobenzo[f][1,4]oxazepin-5-yl)pyrrolidin-3-yl)carbamate |
| II-39 | (R)-N-methyl-1-(7-(4-(trifluoromethyl)phenyl)-2,3-dihydrobenzo[f][1,4]oxazepin-5-yl)pyrrolidin-3-amine |
| II-40 | (S)-tert-butylmethyl(1-(7-(4-(trifluoromethyl)phenyl)-2,3-dihydrobenzo[f][1,4]oxazepin-5-yl)pyrrolidin-3-yl)carbamate |
| II-41 | (R)-1-(7-(4-(trifluoromethyl)phenyl)-2,3-dihydrobenzo[f][1,4]oxazepin-5-yl)pyrrolidin-3-amine |
| II-42 | 1-(1-(7-(4-(trifluoromethyl)phenyl)-2,3-dihydrobenzo[f][1,4]oxazepin-5-yl)piperidin-4-yl)pyrrolidin-2-one |
| II-43 | (S)-tert-butyl 3-(7-(4-(trifluoromethyl)phenyl)-2,3-dihydrobenzo[f][1,4]oxazepin-5-ylamino)pyrrolidine-1-carboxylate |
| II-44 | (S)-N-methyl-1-(7-(4-(trifluoromethyl)phenyl)-2,3-dihydrobenzo[f][1,4]oxazepin-5-yl)pyrrolidin-3-amine |
| II-45 | (S)-N-(1-(7-(4-(trifluoromethyl)phenyl)-2,3-dihydrobenzo[f][1,4]oxazepin-5-yl)pyrrolidin-3-yl)pyrimidine-2-carboxamide |
| II-46 | (R)-N-(1-(7-(4-(trifluoromethyl)phenyl)-2,3-dihydrobenzo[f][1,4]oxazepin-5-yl)pyrrolidin-3-yl)pyrimidine-2-carboxamide- |
| II-47 | (R)-N-(1-(7-(4-(trifluoromethyl)phenyl)-2,3-dihydrobenzo[f][1,4]oxazepin-5-yl)pyrrolidin-3-yl)picolinamide |
| II-48 | (S)-N,N-diethyl-1-(7-(4-(trifluoromethyl)phenyl)-2,3-dihydrobenzo[f][1,4]oxazepin-5-yl)pyrrolidin-3-amine |
| II-49 | (R)-N,N-diethyl-1-(7-(4-(trifluoromethyl)phenyl)-2,3-dihydrobenzo[f][1,4]oxazepin-5-yl)pyrrolidin-3-amine |
| II-50 | (R)-tert-butyl 1-(7-(4-(trifluoromethyl)phenyl)-2,3-dihydrobenzo[f][1,4]oxazepin-5-yl)pyrrolidin-3-ylcarbamate |
| II-51 | (R)-N,N-dimethyl-1-(7-(4-(trifluoromethyl)phenyl)-2,3-dihydrobenzo[f][1,4]oxazepin-5-yl)pyrrolidin-3-amine |
| II-52 | 5-(4-methylpiperazin-1-yl)-7-(4-(trifluoromethyl)phenyl)-2,3-dihydrobenzo[f][1,4]oxazepine |
| II-53 | (S)-tert-butyl 3-methyl-4-(7-(4-(trifluoromethyl)phenyl)-2,3-dihydrobenzo[f][1,4]oxazepin-5-yl)piperazine-1-carboxylate |
| II-55 | 5-(3-morpholinopyrrolidin-1-yl)-7-(4-(trifluoromethyl)phenyl)-2,3-dihydrobenzo[f][1,4]oxazepine |
| II-56 | (S)-1-(7-(4-(trifluoromethyl)phenyl)-2,3-dihydrobenzo[f][1,4]oxazepin-5-yl)pyrrolidin-3-amine |
| II-57 | tert-butyl 1-(7-(4-(trifluoromethyl)phenyl)-2,3-dihydrobenzo[f][1,4]oxazepin-5-yl)pyrrolidin-3-ylcarbamate |
| II-58 | 5-(2-(pyridin-2-yl)pyrrolidin-1-yl)-7-(4-(trifluoromethyl)phenyl)-2,3-dihydrobenzo[f][1,4]oxazepine |
| II-59 | N-(pyrrolidin-3-yl)-7-(4-(trifluoromethyl)phenyl)-2,3-dihydrobenzo[f][1,4]oxazepin-5-amine |
| II-60 | 5-(3-(pyridin-2-yl)pyrrolidin-1-yl)-7-(4-(trifluoromethyl)phenyl)-2,3-dihydrobenzo[f][1,4]oxazepine |
| II-61 | 1-(naphthalen-1-yloxy)-3-((R)-1-(7-(4-(trifluoromethyl)phenyl)-2,3-dihydrobenzo[f][1,4]oxazepin-5-yl)pyrrolidin-3-ylamino)propan-2-ol |
| II-62 | tert-butyl 3-(7-(4-(trifluoromethyl)phenyl)-2,3-dihydrobenzo[f][1,4]oxazepin-5-ylamino)pyrrolidine-1-carboxylate |
| II-63 | (R)-tert-butyl3-(7-(4-(trifluoromethyl)phenyl)-2,3-dihydrobenzo[f][1,4]oxazepin-5-ylamino)pyrrolidine-1-carboxylate | or a pharmaceutically acceptable salt, stereoisomer, mixture of stereoisomers, or tautomer thereof.

2. A compound selected from the group consisting of:

| | |
|---|---|
| I-1 | 10-(4-(trifluoromethyl)phenyl)-5,6-dihydrobenzo[f]imidazo[1,2-d][1,4]oxazepine |
| I-2 | 10-(4-(trifluoromethoxy)phenyl)-5,6-dihydrobenzo[f]imidazo[1,2-d][1,4]oxazepine |
| I-3 | 10-(4-(trifluoromethyl)phenyl)-5,6-dihydrobenzo[f][1,2,4]triazolo[4,3-d][1,4]oxazepine |
| I-4 | 3-methyl-10-(4-(trifluoromethyl)phenyl)-5,6-dihydrobenzo[f][1,2,4]triazolo[4,3-d][1,4]oxazepine |
| I-9 | 3-cyclopropyl-10-(4-(trifluoromethyl)phenyl)-5,6-dihydrobenzo[f]imidazo[1,2-d][1,4]oxazepine |
| I-10 | 2-(10-(4-(trifluoromethyl)phenyl)-5,6-dihydrobenzo[f]imidazo[1,2-d][1,4]oxazepin-3-yl)propan-2-ol |
| I-11 | 3-benzyl-10-(4-(trifluoromethyl)phenyl)-5,6-dihydrobenzo[f]imidazo[1,2-d][1,4]oxazepine |
| I-12 | 3-bromo-10-(4-(trifluoromethyl)phenyl)-5,6-dihydrobenzo[f]imidazo[1,2-d][1,4]oxazepine |
| I-13 | 3-chloro-10-(4-(trifluoromethyl)phenyl)-5,6-dihydrobenzo[f]imidazo[1,2-d][1,4]oxazepine |
| I-14 | 2-chloro-3-methyl-10-(4-(trifluoromethyl)phenyl)-5,6-dihydrobenzo[f]imidazo[1,2-d][1,4]oxazepine |
| I-15 | 1-(10-(4-(trifluoromethyl)phenyl)-5,6-dihydrobenzo[f]imidazo[1,2-d][1,4]oxazepin-3-yl)ethanone |
| I-16 | 10-(4-(trifluoromethyl)phenyl)-5,6-dihydrobenzo[f]imidazo[1,2-d][1,4]oxazepine-3-carbonitrile |
| I-17 | 3-methyl-10-(4-(trifluoromethoxy)phenyl)-5,6-dihydrobenzo[f]imidazo[1,2-d][1,4]oxazepine |
| I-18 | 3-cyclopropyl-10-(4-(trifluoromethoxy)phenyl)-5,6-dihydrobenzo[f]imidazo[1,2-d][1,4]oxazepine |
| I-19 | 2-methyl-10-(4-(trifluoromethyl)phenyl)-5,6-dihydrobenzo[f]imidazo[1,2-d][1,4]oxazepine |
| I-20 | 2-cyclopropyl-10-(4-(trifluoromethyl)phenyl)-5,6-dihydrobenzo[f]imidazo[1,2-d][1,4]oxazepine |
| I-21 | ethyl 10-(4-(trifluoromethyl)phenyl)-5,6-dihydrobenzo[f]imidazo[1,2-d][1,4]oxazepine-2-carboxylate |
| I-22 | 10-(4-(trifluoromethyl)phenyl)-5,6-dihydrobenzo[f]imidazo[1,2-d][1,4]oxazepine-2-carboxylic acid |
| I-23 | 2-(1-methyl-1H-imidazol-5-yl)-10-(4-(trifluoromethyl)phenyl)-5,6-dihydrobenzo[f]imidazo[1,2-d][1,4]oxazepine | or a pharmaceutically acceptable salt, stereoisomer, mixture of stereoisomers, or tautomer thereof.

3. A compound selected from the group consisting of:

| | |
|---|---|
| II-6 | 5-(3,3-difluoropyrrolidin-1-yl)-7-(4-(trifluoromethyl)phenyl)-2,3-dihydrobenzo[f][1,4]oxazepine |
| II-7 | N-(pyrimidin-2-ylmethyl)-7-(4-(trifluoromethyl)phenyl)-2,3-dihydrobenzo[f][1,4]oxazepin-5-amine |
| II-8 | N-cyclopropyl-N-methyl-7-(4-(trifluoromethyl)phenyl)-2,3-dihydrobenzo[f][1,4]oxazepin-5-amine |
| II-12 | tert-butyl 1-(7-(4-(trifluoromethyl)phenyl)-2,3-dihydrobenzo[f][1,4]oxazepin-5-yl)azetidin-3-ylcarbamate |
| II-16 | (S)-(1-(7-(4-(trifluoromethyl)phenyl)-2,3-dihydrobenzo[f][1,4]oxazepin-5-yl)pyrrolidin-3-yl)methanol |
| II-17 | N-((1-methyl-1H-imidazol-2-yl)methyl)-7-(4-(trifluoromethyl)phenyl)-2,3-dihydrobenzo[f][1,4]oxazepin-5-amine |
| II-18 | 1-(7-(4-(trifluoromethyl)phenyl)-2,3-dihydrobenzo[f][1,4]oxazepin-5-yl)azetidin-3-amine |
| II-21 | 5-(4,4-difluoropiperidin-1-yl)-7-(4-(trifluoromethyl)phenyl)-2,3-dihydrobenzo[f][1,4]oxazepine |
| II-23 | 1-(7-(4-(trifluoromethyl)phenyl)-2,3-dihydrobenzo[f][1,4]oxazepin-5-yl)pyrrolidin-3-ol |
| II-26 | N-(1H-tetrazol-5-yl)-7-(4-(trifluoromethyl)phenyl)-2,3-dihydrobenzo[f][1,4]oxazepin-5-amine |
| II-27 | 7-(4-(trifluoromethyl)phenyl)-N-(6-(trifluoromethyl)pyridin-2-yl)-2,3-dihydrobenzo[f][1,4]oxazepin-5-amine |
| II-28 | 5-(4-(2,2,2-trifluoroethyl)piperazin-1-yl)-7-(4-(trifluoromethyl)phenyl)-2,3-dihydrobenzo[f][1,4]oxazepine |
| II-29 | N-(2,2,2-trifluoroethyl)-7-(4-(trifluoromethyl)phenyl)-2,3-dihydrobenzo[f][1,4]oxazepin-5-amine |
| II-30 | 1-(7-(4-(trifluoromethyl)phenyl)-2,3-dihydrobenzo[f][1,4]oxazepin-5-yl)pyrrolidin-2-one |
| II-34 | N-(1-(pyrimidin-2-ylmethyl)pyrrolidin-3-yl)-7-(4-(trifluoromethyl)phenyl)-2,3-dihydrobenzo[f][1,4]oxazepin-5-amine |
| II-35 | pyrimidin-2-yl(3-(7-(4-(trifluoromethyl)phenyl)-2,3-dihydrobenzo[f][1,4]oxazepin-5-ylamino)pyrrolidin-1-yl)methanone |
| II-36 | 5-(1,3'-bipyrrolidin-1'-yl)-7-(4-(trifluoromethyl)phenyl)-2,3-dihydrobenzo[f][1,4]oxazepine |

-continued

| | |
|---|---|
| II-41 | (R)-1-(7-(4-(trifluoromethyl)phenyl)-2,3-dihydrobenzo[f][1,4]oxazepin-5-yl)pyrrolidin-3-amine |
| II-42 | 1-(1-(7-(4-(trifluoromethyl)phenyl)-2,3-dihydrobenzo[f][1,4]oxazepin-5-yl)piperidin-4-yl)pyrrolidin-2-one |
| II-44 | (S)-N-methyl-1-(7-(4-(trifluoromethyl)phenyl)-2,3-dihydrobenzo[f][1,4]oxazepin-5-yl)pyrrolidin-3-amine |
| II-45 | (S)-N-(1-(7-(4-(trifluoromethyl)phenyl)-2,3-dihydrobenzo[f][1,4]oxazepin-5-yl)pyrrolidin-3-yl)pyrimidine-2-carboxamide |
| II-46 | (R)-N-(1-(7-(4-(trifluoromethyl)phenyl)-2,3-dihydrobenzo[f][1,4]oxazepin-5-yl)pyrrolidin-3-yl)pyrimidine-2-carboxamide |
| II-49 | (R)-N,N-diethyl-1-(7-(4-(trifluoromethyl)phenyl)-2,3-dihydrobenzo[f][1,4]oxazepin-5-yl)pyrrolidin-3-amine |
| II-52 | 5-(4-methylpiperazin-1-yl)-7-(4-(trifluoromethyl)phenyl)-2,3-dihydrobenzo[f][1,4]oxazepine |
| II-53 | (S)-tert-butyl 3-methyl-4-(7-(4-(trifluoromethyl)phenyl)-2,3-dihydrobenzo[f][1,4]oxazepin-5-yl)piperazine-1-carboxylate |
| II-59 | N-(pyrrolidin-3-yl)-7-(4-(trifluoromethyl)phenyl)-2,3-dihydrobenzo[f][1,4]oxazepin-5-amine | or a pharmaceutically acceptable salt, stereoisomer, mixture of stereoisomers, or tautomer thereof.

4. A method of treating a disease state in a human, wherein the disease state is selected from diabetes, diabetic peripheral neuropathy, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication, comprising administering to a human in need thereof a therapeutically effective dose of a compound of claim 1.

5. The method of claim 4, wherein the disease state is diabetes or diabetic peripheral neuropathy.

6. The method of claim 4, wherein the disease state results in one or more of neuropathic pain, epilepsy, seizures, headache or paralysis.

7. A pharmaceutical composition comprising a pharmaceutically acceptable excipient and a therapeutically effective amount of the compound of claim 1 or a pharmaceutically acceptable salt thereof.

* * * * *